United States Patent
Boveja et al.

(10) Patent No.: US 7,330,762 B2
(45) Date of Patent: Feb. 12, 2008

(54) METHOD AND SYSTEM FOR PROVIDING PULSED ELECTRICAL STIMULATION TO PROVIDE THERAPY FOR ERECTILE/SEXUAL DYSFUNCTION, PROSTATITIS, PROSTATITIS PAIN, AND CHRONIC PELVIC PAIN

(75) Inventors: Birinder R. Boveja, Milwaukee, WI (US); Angely Widhany, Milwaukee, WI (US)

(73) Assignee: Neuro and Cardiac Technologies, LLC, Milwaukee, WI (US)

( * ) Notice: Subject to any disclaimer, the term of this patent is extended or adjusted under 35 U.S.C. 154(b) by 165 days.

(21) Appl. No.: 10/862,630

(22) Filed: Jun. 7, 2004

(65) Prior Publication Data
US 2005/0131484 A1 Jun. 16, 2005

(51) Int. Cl.
*A61N 1/08* (2006.01)
(52) U.S. Cl. ............... 607/39; 607/60; 607/61
(58) Field of Classification Search ............ 607/39–41, 607/46, 59, 60
See application file for complete search history.

(56) References Cited

U.S. PATENT DOCUMENTS

| | | | |
|---|---|---|---|
| 5,938,584 A * | 8/1999 | Ardito et al. ................ 600/38 |
| 6,169,924 B1 | 1/2001 | Meloy et al. ................. 607/39 |
| 6,449,512 B1 * | 9/2002 | Boveja ......................... 607/41 |
| 6,453,195 B1 * | 9/2002 | Thompson .................... 607/3 |
| 6,505,074 B2 * | 1/2003 | Boveja et al. ................ 607/41 |
| 6,650,943 B1 | 11/2003 | Whitehurst et al. .......... 607/39 |
| 6,760,626 B1 * | 7/2004 | Boveja ......................... 607/59 |
| 6,805,667 B2 * | 10/2004 | Christopherson et al. ... 600/300 |
| 2003/0004553 A1 * | 1/2003 | Grill et al. .................... 607/40 |
| 2003/0236557 A1 | 12/2003 | Whitehurst et al. .......... 607/39 |
| 2004/0049240 A1 | 3/2004 | Gerber et al. ................ 607/40 |
| 2004/0073268 A1 | 4/2004 | Zappala ....................... 607/39 |
| 2005/0010260 A1 * | 1/2005 | Gerber ......................... 607/39 |

OTHER PUBLICATIONS

Shafik A., Extrapelvic cavernous nerve stimulation in erectile dysfunction. Human study, Andrologia 28, pp. 151-156 (1996).

(Continued)

*Primary Examiner*—Mark Bockelman
*Assistant Examiner*—Eric D. Bertram

(57) ABSTRACT

A method and system for providing pulse electrical stimulation to at least one of sacral plexus or its branches or portions, inferior hypogastric plexus or its branches or portions, superior hypogastric plexus or its branches or portions in a patient, to provide therapy for one of erectile/sexual dysfunction, prostatitis, pelvic pain, and pain originating from prostatitis pathology. The stimulation system comprises both implanted and external components. The pulsed electrical stimulation may be provided using one of the following stimulation systems: a) an implanted stimulus-receiver with an external stimulator; b) an implanted stimulus-receiver comprising a high value capacitor for storing charge, used in conjunction with an external stimulator; c) a programmer-less implantable pulse generator (IPG) which is operable with an external magnet; d) a programmable implantable pulse generator; e) a combination implantable device comprising both a stimulus-receiver and a programmable IPG; and f) an implantable pulse generator (IPG) comprising a rechargeable battery. The stimulation pulses can be provided uni-directionally. In one embodiment, the external components such as the programmer or external stimulator may comprise a telemetry means for networking. The telemetry means therefore, allows for interrogation or programming of implanted device from a remote location, over a wide area network.

18 Claims, 63 Drawing Sheets

OTHER PUBLICATIONS

Lue T. F. et al., Electrostimulation and penile erection, Urol. Int., Urol. Int. 40: pp. 60-64 (1985).

Martinez-Pineiro L. et al., Rat model for the study of penile erection, pharmacologic and electrical-stimulation parameters, Eur. urol. 25: pp. 62-70 (1994).

Shafik A. et al, Magnetic stimulation of the cavernous nerve for the treatment of erectile dysfunction in humans., Int. J. Impot. Res. 12(3) pp. 137-142 (2000). (Abstract enclosed).

Shafik A. et al., Perineal nerve stimulation: Role in penile erection., Int. J. Impot. Res. 9 pp. 11-16 (1997). (Abstract enclosed).

* cited by examiner

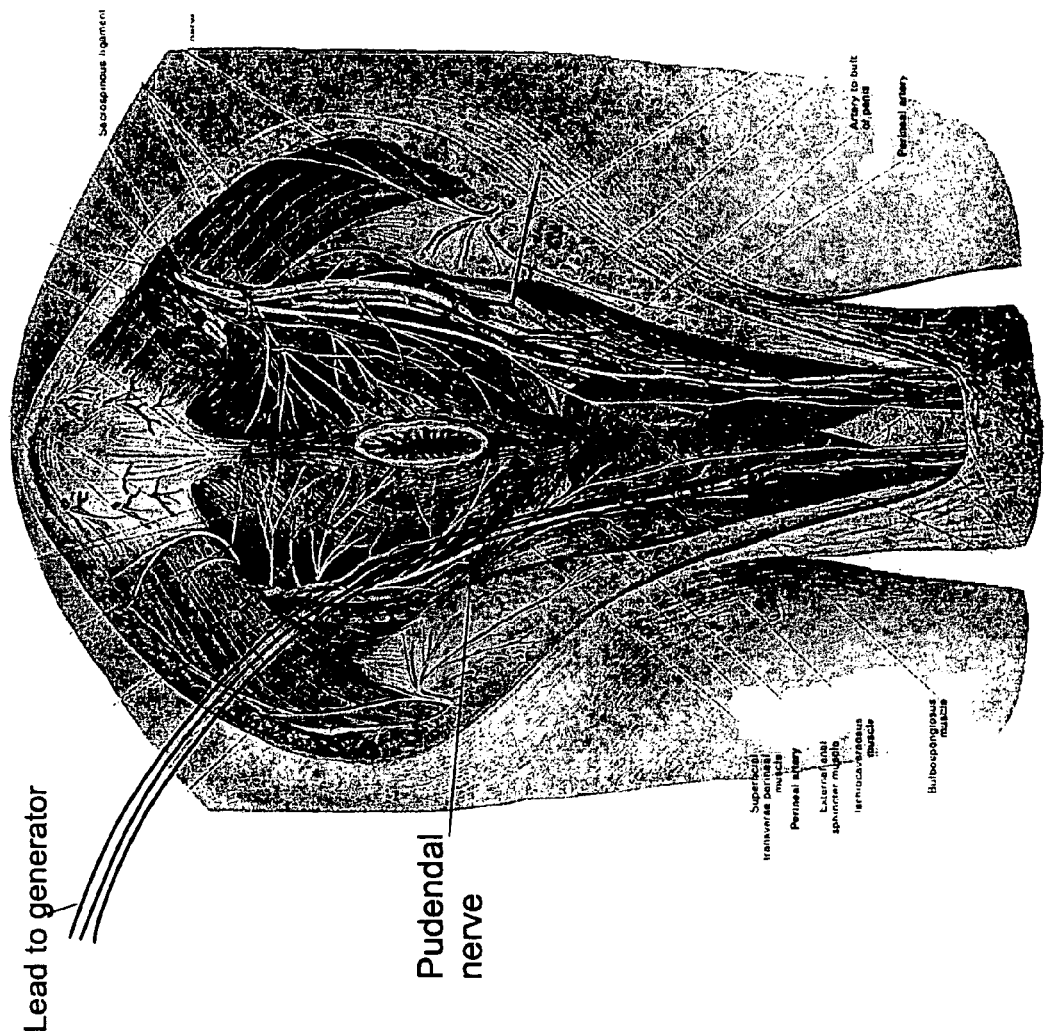

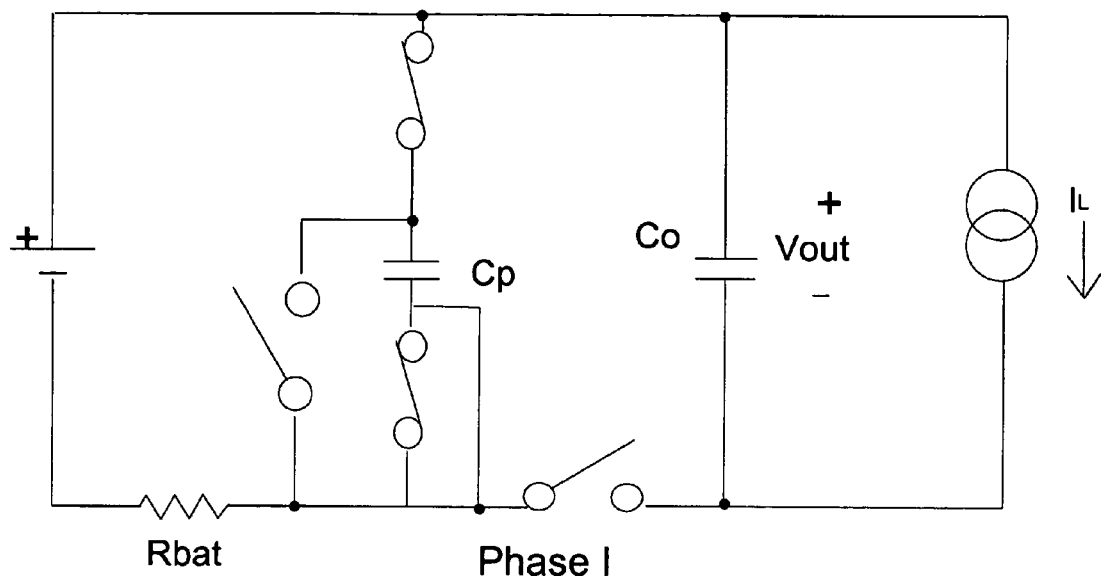
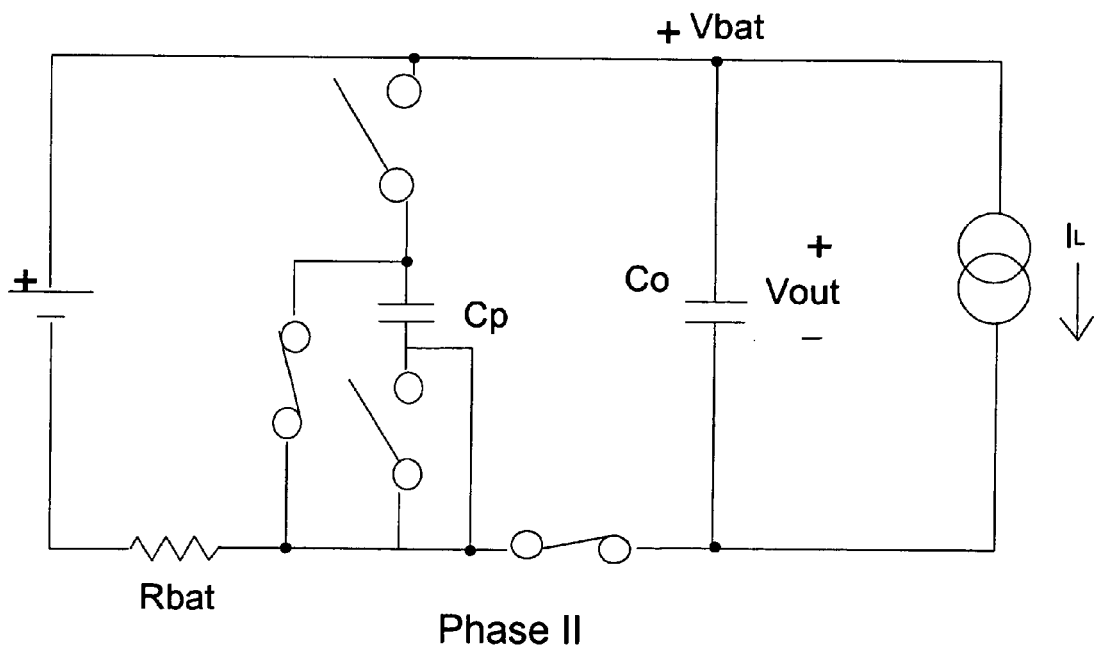
FIG. 35

| Axons from skin | Aα | Aβ | Aδ | C |
|---|---|---|---|---|
| Axons from muscles | Group I | II | III | IV |
|  | 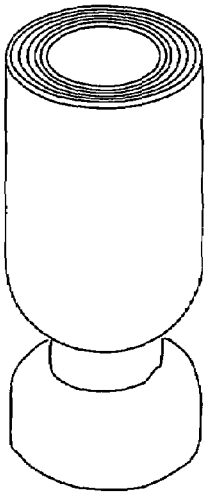 | 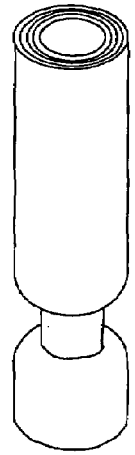 |  |  |
| Diameter (μm) | 13-20 | 6-12 | 1-5 | 0.2-1.5 |
| Speed (m/sec) | 80-120 | 35-75 | 5-30 | 0.5-2 |
| Sensory receptors | Proprioceptors of skeletal muscle | Mechanoreceptors of skin | Pain temperature | Temperature, pain, itch |
FIG. 38

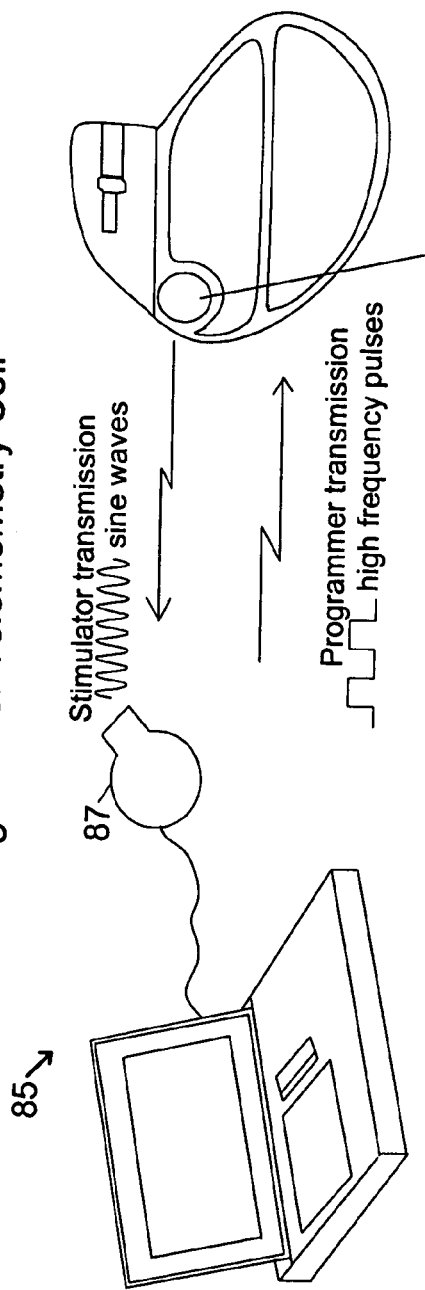
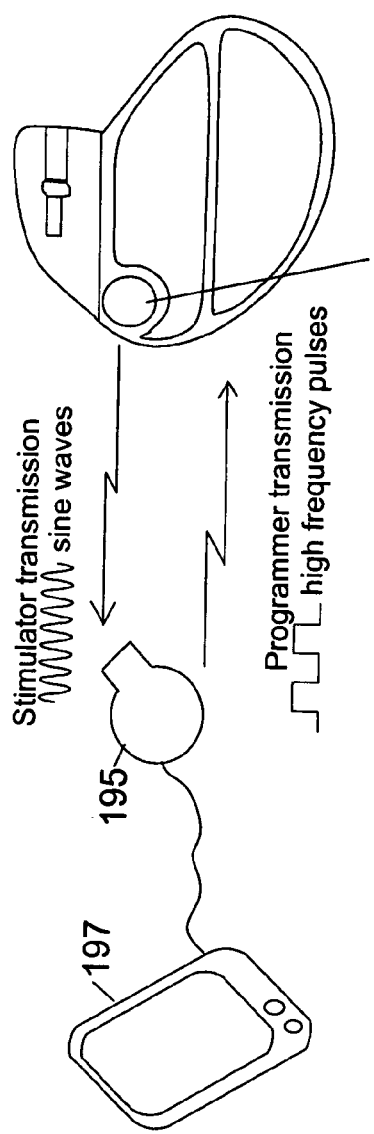
FIG. 40A
FIG. 40B

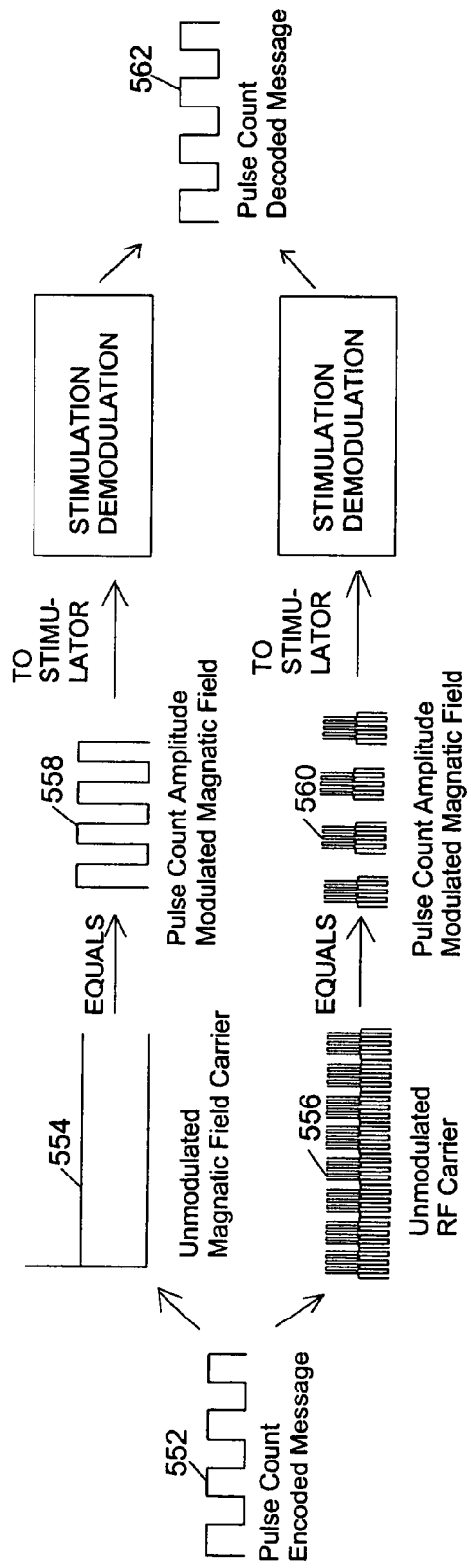
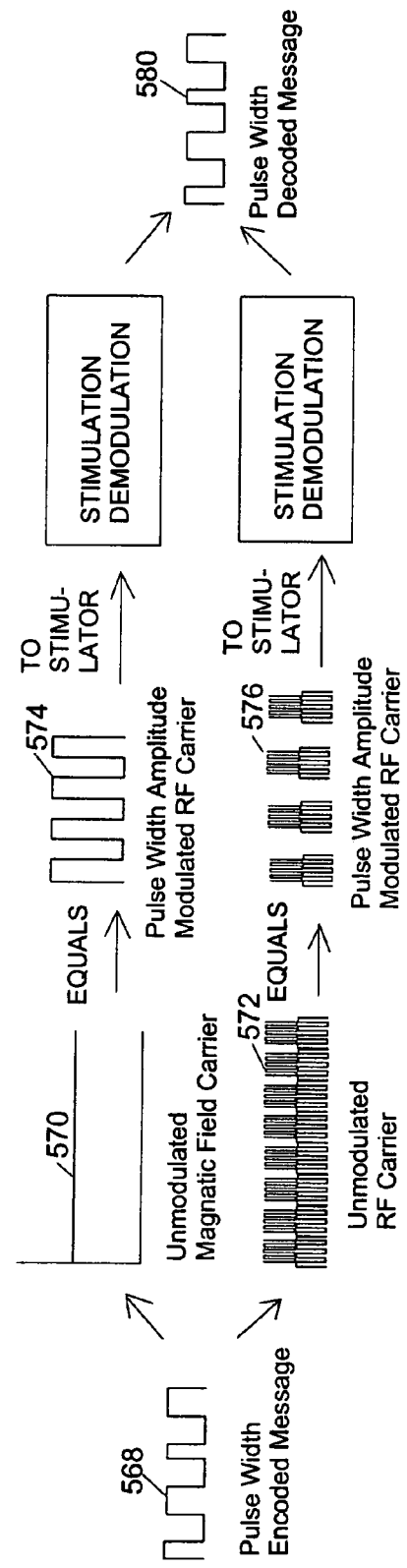
FIG. 41A
FIG. 41B

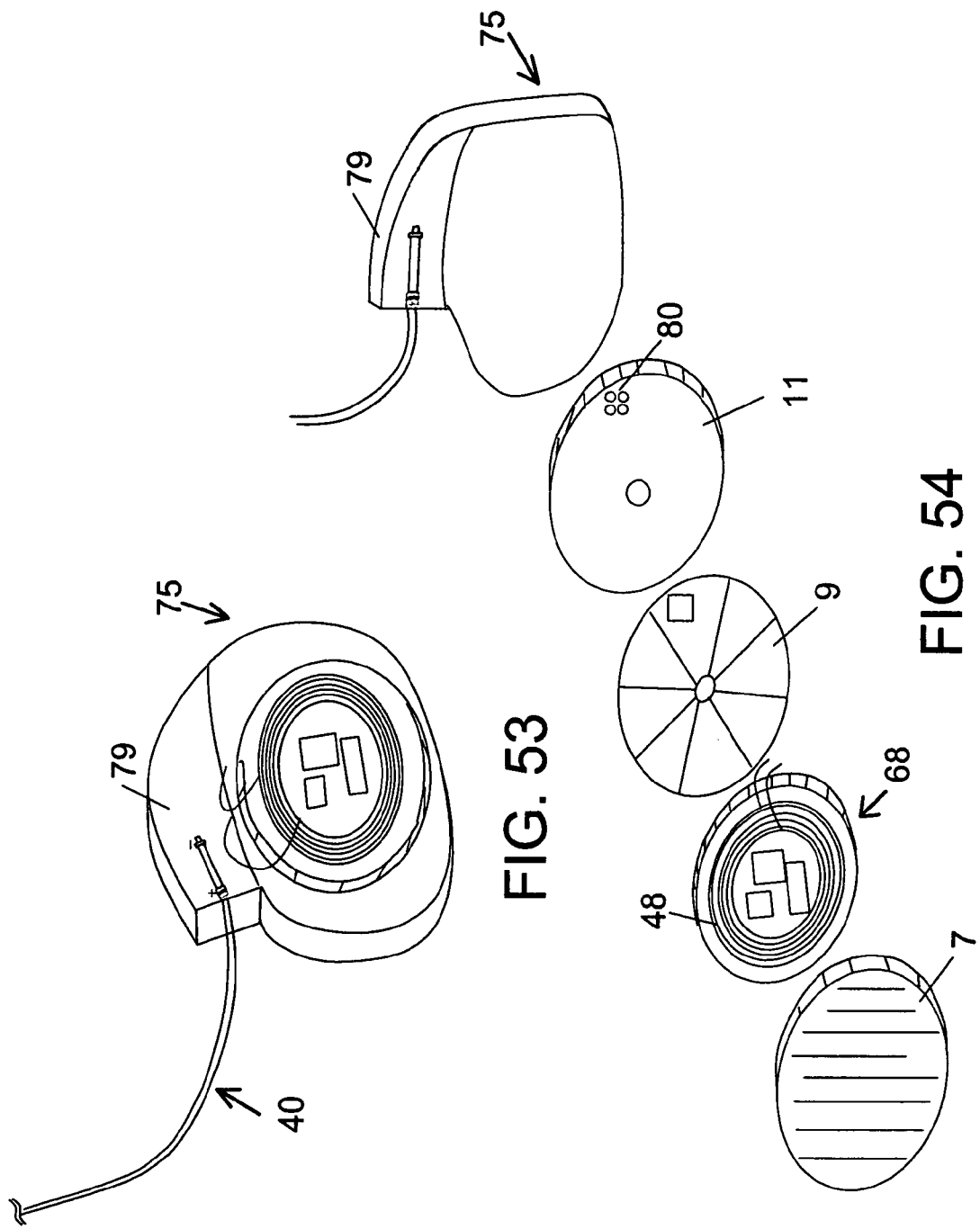

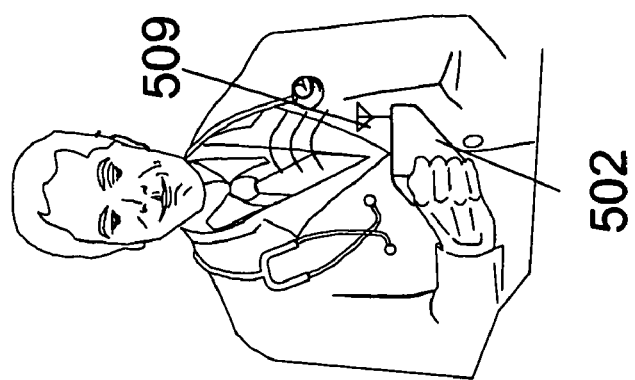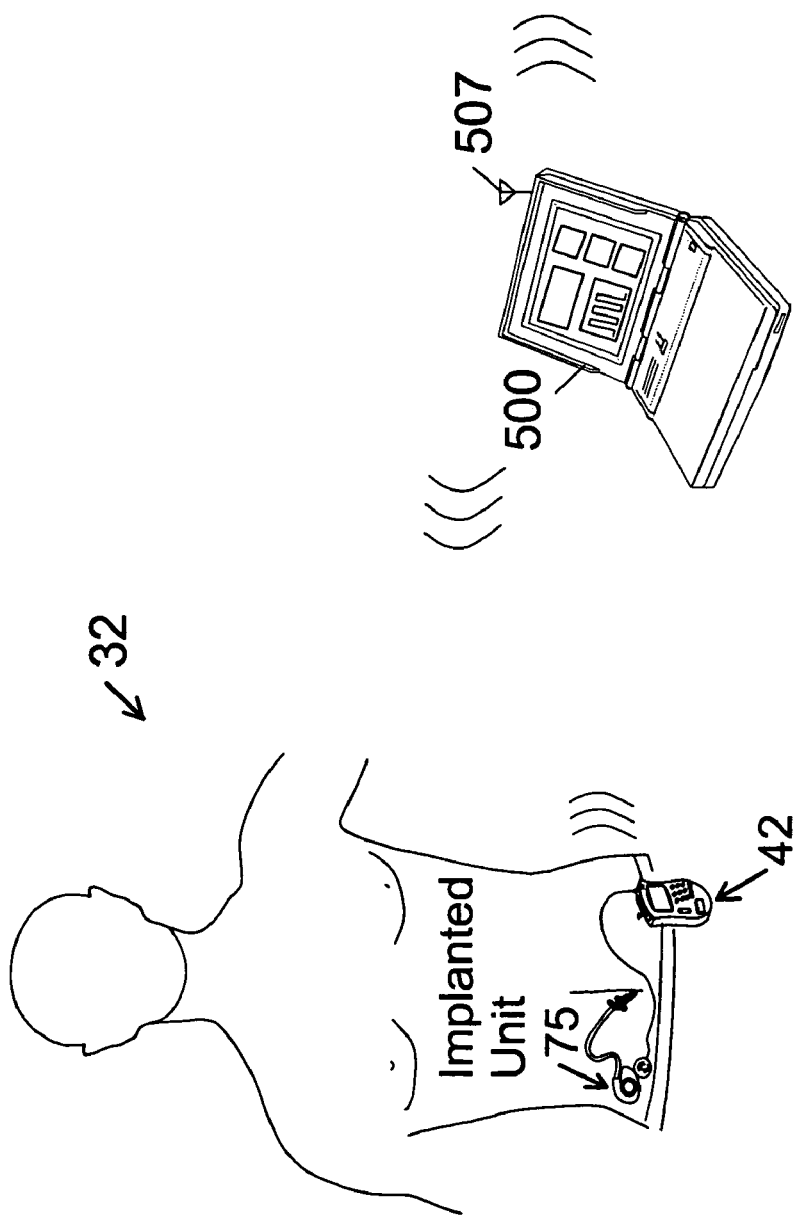
FIG. 56

METHOD AND SYSTEM FOR PROVIDING PULSED ELECTRICAL STIMULATION TO PROVIDE THERAPY FOR ERECTILE/SEXUAL DYSFUNCTION, PROSTATITIS, PROSTATITIS PAIN, AND CHRONIC PELVIC PAIN

FIELD OF INVENTION

The present invention relates to neurostimulation, more specifically neurostimulation of selective nerves or nerve bundles to provide therapy for erectile/sexual dysfunction, prostatitis, prostatitis pain, and chronic pelvic pain.

BACKGROUND

This disclosure is directed to pulsed electrical stimulation of nerves or nerve bundle in the sacral or pelvic region, or branches of such nerves or portion thereof, to provide therapy for erectile/sexual dysfunction, prostatitis, pain originating from prostate pathology, and chronic pelvic pain. The method and system of this invention comprises both implantable and external components. The nerve stimulation may be to different nerves in the sacral and/or pelvic regions of the body. To provide therapy for erectile dysfunction, the selective neurostimulation is to cavernous nerve or pudendal nerve or its branches or portion thereof. To provide therapy for prostatitis or chronic pelvic pain, the selective neurostimulation is provided to one or more of the pudendal nerve or its branches or portion thereof, the prostatic plexus or its branches or portions thereof, or the sacral splanchnic nerve or its branches or portions thereof.

General anatomy of the sacral region is shown in conjunction with FIG. 1. The relation of sciatic nerves 24 and pudendal nerve 20 in relation to sacral region is also shown in FIG. 1. There are five pairs of sacral nerves in the body. A more detailed anatomy of the five sacral nerves, their branches including the pudendal nerve is depicted in FIG. 2.

FIG. 3 and FIG. 4 show more details of the relevant anatomy. The male sexual organ (FIG. 4) and the innervation to the penis via cavernous nerve 28 is shown in FIG. 3 in more detail. Despite the obvious structural differences between the female and male reproductive organs, their neural regulation is surprisingly similar. Sexual arousal of adult men and women can result from erotic psychological and sensory stimuli, and from direct tactile stimulation of the external sex organs. A full sexual response cycle consists of arousal followed by plateau, orgasm, and resolution phases. Although the duration of each phase can vary widely, the physiological changes associated with each one are relatively consistent. Neural control of the sexual response comes in part from the cerebral cortex but the spinal cord coordinates this brain activity with sensory information from the genitals and generates the critical outputs that mediate the sexual responses of the genital structures.

The major external and internal sex organs are depicted in FIG. 5. Sexual arousal causes certain parts of the external genitals of both women and men to become engorged with blood, and thus to swell. In women, these structures include the labia and the clitoris; in men, it is primarily the penis. The external genitals are densely innervated by mechanoreceptors, particularly within the clitoris and the glans of the penis. Adequate stimulation of these sensory endings can, by itself be enough to cause engorgement and erection. The evidence that engorgement can be generated by a simple spinal reflex is that most men who have suffered a complete transection of the spinal cord at the thoracic or lumbar level, can nevertheless generate an erection when their penis is mechanically stimulated. The mechanosensory pathways from the genitals are components of the somatosensory system, and their anatomy follows the usual pattern: Axons from mechanoreceptors in the penis and clitoris collect in the dorsal roots of the sacral spinal cord (FIG. 5). They then send branches into the dorsal horns of the cord, and into the dorsal columns, through which they project toward the brain.

Engorgement and erection are controlled primarily be axons of the parasympathetic division of the autonomic nervous system (ANS). Within the sacral spinal cord, the parasympathetic neurons can be excited by either mechanosensory activity from the genitals (which can directly trigger reflexive erection), or by axons descending from the brain (which account for responses mediated by more cerebral stimuli). Engorgement of the clitoris and penis depend on dramatic changes in blood flow. Parasympathetic nerve endings are thought to release a potent combination of acetylcholine, vasoactive intestinal polypeptide (VIP), and nitric oxide (NO) directly into the erectile tissues. These neurotansmitters cause the relaxation of smooth muscle cells in the arteries and the spongy substance of the clitoris and penis. The usually flaccid arteries then become filled with blood, thereby distending the organs. (Sildenafil, a drug with the trade name Viagra, is a treatment for erectile dysfunction that works by enhancing the effects of NO). As the penis becomes longer and thicker, the spongy internal tissues swell against two thick elastic outer covering of connective tissue that give the erect penis its stiffness. In order to keep the organs sliding easily during copulation throughout the plateau phase, parasympathetic activity also stimulates the secretion of lubricating fluids from the woman's vaginal wall and from the man's bulbourethral gland.

Completing the sexual response cycle requires activity from the sympathetic division of the autonomic nervous system (ANS). As sensory axons, particularly from the penis or clitoris, become highly active, they together with activity descending from the brain, excite sympathetic neurons in the thoracic and lumbar segments of the spinal cord. In men, the sympathetic efferent axons then trigger the process of emission. Finally during ejaculation, a series of coordinated muscular contractions expel the semen from the urethra, and this is usually coincident with the intense sensations of orgasm. In women, stimulation adequate to trigger orgasm probably also activates the sympathetic system. Sympathetic outflow causes the outer vaginal wall to thicken and, during orgasm itself, triggers a series of strong muscular contractions. Following an orgasm, some time must pass before another orgasm can be triggered in men. The orgasmic experience of women tends to be considerably more variable in frequency and intensity. The resolution phase, which ends the sexual response cycle, includes a draining of blood from the external genitals through veins, and a loss of erection and other signs and sensations of sexual excitement.

Medical studies have shown that electrical stimulation of the cavernous nerve provides treatment for erectile dysfunction in humans. FIG. 6 depicts the location of cavernous nerve 28 at a point convenient for placing electrodes for neurostimulation. For implanting a system for erectile dysfunction, an incision is made for exposing the nerve tissue. As depicted in FIG. 7, the cavernous nerve 28 is exposed, and the distal portion of the lead is placed in the tissue, with electrodes in contact with the nerve tissue to be stimulated. The terminal portion of the lead is tunneled subcutaneously to a site where the pulse generator means is implanted, which is usually in the abdominal area. The tissues are surgically closed in layers, and stimulation can be applied after the tissues are healed from the surgery.

In one aspect of the invention, the pulsed electrical stimulation is applied to provide therapy for, or alleviating the symptoms of prostatitus and chronic pelvic pain. For providing such therapy, the electrodes are implanted on, or adjacent to one or more of the pudendal nerve or its branches or portions thereof, or the prostatic plexus or its branches or portions thereof, or the hypogastric nerve or its branches or portions thereof. Detailed anatomy of this region is shown in conjunction with FIGS. 8A, and 8B, 8C. The placement of electrodes to provide such therapy is also shown in conjunction with FIGS. 8B and 8C, and can be at a convenient location on one or more sites of the sacral, inferior hypogastric or superior hypogastric plexus or their branches or portions thereof.

Pulsed electrical stimulation induces nerve impulses in the form of action potentials in the nerve fibers. Shown in conjunction with FIG. 9, the information in the nervous system is coded by frequency of firing rather than the size of the individual action potentials. The bottom portion of FIG. 9 shows a train of action potentials 7. Shown in conjunction with FIG. 10, the rate of action potential generation depends on the magnitude of the depolarizing current. Thus, the firing frequency of action potentials reflects the magnitude of the depolarizing current. This is one way that stimulation intensity is encoded in the nervous system, as shown in FIG. 10. Although firing frequency increases with the amount of depolarizing current, there is a limit to the rate at which neurons can generate action potentials, depending on the absolute refractory period and the relative refractory period.

In the method and system of this invention, pulsed electrical stimulation is provided using both implanted and external components. The pulse generator may be implanted in the body, or may be external to the body. In one aspect the external components may be networked over a wide area network, for remote interrogation and remote programming of stimulation parameters.

PRIOR ART

U.S. patent application No. 2004/0049240 A1 (Gerber et al.) is directed to electrical and/or magnetic stimulation therapy for providing pain relief to patients suffering from prostatitis, protatalgia, or protatodynia.

U.S. Pat. No. 6,650,943 B1 (Whitehurst et al.) is generally directed to the use of a leadless microstimulator to provide nerve stimulation as a therapy for erectile dysfunction and other sexual dysfunction. The microstimulator of this patent having a diameter of approximately 4 mm and having a length of approximately 20-30 mm.

U.S. Pat. No. 6,169,924 B1 (Meloy et al.) is generally directed to spinal cord stimulation to treat orgasmic dysfunction.

U.S. patent application No. 2004/0073268A1 (Zappala) mearly discloses placement of a lead via the dorsal vein of the phallus, for stimulation device for managing erectile dysfunction.

U.S. Pat. No. 5,938,584 (Ardito) is generally directed to stimulating the cavernous nerve with two pairs of bipolar leads and an implanted pulse generator.

U.S. patent application No. 2003/0236557 A1 (Whitehurst et al.) is generally directed to unidirectional propagation of action potentials with cavernous nerve stimulation using microstimulators.

OTHER PUBLICATIONS

Shafik A., "Extrapelvic cavernous nerve stimulation in erectile dysfunction. Human study, *Andrologia* 28, pp. 151-156 (1996).

Lue T. F. et al., "Electrostimulation and penile erection", *Urol. Int.* 40: pp. 60-64 (1985).

Martinez-Pineiro L. et al., "Rat model for the study of penile erection, pharmacologic and electrical-stimulation parameters", *Eur. urol.* 25: pp. 62-70 (1994).

Shafik A. et al., "Magnetic stimulation of the cavernous nerve for the treatment of erectile dysfunction in humans", *Int. J. Impot. Res.* 12(3) pp. 137-142 (2000). [Based on abstract of the article]

Shafik A. et al., "Perineal nerve stimulation: Role in penile erection", *Int. J. Impot. Res.* 9 pp. 11-16 (1997). [Based on abstract of the article]

SUMMARY OF THE INVENTION

The present invention has certain objects. That is, various embodiments of the present invention provide solution to one or more problems exiting in the prior art, including the problems of: a) testing the effectiveness of the therapy with a device and then implanting a different system to provide therapy; b) patient requires periodic surgeries to replace systems at the end of battery-life, (typical battery life is 3-6 years); c) patient is not able to easily change between an implanted, external, or integrated system; d) patient is unable to make use of 'cumulative effect' of therapy to reduce/eliminate of disorders in addition to just 'event' based therapy due to limited battery life of exiting systems; e) frequent patients visits to clinics/physician office to monitor the device; f) titration of therapy is a long and drawn out.

The method and system of the current invention provides pulsed electrical stimulation to provide therapy for erectile/sexual dysfunction and prostatitus/chronic pain. The stimulation is to cavernous nerve or its branches or portion thereof, to provide therapy for erectile/sexual dysfunction. To provide therapy for prostatitis chronic pelvic pain, the stimulation is to pudendal nerve or its branches or portion thereof, the prostatic plexus or its branches or portion thereof, or the sacral splanchnic nerve or its branches or portion thereof. The method and system comprises both implantable and external components. The power source may also be external or implanted in the body. The system to provide selective stimulation may be selected from a group consisting of:

a) an implanted stimulus-receiver with an external stimulator;

b) an implanted stimulus-receiver comprising a high value capacitor for storing charge, used in conjunction with an external stimulator;

c) a programmer-less implantable pulse generator (IPG) which is operable with a magnet;

d) a programmable implantable pulse generator (IPG);

e) a combination implantable device comprising both a stimulus-receiver and a programmable IPG; and f) an IPG comprising a rechargeable battery.

In one aspect of the invention, the selective stimulation site on one or more of the sacral plexus or its branches, inferior hypogastric plexus or its branches, superior hypogastric plexus or its branches in a patient may be anywhere along the length of nerve fibers.

In another aspect of the invention, the stimulation may be unidirectional.

In another aspect of the invention, the external components such as the external stimulator or programmer comprise telemetry means adapted to be networked, for remote interrogation or remote programming of the device.

In another aspect of the invention, the pulse generator may be implanted in the body.

In another aspect of the invention, the implanted pulse generator is adapted to be re-chargable via an external power source.

In another aspect of the invention, the implanted lead body may be made of a material selected from the group consisting of polyurethane, silicone, and silicone with polytetrafluoroethylene.

In another aspect of the invention, the implanted lead comprises at least one electrode selected from the group consisting of platinum, platinum/iridium alloy, platinum/iridium alloy coated with titanium nitride, and carbon.

In yet another aspect of the invention, the implanted lead comprises at least one electrode selected from the group consisting of spiral electrodes, cuff electrodes, steroid eluting electrodes, wrap-around electrodes, and hydrogel electrodes.

Various other features, objects and advantages of the invention will be made apparent from the following description taken together with the drawings.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIGS. 8A-8C show detailed anatomy of the nerves in the sacral and pelvic regions.
FIG. 35 is a circuit diagram of a voltage doubler.
FIG. 38 is a diagram showing different types of nerve fibers and their properties.
FIGS. 40A and 40B are diagrams showing communication of programmer with the implanted stimulator.
FIGS. 41A and 41B show diagrammatically encoding and decoding of programming pulses.

FIG. 53 shows a picture of the combination implantable stimulator.

FIG. 54 shows assembly features of the implantable portion of the system.

FIG. 56 depicts remote monitoring of stimulation devices.

DETAILED DESCRIPTION OF THE INVENTION

Figure 1:
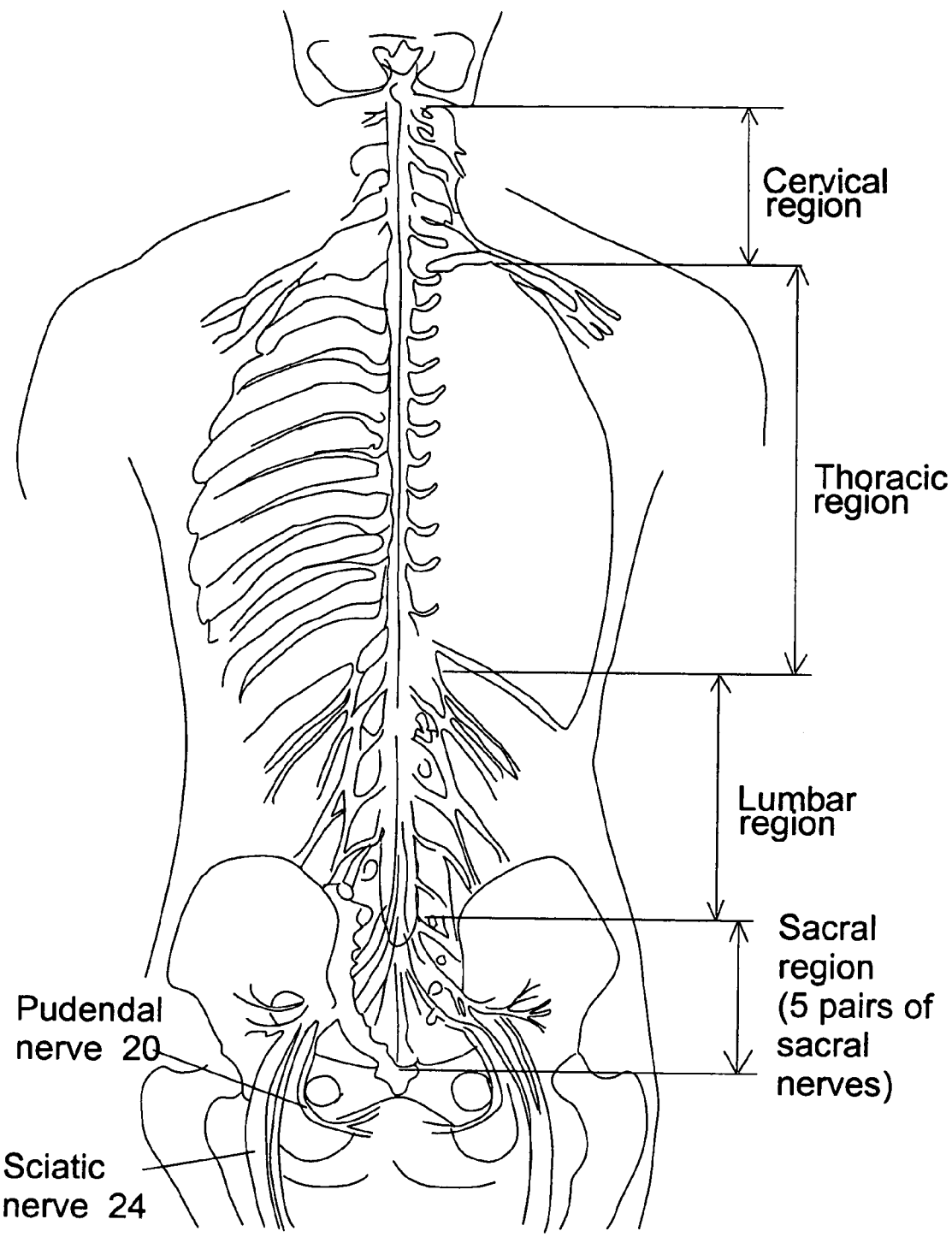
FIG. 1 is a diagram depicting five pairs of sacral nerves.
Figure 2:
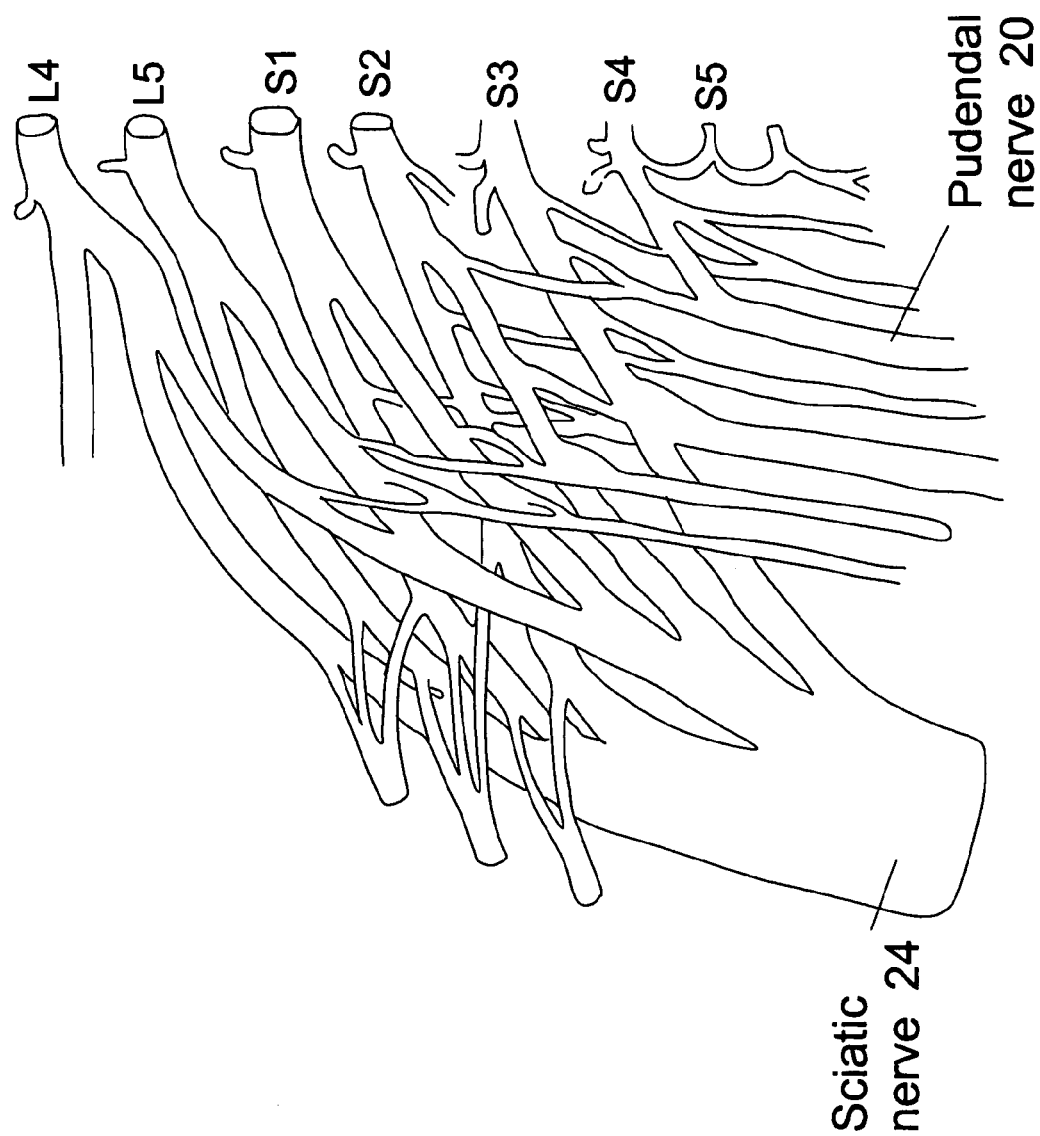
FIG. 2 is a diagram depicting branches of sacral nerves.
Figure 3:
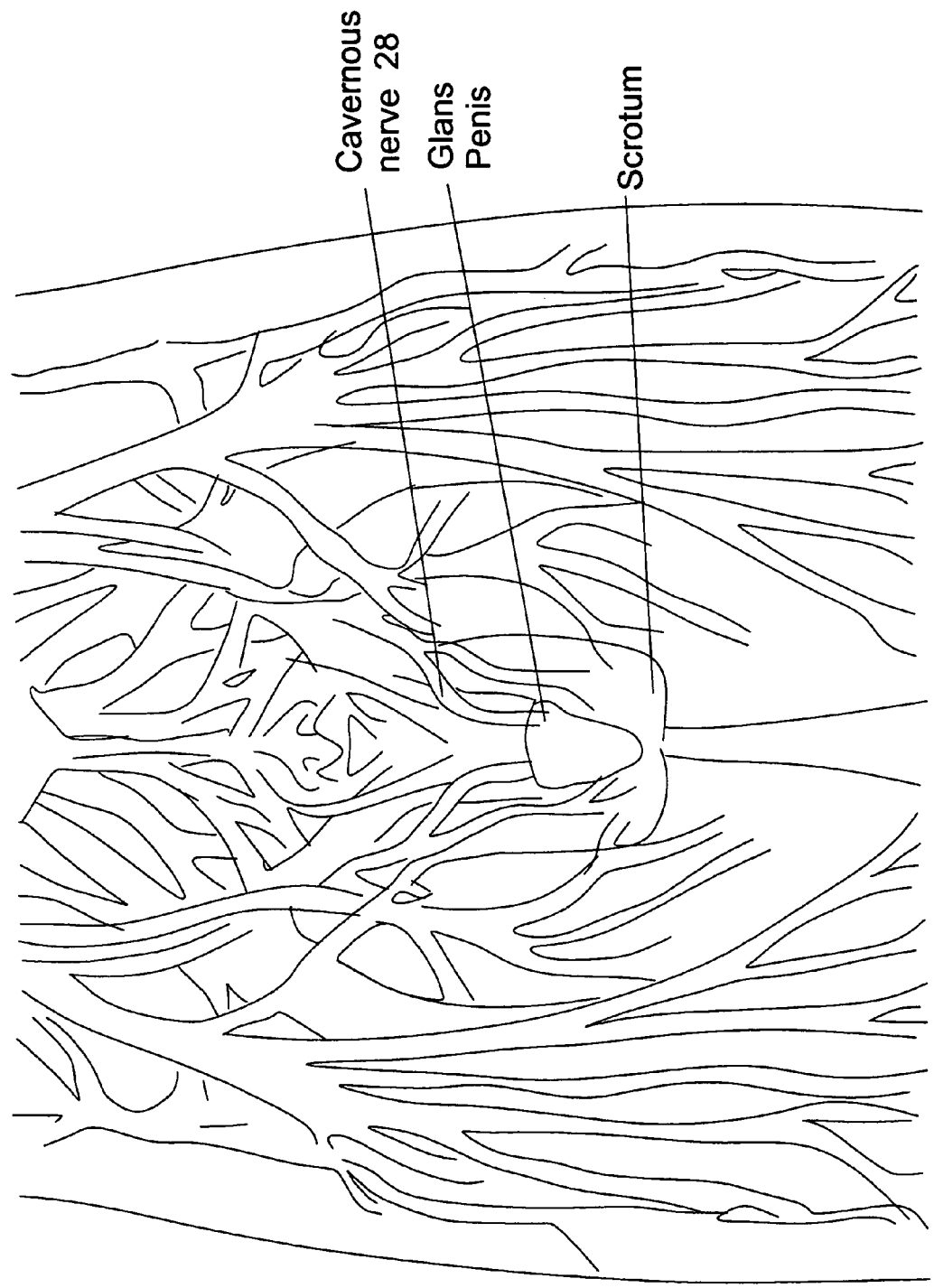
FIG. 3 is a diagram depicting innervation of the cavernous nerves.
Figure 4:
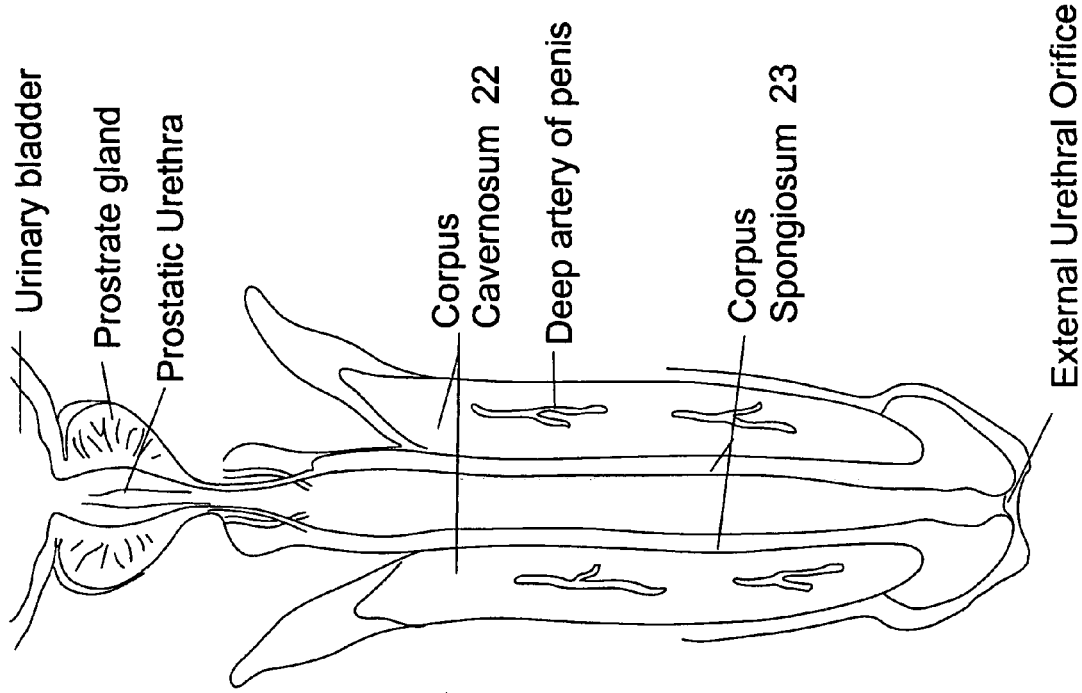
FIG. 4 is a diagram showing the anatomy of the penis.
Figure 5:
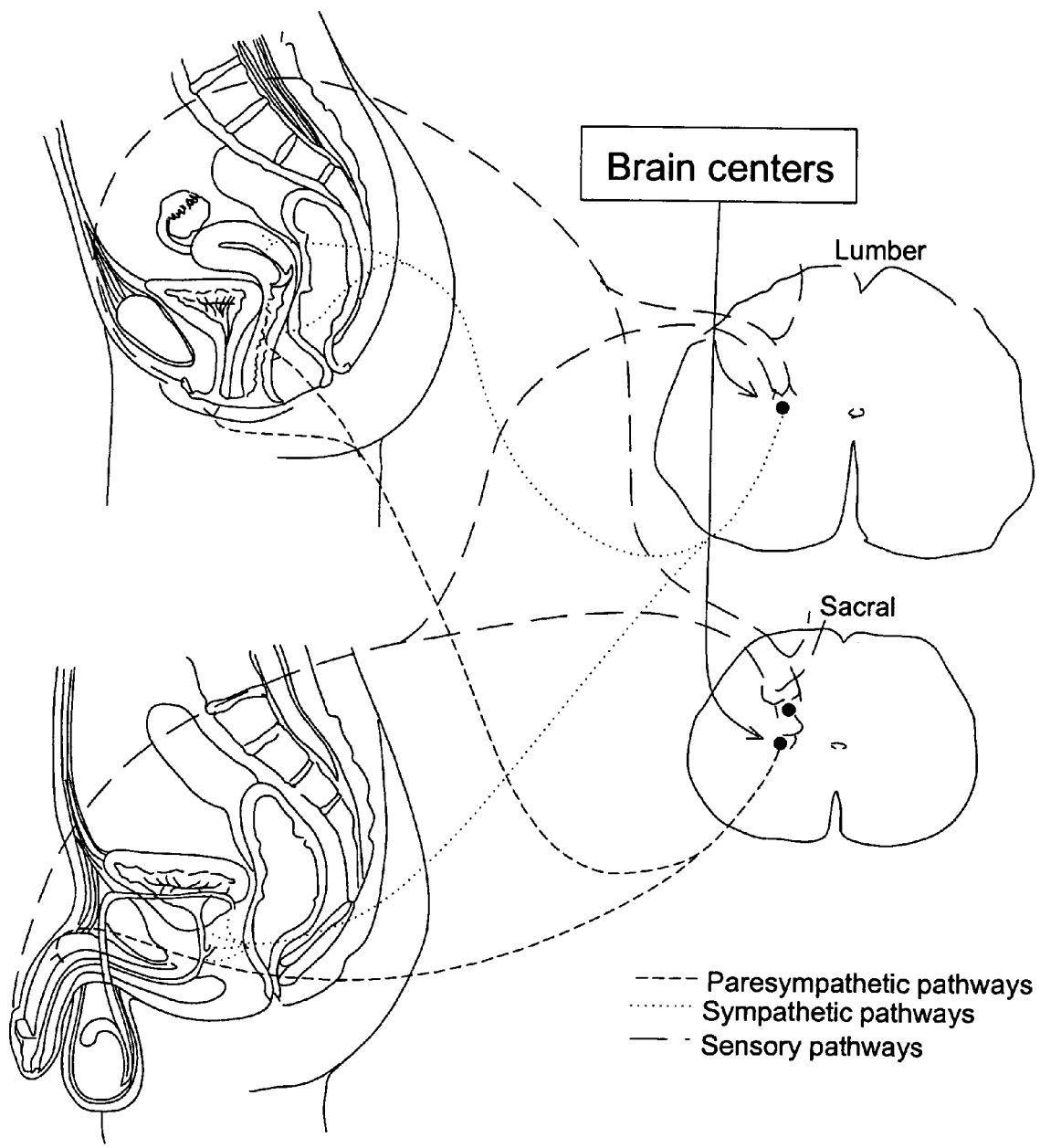
FIG. 5 is a diagram depicting innervation of male and female sexual organs.
Figure 6:
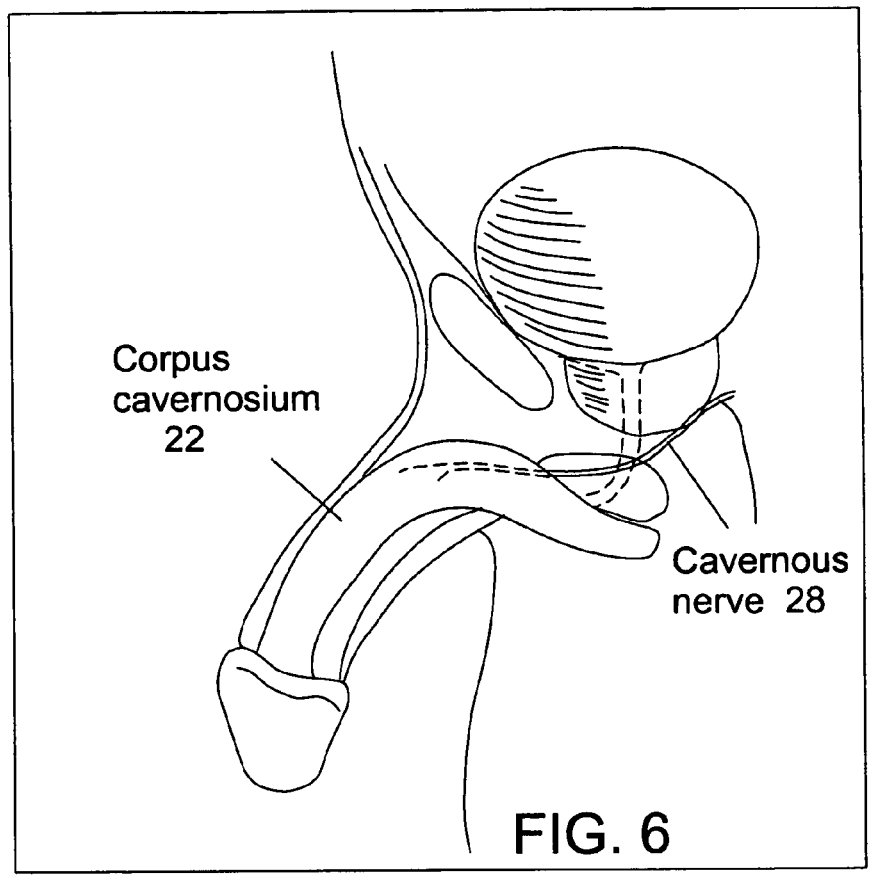
FIG. 6 is a diagram showing the course of the cavernous nerve.
Figure 7:
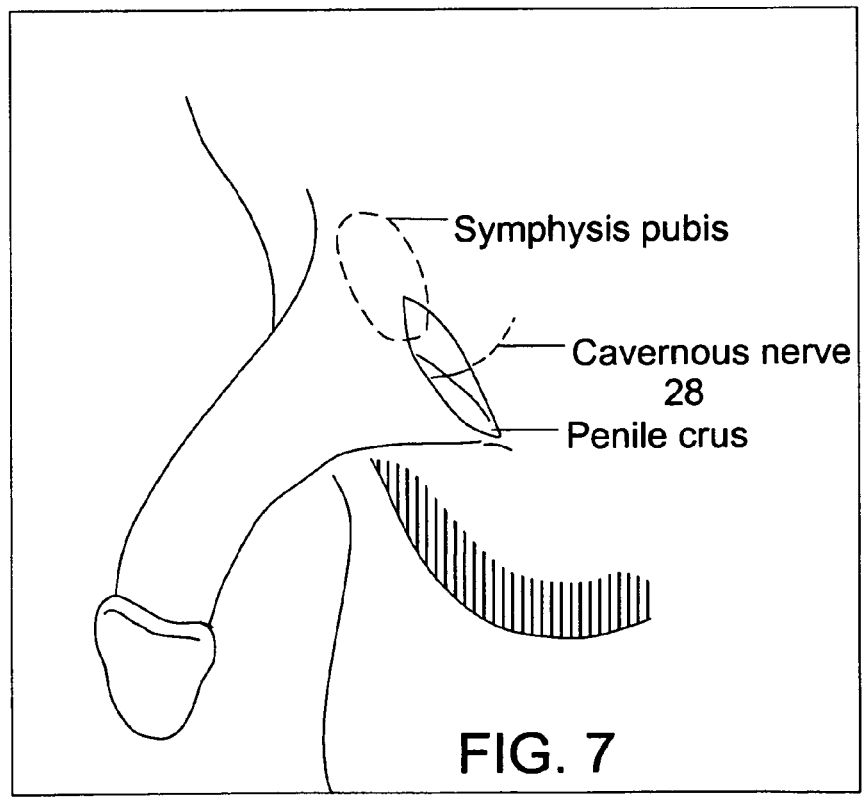
FIG. 7 is a diagram showing a site for incision, to expose the cavernous nerve.
Figure 8A:
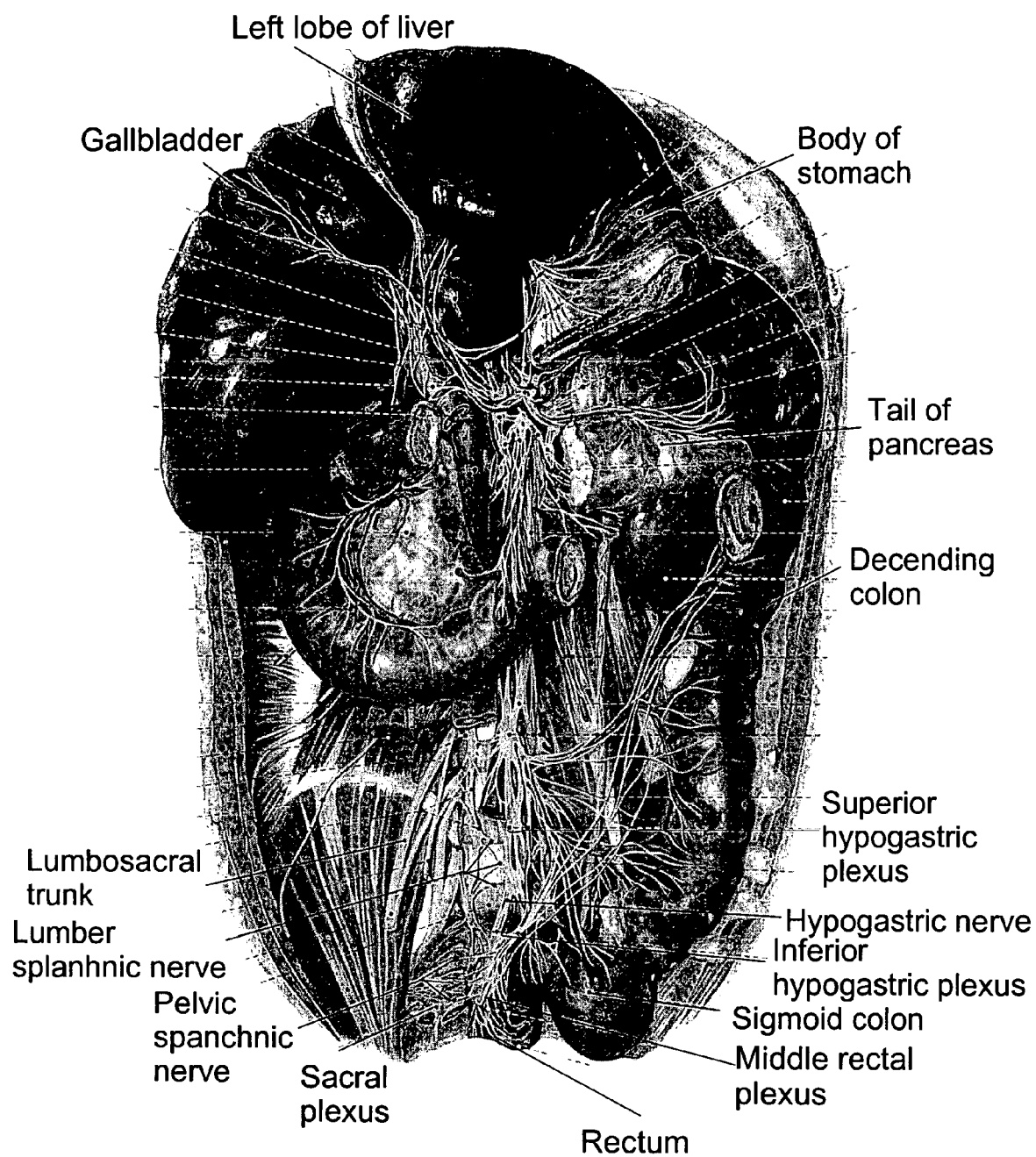
Figure 8C:
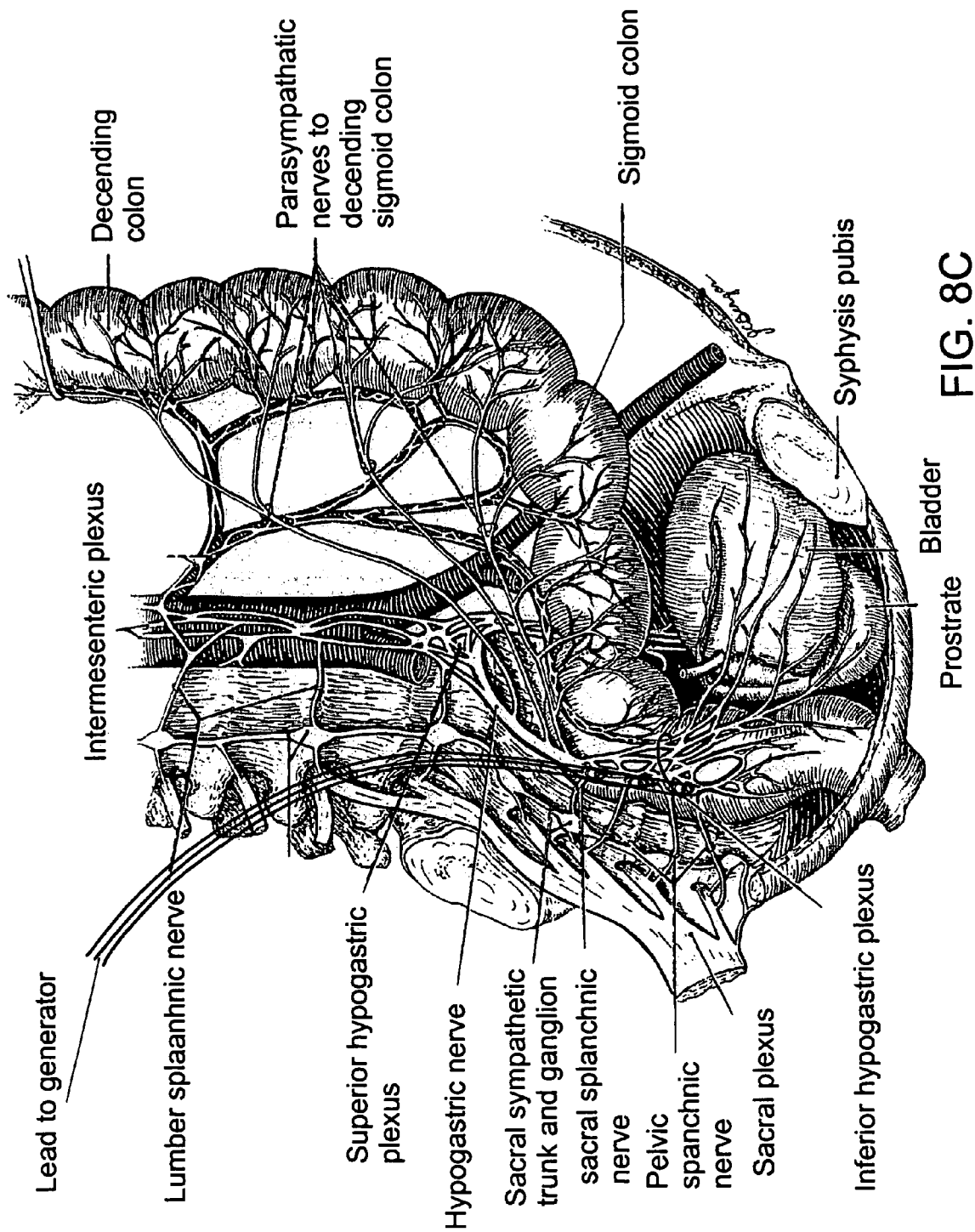
Figure 9:
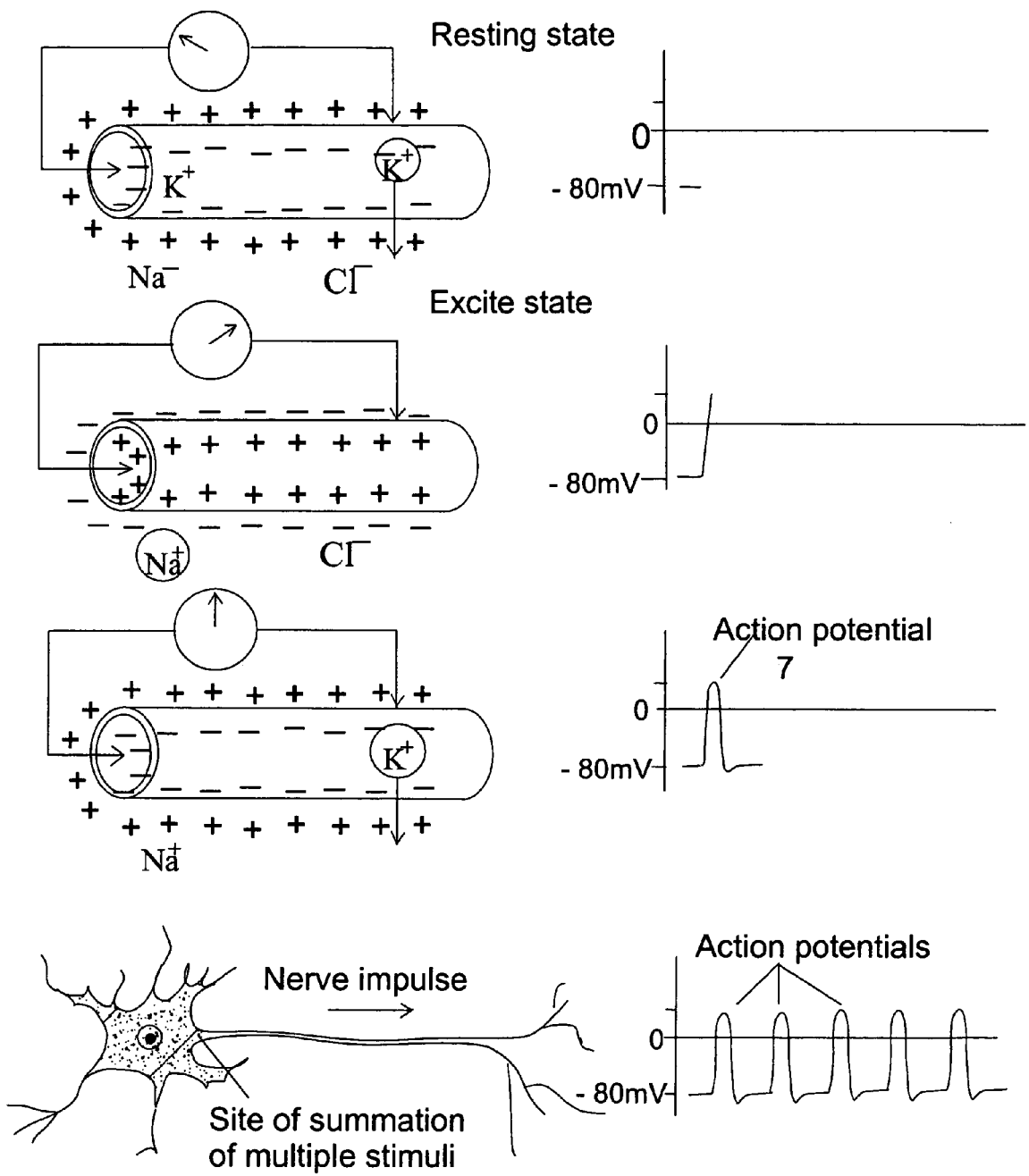
FIG. 9 is an illustration showing a train of action potentials.
Figure 10:
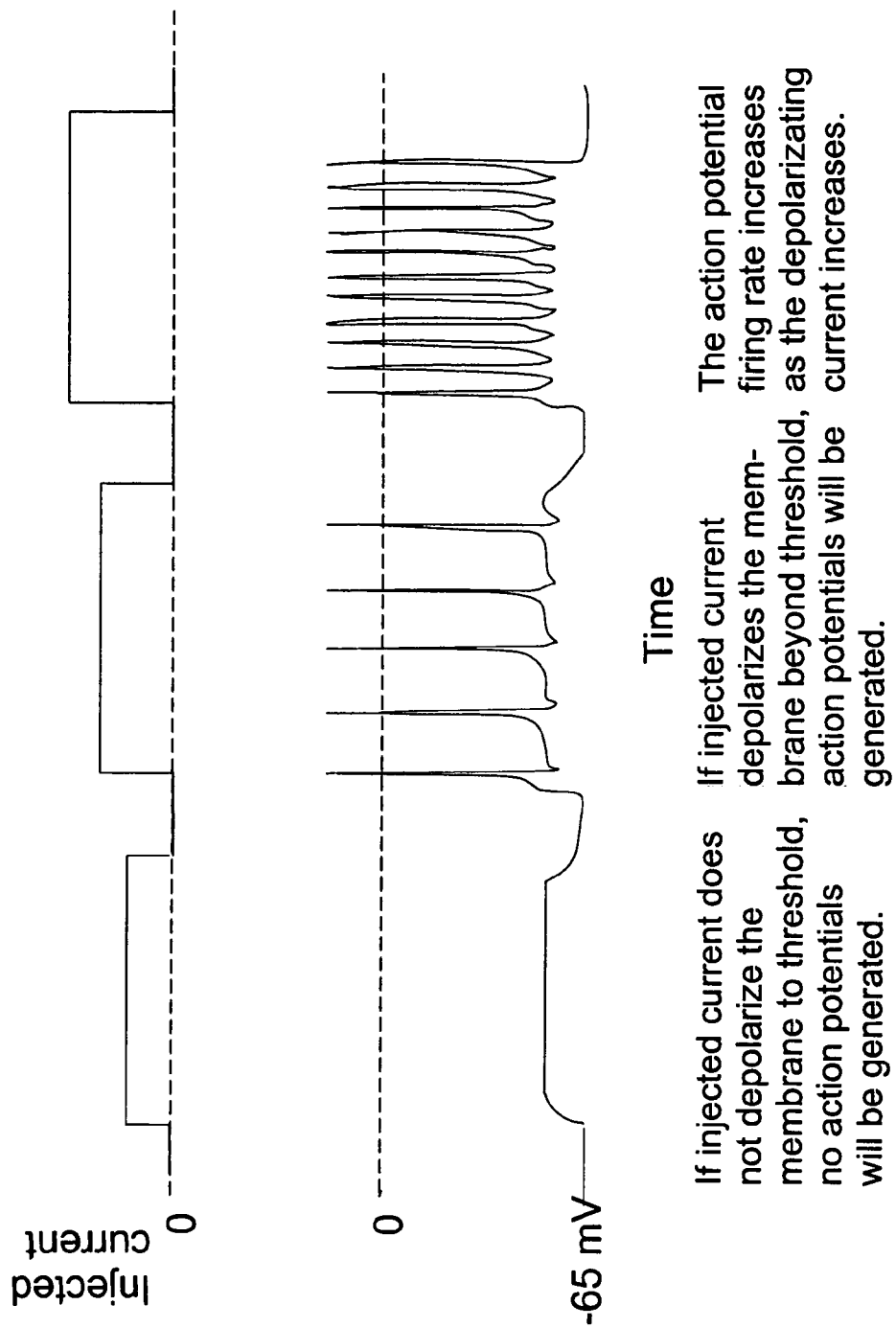
FIG. 10 is a diagram depicting action potentials in response to changing depolarization currents.

The method and system of the current invention delivers pulsed electrical stimulation, to provide therapy for erectile/sexual dysfunction and prostatitus/chronic pelvic pain. The electrical stimulation is delivered to one or more of the cavernous (or pudendal) nerve(s) to provide therapy for erectile/sexual dysfunction. To provide therapy for prostatitis/chronic pelvic pain, the electrical stimulation is delivered to one or more of the pudendal nerve or its branches, the prostatic plexus or its branches, or the sacral splanchnic nerve or its branches. The method and system comprises both implantable and external components.

For implantation of the system, an incision is made for exposing the nerve tissue to be stimulated, and the distal portion of the lead is implanted in the tissue with electrodes in contact with the nerve tissue to be stimulated. The terminal portion of the lead is tunneled subcutaneously to a site where the pulse generator means is implanted, which is usually in the abdominal area. The pulse generator means is connected to the proximal end 44 of the lead, placed in a subcutaneous pocket, and the tissues are surgically closed in layers. Stimulation therapy can be applied after the tissues are healed from the surgery.

In the method and system of this invention, the pulse generator means may be implanted in the body or may be external to the body. Also, the power source may be external, implantable, or a combination device.

In the method of this invention, a simple and cheap pulse generator may be used to test a patient's response to neuromodulation therapy. As one example only, an implanted stimulus-receiver in conjunction with an external stimulator may be used initially to test patient's response. If the patient responds well, then at a later time, the pulse generator may be exchanged for a more elaborate implanted pulse generator (IPG) model, keeping the same lead. Some examples of stimulation and power sources that may be used interchangeably with the same lead for the practice of this invention, and disclosed in this Application, include:

a) an implanted stimulus-receiver with an external stimulator;

b) an implanted stimulus-receiver comprising a high value capacitor for storing charge, used in conjunction with an external stimulator;

c) a programmer-less implantable pulse generator (IPG) which is operable with a magnet;

d) a programmable implantable pulse generator (IPG);

e) a combination implantable device comprising both a stimulus-receiver and a programmable IPG; and f) an IPG comprising a rechargeable battery.

As another example, a cheap programmer-less IPG may be implanted initially to test the efficacy of neuromodulation therapy in the patient. If the patient responds well, the simple programmer-less IPG may be replaced with a higher functionality (and more expensive) version of IPG at a future time.

Also as disclosed later, the external components such as a programmer, or external pulse generator, may comprise a telemetry module for remote communication over the internet. This would provide means of remotely interrogating the device, or loading or activating new programs from a remote location.

Even though the pulse generator means are interchangeble, the lead is implanted only once. The proximal (or terminal) portion of the lead is plugged into the pulse generator means. The distal portion of the lead comprises two, or three, or four electrodes for delivering electrical stimulation. As described earlier in the background, the pulsed electrical stimulation may be to one of several nerves e.g. the cavernous nerve, the pudendal nerve etc. For the purpose of describing the system, the stimulation site is referred to as simply "nerve tissue 54". It is to be understood that the nerve tissue 54 refers to the appropriate nerve or nerve plexus, or branches to be stimulated for the particular therapy to be delivered.

Implanted Stimulus-Receiver with an External Stimulator

Figure 11:
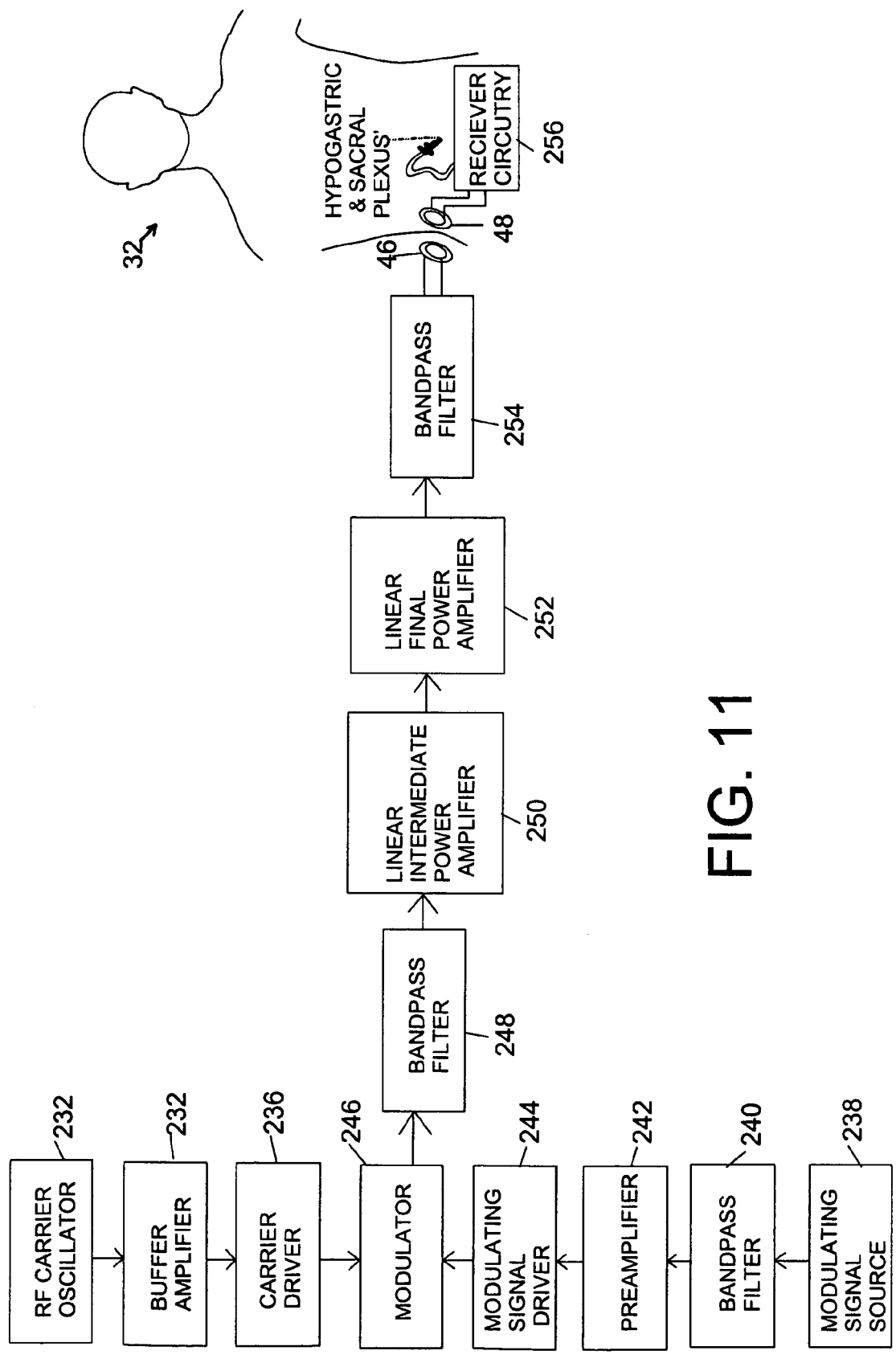
FIG. 11 is a simplified block diagram depicting supplying amplitude and pulse width modulated electromagnetic pulses to an implanted coil.

For an external power source, a passive implanted stimulus-receiver may be used. The appropriate stimulation of selected nerve fibers in the sacral and pelvic region, as performed by one embodiment of the method and system of this invention is shown schematically in FIG. 11, as a block diagram. A modulator 246 receives analog (sine wave) high frequency "carrier" signal and modulating signal. The modulating signal can be multilevel digital, binary, or even an analog signal. In this embodiment, mostly multilevel digital type i.e., pulse amplitude and pulse width modulated signals are used. The modulated signal is amplified 250, 252, conditioned 254, and transmitted via a primary coil 46 which is external to the body. Shown in conjunction with FIG. 12, a secondary coil 48 of an implanted stimulus-receiver, receives, demodulates, and delivers these pulses to the nerve tissue 54 via electrodes 61 and 62 (or a proximal pair). The receiver circuitry 256 is described later.

The carrier frequency is optimized. One preferred embodiment utilizes electrical signals of around 1 Mega-Hertz, even though other frequencies can be used. Low frequencies are generally not suitable because of energy requirements for longer wavelengths, whereas higher frequencies are absorbed by the tissues and are converted to heat, which again results in power losses.

Figure 12:
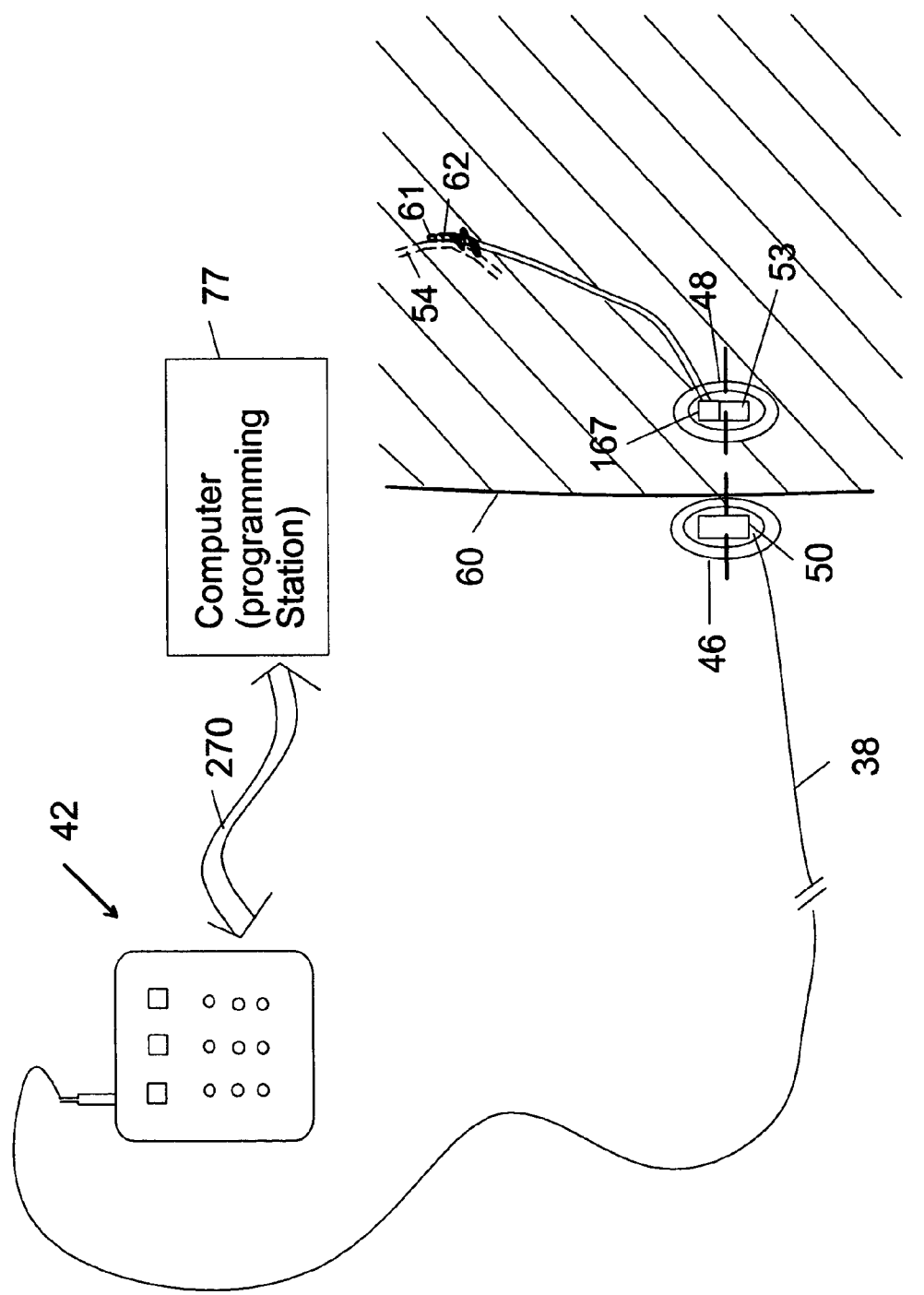
FIG. 12 shows coupling of the external stimulator and the implanted stimulus-receiver.

Also, shown in conjunction with FIG. 12, the primary (external) coil 46 of the external stimulator 42 is inductively coupled to the secondary (implanted) coil 48 of the implanted stimulus-receiver 34. The implantable stimulus-receiver has circuitry at the proximal end, and has stimulating electrodes at the distal end of the lead.

Figure 13:
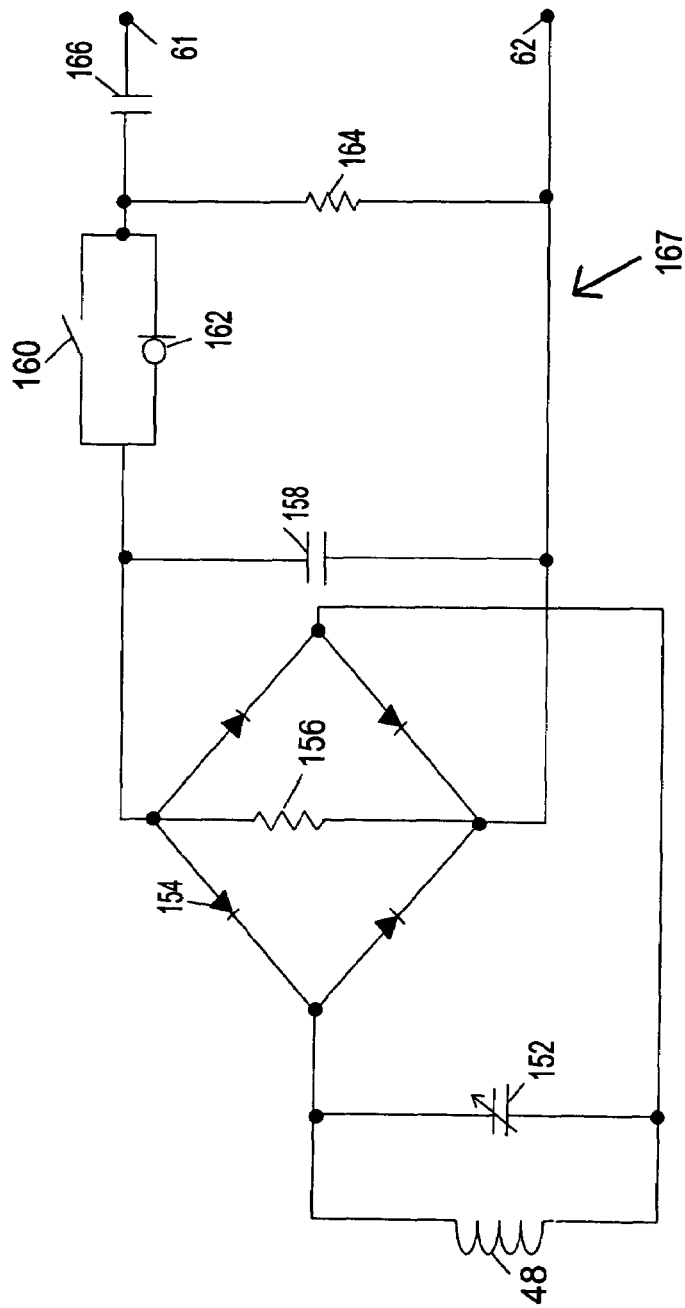
FIG. 13 is a schematic of the passive circuitry in the implanted lead-receiver.

The circuitry contained in the proximal end of the implantable stimulus-receiver 34 is shown schematically in FIG. 13, for one embodiment. In this embodiment, the circuit uses all passive components. Approximately 25 turn copper wire of 30 gauge, or comparable thickness, is used for the primary coil 46 and secondary coil 48. This wire is concentrically wound with the windings all in one plane. The frequency of the pulse-waveform delivered to the implanted coil 48 can vary, and so a variable capacitor 152 provides ability to tune secondary implanted circuit 167 to the signal from the primary coil 46. The pulse signal from secondary (implanted) coil 48 is rectified by the diode bridge 154 and frequency reduction obtained by capacitor 158 and resistor 164. The last component in line is capacitor 166, used for isolating the output signal from the electrode wire. The return path of signal from cathode 61 will be through anode 62 placed in proximity to the cathode 61 for "Bipolar" stimulation. In this embodiment bipolar mode of stimulation is used, however, the return path can be connected to the remote ground connection (case) of implantable circuit 167, providing for much larger intermediate tissue for "Unipolar" stimulation. The "Bipolar" stimulation offers localized stimulation of tissue compared to "Unipolar" stimulation and is therefore, preferred in this embodiment. Unipolar stimulation is more likely to stimulate skeletal muscle in addition to nerve stimulation. The implanted circuit 167 in this embodiment is passive, so a battery does not have to be implanted.

Figure 14A:
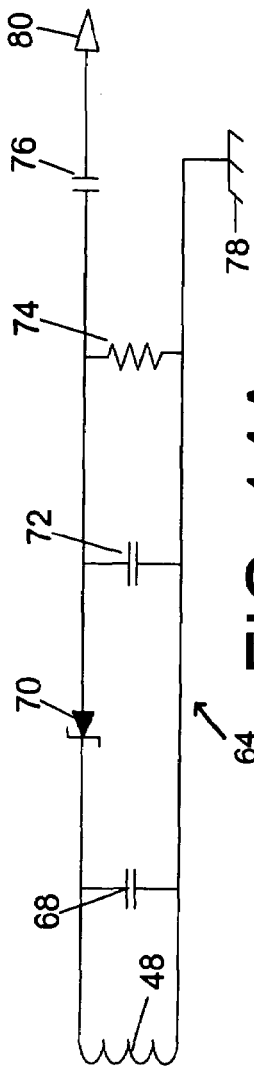
FIG. 14A is a schematic of an alternative embodiment of the implanted lead-receiver.
Figure 14B:
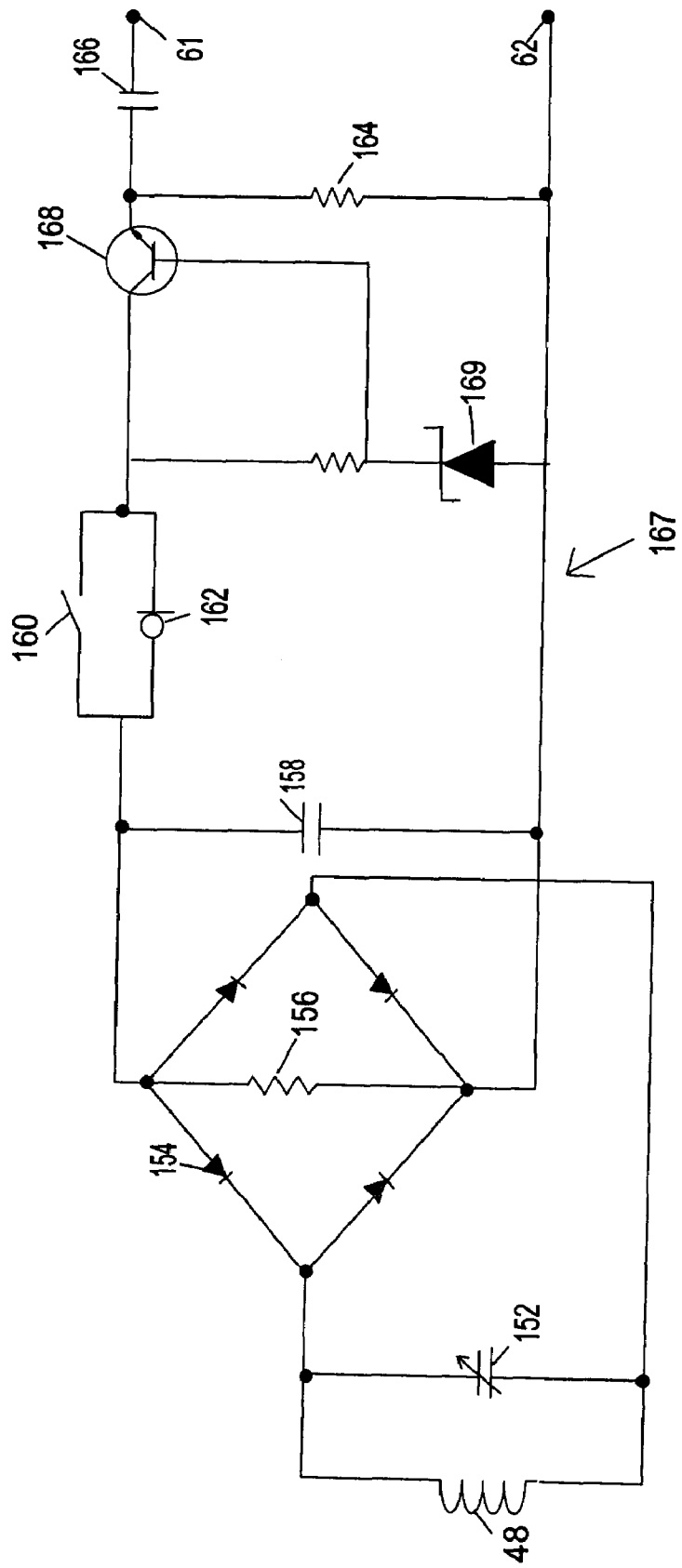
FIG. 14B is another alternative embodiment of the implanted lead-receiver.

The circuitry shown in FIGS. 14A and 14B can be used as an alternative for the implanted stimulus-receiver. The circuitry of FIG. 14A is a slightly simpler version, and circuitry of FIG. 14B contains a conventional NPN transistor 168 connected in an emitter-follower configuration.

For therapy to commence, the primary (external) coil 46 is placed on the skin 60 on top of the surgically implanted (secondary) coil 48. An adhesive tape may be placed on the skin 60 and external coil 46 such that the external coil 46, is taped to the skin 60. For efficient energy transfer to occur, it is important that the primary (external) and secondary (internal) coils 46,48 be positioned along the same axis and be optimally positioned relative to each other. In this embodiment, the external coil 46 may be connected to proximity sensing circuitry 50. The correct positioning of the external coil 46 with respect to the internal coil 48 is indicated by turning "on" of a light emitting diode (LED) on the external stimulator 42.

Optimal placement of the external (primary) coil 46 is done with the aid of proximity sensing circuitry incorporated in the system, in this embodiment. Proximity sensing occurs utilizing a combination of external and implantable components. The implanted components contains a relatively small magnet composed of materials that exhibit Giant Magneto-Resistor (GMR) characteristics such as Samarium-cobalt, a coil, and passive circuitry. As was shown in conjunction with FIG. 12, the external coil 46 and proximity sensor circuitry 50 are rigidly connected in a convenient enclosure which is attached externally on the skin. The sensors measure the direction of the field applied from the magnet to sensors within a specific range of field strength magnitude. The dual sensors exhibit accurate sensing under relatively large separation between the sensor and the target magnet. As the external coil 46 placement is "fine tuned", the condition where the external (primary) coil 46 comes in optimal position, i.e. is located adjacent and parallel to the subcutaneous (secondary) coil 48, along its axis, is recorded and indicated by a light emitting diode (LED) on the external stimulator 42.

Figure 15:
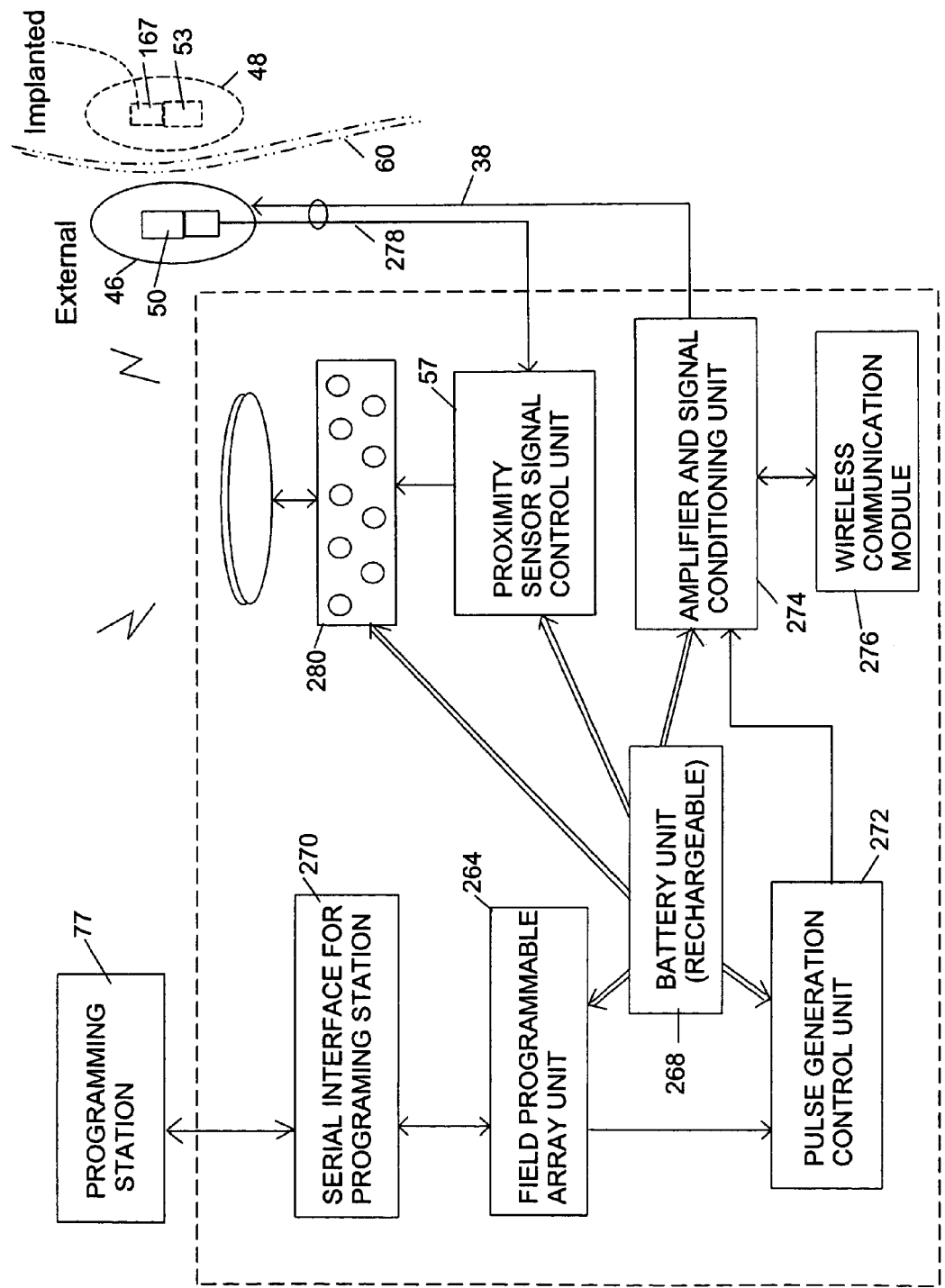
FIG. 15 is a top-level block diagram of the external stimulator and proximity sensing mechanism.

FIG. 15 shows an overall block diagram of the components of the external stimulator and the proximity sensing mechanism. The proximity sensing components are the primary (external) coil 46, supercutaneous (external) proximity sensors 648, 652 (FIG. 16) in the proximity sensor circuit unit 50, and a subcutaneous secondary coil 48 with a Giant Magneto Resister (GMR) magnet 53 associated with the proximity sensor unit. The proximity sensor circuit 50 provides a measure of the position of the secondary implanted coil 48. The signal output from proximity sensor circuit 50 is derived from the relative location of the primary and secondary coils 46, 48. The sub-assemblies consist of the coil and the associated electronic components, that are rigidly connected to the coil.

The proximity sensors (external) contained in the proximity sensor circuit 50 detect the presence of a GMR magnet 53, composed of Samarium Cobalt, that is rigidly attached to the implanted secondary coil 48. The proximity sensors, are mounted externally as a rigid assembly and sense the actual separation between the coils, also known as the proximity distance. In the event that the distance exceeds the system limit, the signal drops off and an alarm sounds to indicate failure of the production of adequate signal in the secondary implanted circuit 167, as applied in this embodiment of the device. This signal is provided to the location indicator LED 280.

Figure 16:
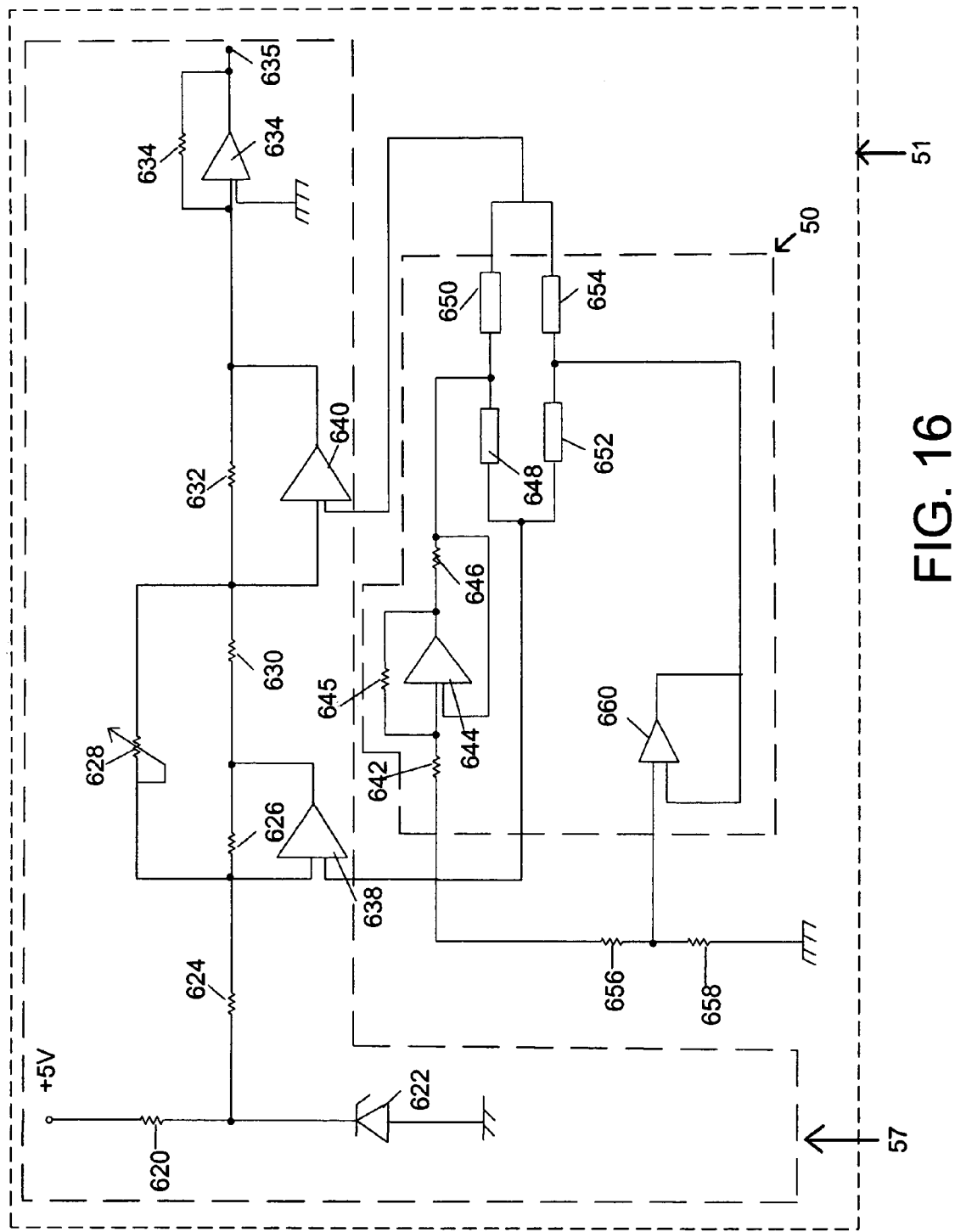
FIG. 16 is a diagram showing the proximity sensor circuitry.

FIG. 16 shows the circuit used to drive the proximity sensors 648, 652 of the proximity sensor circuit 50. The two proximity sensors 648, 652 obtain a proximity signal based on their position with respect to the implanted GMR magnet 53. This circuit also provides temperature compensation. The sensors 648, 652 are 'Giant Magneto Resistor' (GMR) type sensors packaged as proximity sensor unit 50. There are two components of the complete proximity sensor circuit. One component is mounted supercutaneously 50, and the other component, the proximity sensor signal control unit 57 is within the external stimulator 42. The resistance effect depends on the combination of the soft magnetic layer of magnet 53, where the change of direction of magnetization from external source can be large, and the hard magnetic layer, where the direction of magnetization remains unchanged. The resistance of this sensor 50 varies along a straight motion through the curvature of the magnetic field. A bridge differential voltage is suitably amplified and used as the proximity signal.

The Siemens GMR B6 (Siemens Corp., Special Components Inc., New Jersey) is used for this function in one embodiment. The maximum value of the peak-to-peak signal is observed as the external magnetic field becomes strong enough, at which point the resistance increases, resulting in the increase of the field-angle between the soft magnetic and hard magnetic material. The bridge voltage also increases. In this application, the two sensors 648, 652 are oriented orthogonal to each other.

The distance between the magnet 53 and sensor 50 is not relevant as long as the magnetic field is between 5 and 15 KA/m, and provides a range of distances between the sensors 648, 652 and the magnetic material 53. The GMR sensor registers the direction of the external magnetic field. A typical magnet to induce permanent magnetic field is approximately 15 by 8 by 5 mm$^3$, for this application and these components. The sensors 648, 652 are sensitive to temperature, such that the corresponding resistance drops as temperature increases. This effect is quite minimal until about 100° C. A full bridge circuit is used for temperature compensation, as shown in temperature compensation circuit 50 of FIG. 16. The sensors 648, 652 and a pair of resistors 650, 654 are shown as part of the bridge network for temperature compensation. It is also possible to use a full bridge network of two additional sensors in place of the resistors 650, 654.

The signal from either proximity sensor 648, 652 is rectangular if the surface of the magnetic material is normal to the sensor and is radial to the axis of a circular GMR device. This indicates a shearing motion between the sensor and the magnetic device. When the sensor is parallel to the vertical axis of this device, there is a fall off of the relatively constant signal at about 25 mm. separation. The GMR sensor combination varies its resistance according to the direction of the external magnetic field, thereby providing an absolute angle sensor. The position of the GMR magnet can be registered at any angle from 0 to 360 degrees.

In the external stimulator 42 shown in FIG. 15, an indicator unit 280 which is provided to indicate proximity distance or coil proximity failure (for situations where the patch containing the external coil 46, has been removed, or is twisted abnormally etc.). Indication is also provided to assist in the placement of the patch. In case of general failure, a red light with audible signal is provided when the signal is not reaching the subcutaneous circuit. The indicator unit 280 also displays low battery status. The information on the low battery, normal and out of power conditions forewarns the user of the requirements of any corrective actions.

Also shown in FIG. 15, the programmable parameters are stored in a programmable logic 264. The predetermined programs stored in the external stimulator are capable of being modified through the use of a separate programming station 77. The Programmable Array Logic Unit 264 and interface unit 270 are interfaced to the programming station 77. The programming station 77 can be used to load new programs, change the existing predetermined programs or the program parameters for various stimulation programs. The programming station is connected to the programmable array unit 75 (comprising programmable array logic 304 and interface unit 270) with an RS232-C serial connection. The main purpose of the serial line interface is to provide an RS232-C standard interface.

This method enables any portable computer with a serial interface to communicate and program the parameters for storing the various programs. The serial communication interface receives the serial data, buffers this data and converts it to a 16 bit parallel data. The programmable array logic 264 component of programmable array unit receives the parallel data bus and stores or modifies the data into a random access matrix. This array of data also contains special logic and instructions along with the actual data. These special instructions also provide an algorithm for storing, updating and retrieving the parameters from long-term memory. The programmable logic array unit 264, interfaces with long term memory to store the predetermined programs. All the previously modified programs can be stored here for access at any time, as well as, additional programs can be locked out for the patient. The programs consist of specific parameters and each unique program will be stored sequentially in long-term memory. A battery unit is present to provide power to all the components. The logic for the storage and decoding is stored in a random addressable storage matrix (RASM).

Conventional microprocessor and integrated circuits are used for the logic, control and timing circuits. Conventional bipolar transistors are used in radio-frequency oscillator, pulse amplitude ramp control and power amplifier. A standard voltage regulator is used in low-voltage detector. The hardware and software to deliver the pre-determined programs is well known to those skilled in the art.

Figure 17:
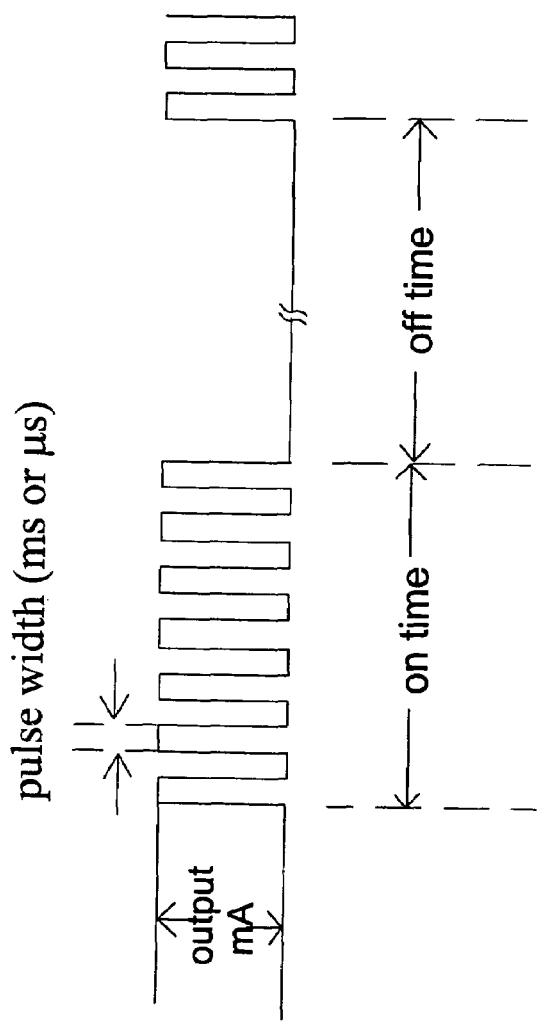
FIG. 17 shows the pulse train to be transmitted to the nerve tissue.
Figure 18:
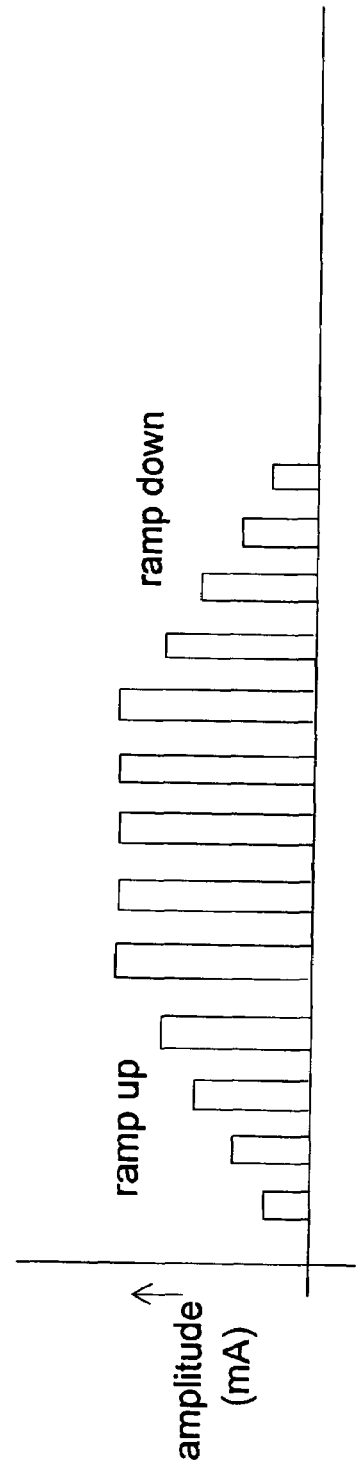
FIG. 18 shows the ramp-up and ramp-down characteristic of the pulse train.

The pulses delivered to the nerve tissue for stimulation therapy are shown graphically in FIG. 17. As shown in FIG. 18, for patient comfort when the electrical stimulation is turned on, the electrical stimulation is ramped up and ramped down, instead of abrupt delivery of electrical pulses.

The selective stimulation to the nerve tissue can be performed in one of two ways. One method is to activate one of several "pre-determined" programs. A second method is to "custom" program the electrical parameters which can be selectively programmed, for specific therapy to the individual patient. The electrical parameters which can be individually programmed, include variables such as pulse amplitude, pulse width, frequency of stimulation, stimulation on-time, and stimulation off-time. Table two below defines the approximate range of parameters,

TABLE 2

Electrical parameter range delivered to the nerve

| PARAMER | RANGE |
| --- | --- |
| Pulse Amplitude | 0.1 Volt-10 Volts |
| Pulse width | 20 μS-5 mSec. |
| Frequency | 5 Hz-200 Hz |
| On-time | 10 Secs-24 hours |
| Off-time | 10 Secs-24 hours |

The parameters in Table 2 are the electrical signals delivered to the nerve via the two electrodes 61, 62 (distal and proximal) around the nerve, as shown in FIG. 18. It being understood that the signals generated by the external pulse generator 42 and transmitted via the primary coil 46 are larger, because the attenuation factor between the primary coil and secondary coil is approximately 10-20 times, depending upon the distance, and orientation between the two coils. Accordingly, the range of transmitted signals of the external pulse generator are approximately 10-20 times larger than shown in Table 2.

Figure 19:
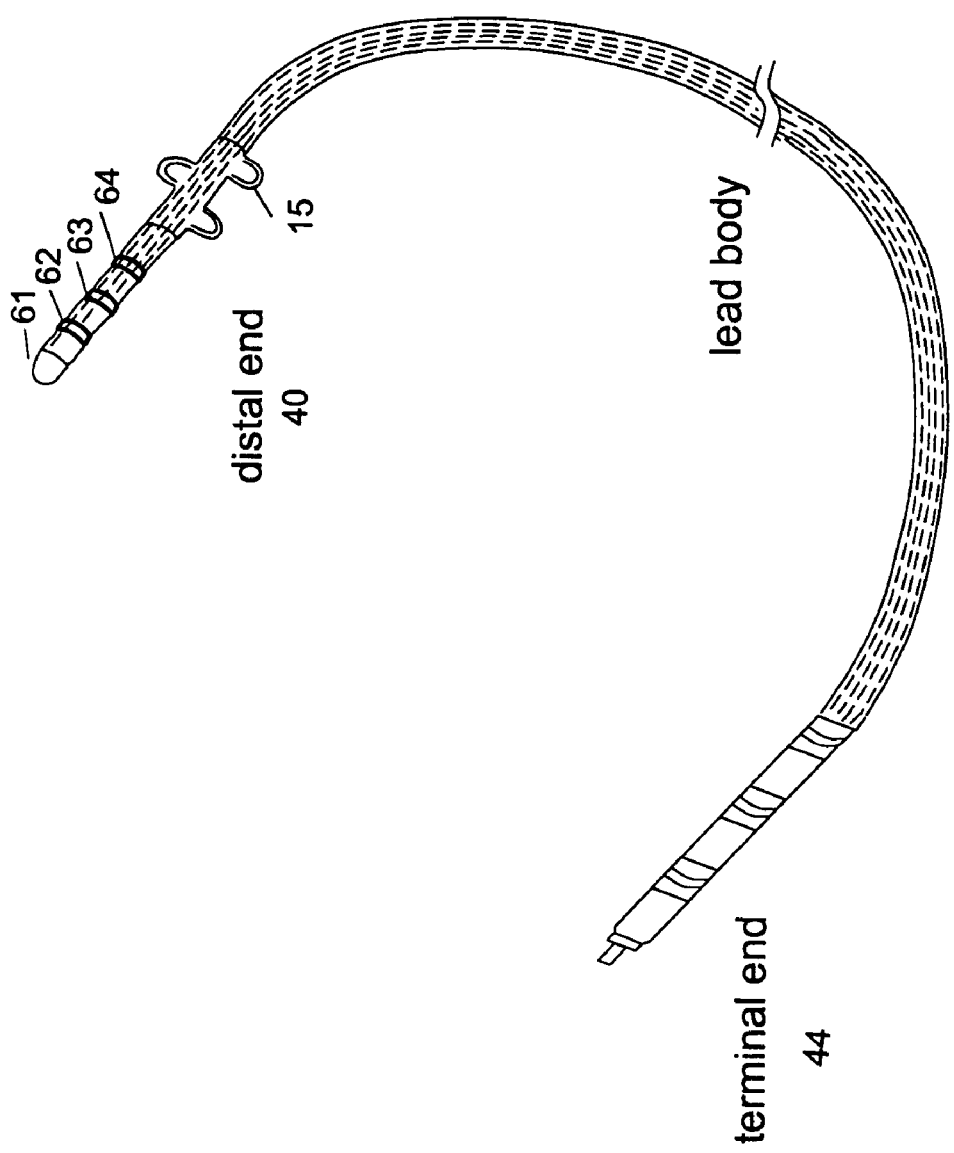
FIG. 19 is a schematic diagram of the implantable lead.

Referring now to FIG. 19, the implanted lead component of the system is somewhat similar to cardiac pacemaker leads, except for distal portion 40 (or electrode end) of the lead. The lead terminal preferably is linear, even though it can be bifurcated, and plug(s) into the cavity of the pulse generator means. The lead body 59 insulation may be constructed of medical grade silicone, silicone reinforced with polytetrafluoro-ethylene (PTFE), or polyurethane. The electrodes 61, 62, 63, 64 for stimulating the nerve tissue 54 may either wrap around the nerve tissue or may be implanted adjacent to the nerve tissue to be stimulated.

Figure 20A:
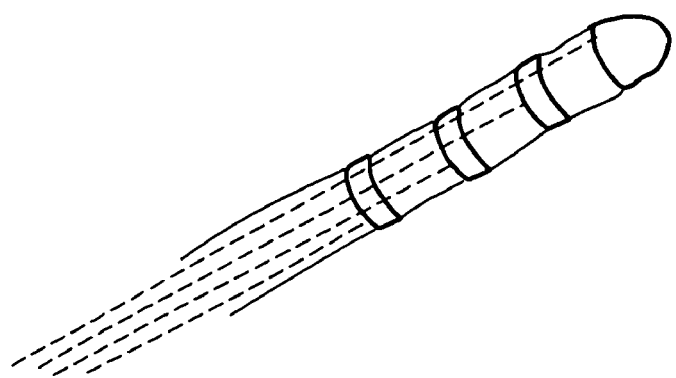
FIGS. 20A, 20B, and 20C depicts various types of electrodes at the distal end of a lead.
Figure 20B:
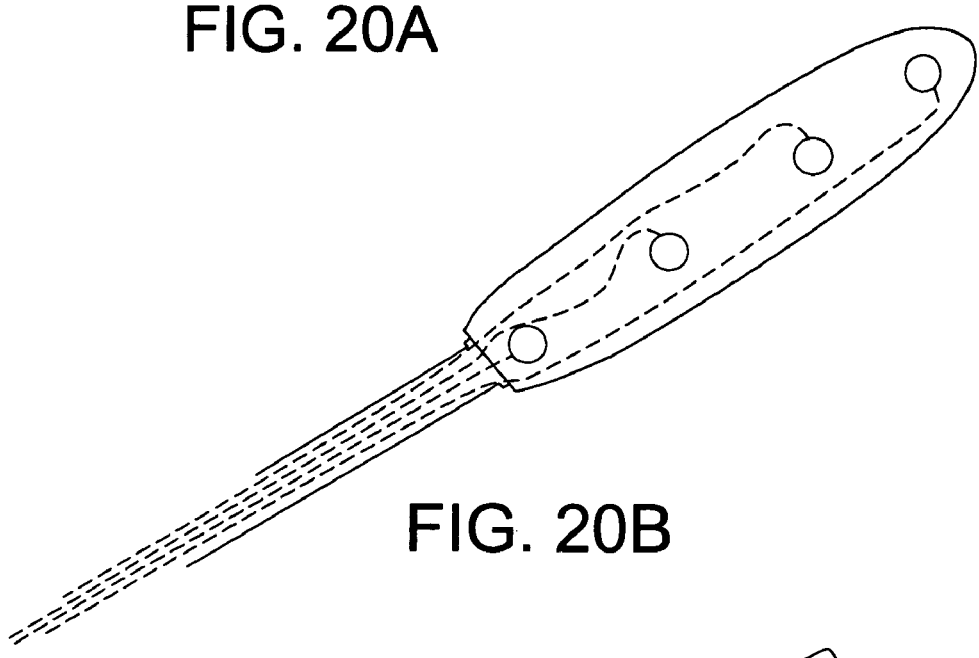
Figure 20C:
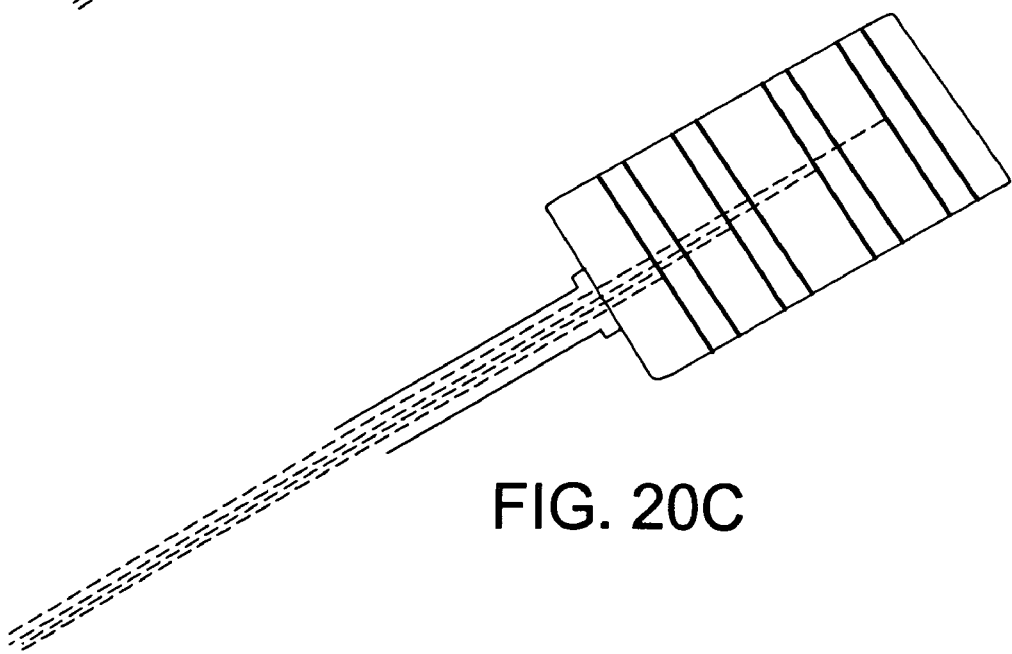

FIGS. 20A, 20B, 20C show different types of electrodes at the distal end 40 of the lead. FIG. 20A is a close up of electrodes 61, 62, 63, 64 as was shown in FIG. 19, with an anchoring sleeve 15 pulled back from the most proximal electrode. FIG. 20B shows a paddle electrode. And FIG. 20C shows a type of electrodes that can be wrapped around the nerve tissue 54 to be stimulated.

Figure 21A:
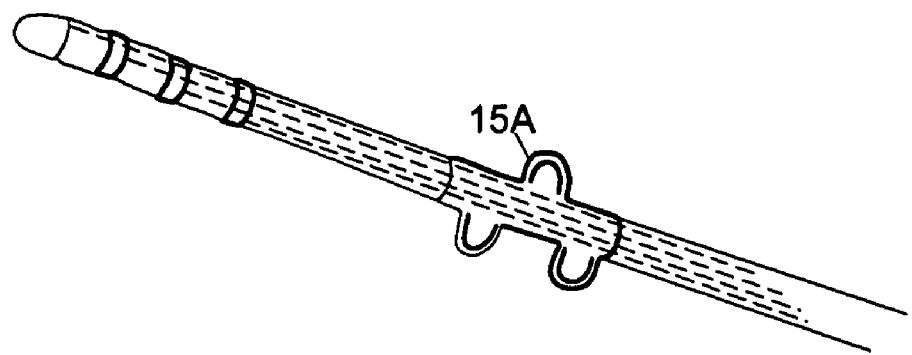
FIGS. 21A, 21B, 21C, 21D, and 21E are diagrams depicting various types of anchoring sleeves.
Figure 21B:
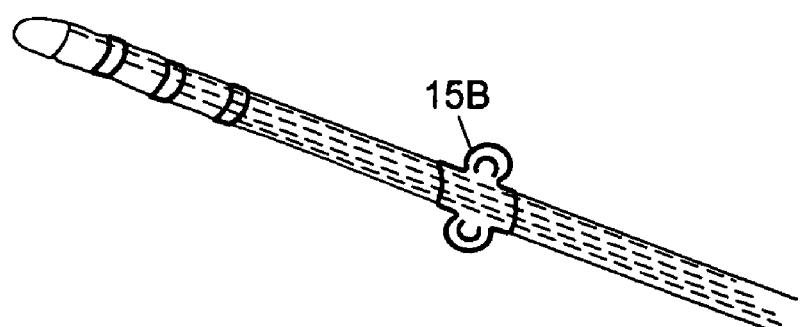
Figure 21C:
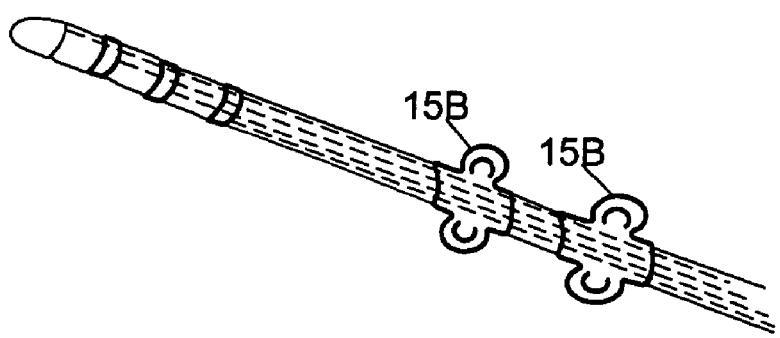
Figure 21D:
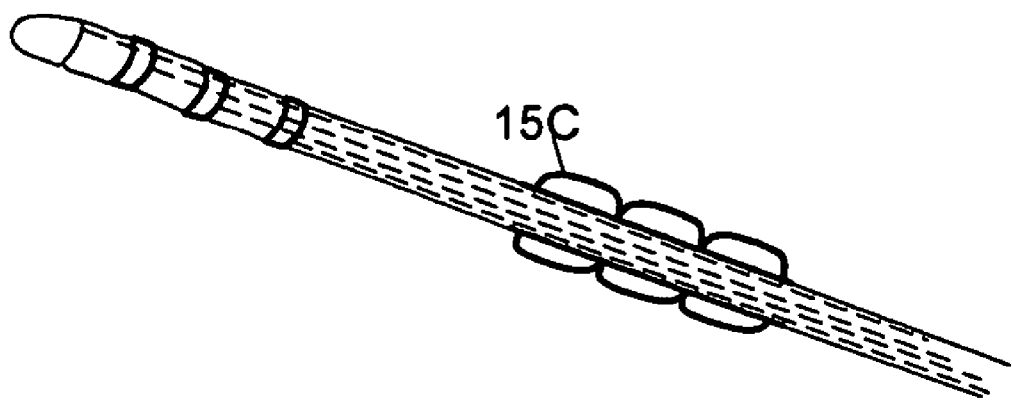
Figure 21E:
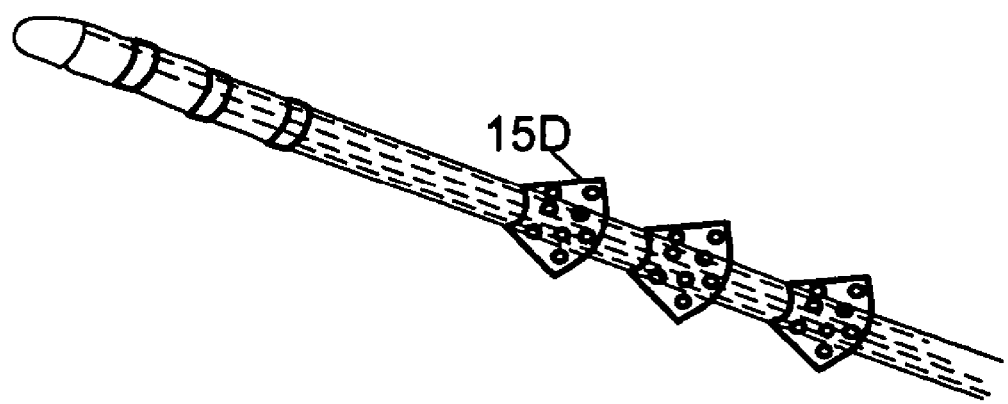

In any of these leads, there may be one, or two, or three, or four, or more electrodes. This provides flexibility in choosing a different pair to stimulate over the implanted life of the lead. FIGS. 21A, 21B, 21C, 21D, and 21E show different types of anchoring devices (15, 15A 15B, 15C) used in the method and system of this invention. All anchoring devices are make of silicone in this embodiment, even though they can be made of other bicompatible material. FIGS. 21A, 21B, and 21C show anchoring sleeves which have holes for suturing the lead to the tissue. FIG. 21D shows a type of suture sleeve that has grooves 15B for suturing to the tissue. FIG. 21E shows a passive fixation anchoring sleeve 15C where the holes in the silicone material promote tissue in-growth over time, for lead fixation.

Figure 23:
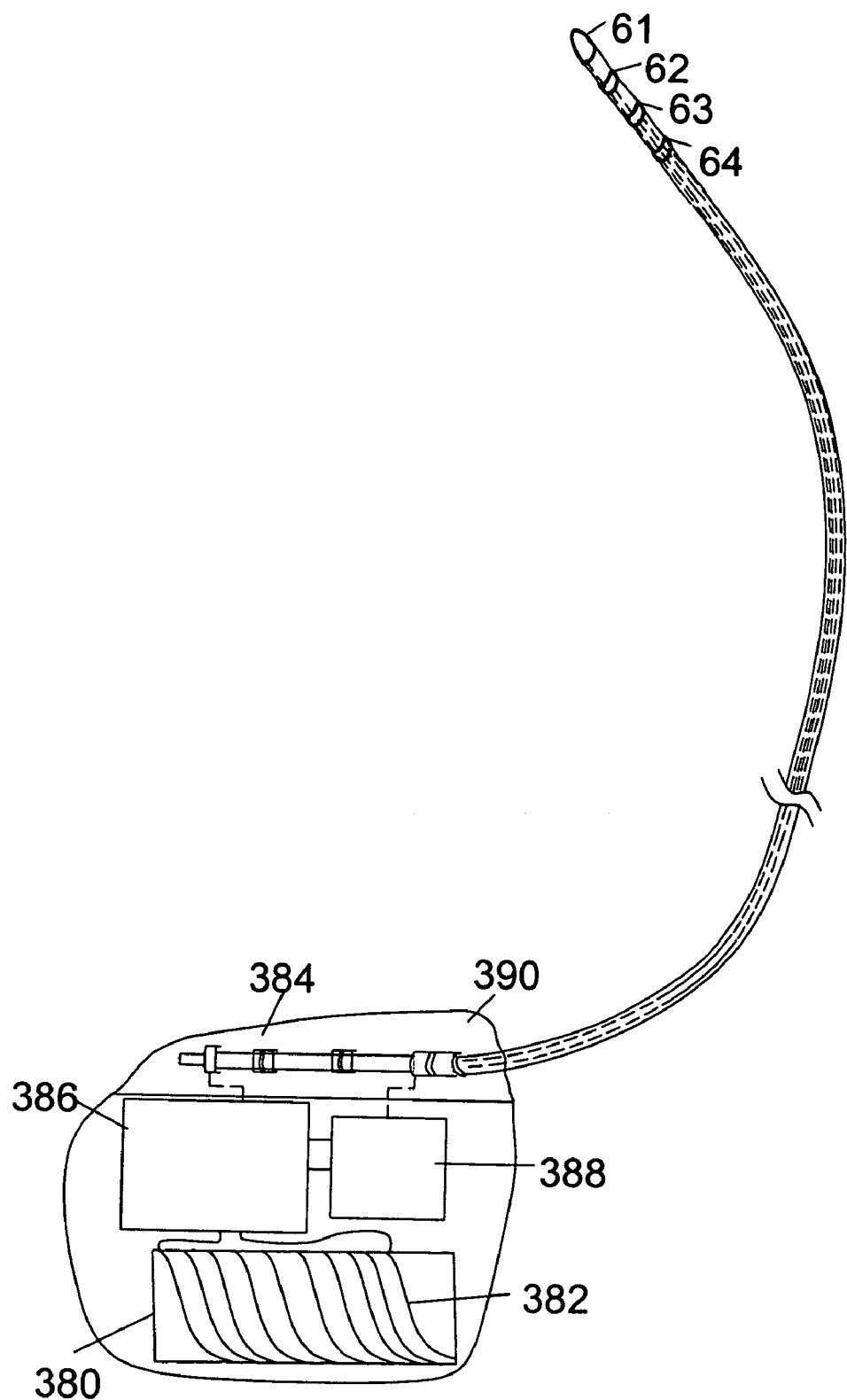
FIG. 23 is a schematic diagram showing the implantable lead and one form of stimulus-receiver.

The stimulating electrodes may be made of pure platinum, platinum/Iridium alloy or platinum/iridium coated with titanium nitride. The conductor connecting the terminal to the electrodes 61, 62, 63, 64 is made of an alloy of nickel-cobalt. The implanted lead design variables are also summarized in table three below.

several hours by itself, once the capacitors are charged. The packaging is shown in FIG. 23. Using mostly hybrid components and appropriate packaging, the implanted portion of the system described below is conducive to miniaturization. As shown in FIG. 23, a solenoid coil 382 wrapped around a ferrite core 380 is used as the secondary of an air-gap transformer for receiving power and data to the implanted device. The primary coil is external to the body. Since the coupling between the external transmitter coil and receiver coil 382 may be weak, a high-efficiency transmitter/amplifier is used in order to supply enough power to the receiver coil 382. Class-D or Class-E power amplifiers may be used

TABLE 3

Lead design variables

| Proximal End | | | | | Distal End |
|---|---|---|---|---|---|
| Lead Terminal | Lead body-Insulation Materials | Lead-Coating | Conductor (connecting proximal and distal ends) | Electrode - Material | Electrode - Type |
| Linear bipolar | Polyurethane | Antimicrobial coating | Alloy of Nickel-Cobalt | Pure Platinum | Wrap-around electrode |
| Bifurcated | Silicone | Anti-Inflammatory coating | | Platinum-Iridium (Pt/Ir) Alloy | Standard Ball and Ring electrodes |
| | Silicone with Polytetrafluoroethylene (PTFE) | Lubricious coating | | Pt/Ir coated with Titanium Nitride | Steroid eluting |
| | | | | Carbon | Hydrogel electrodes |
| | | | | | Cuff electrodes |

Once the lead is fabricated, coating such as anti-microbial, anti-inflammatory, or lubricious coating may be applied to the body of the lead.

Figure 22A:
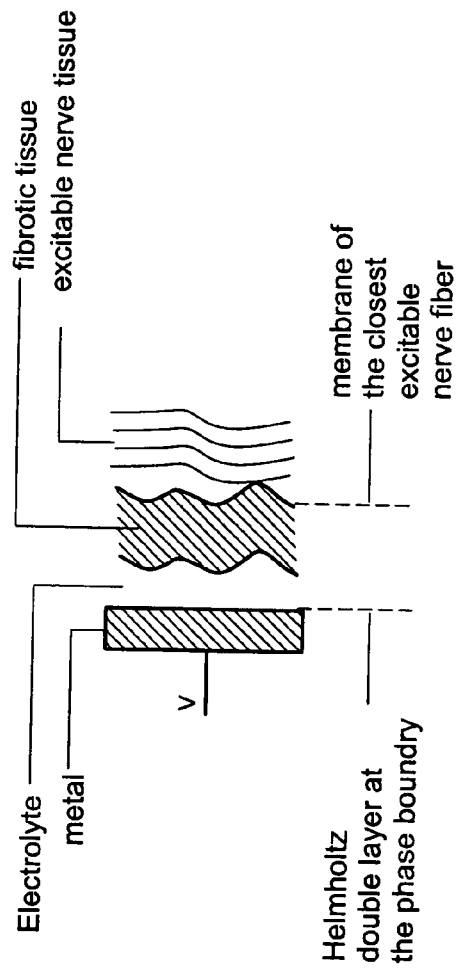
FIG. 22A is diagram depicting stimulating electrode-tissue interface.
Figure 22B:
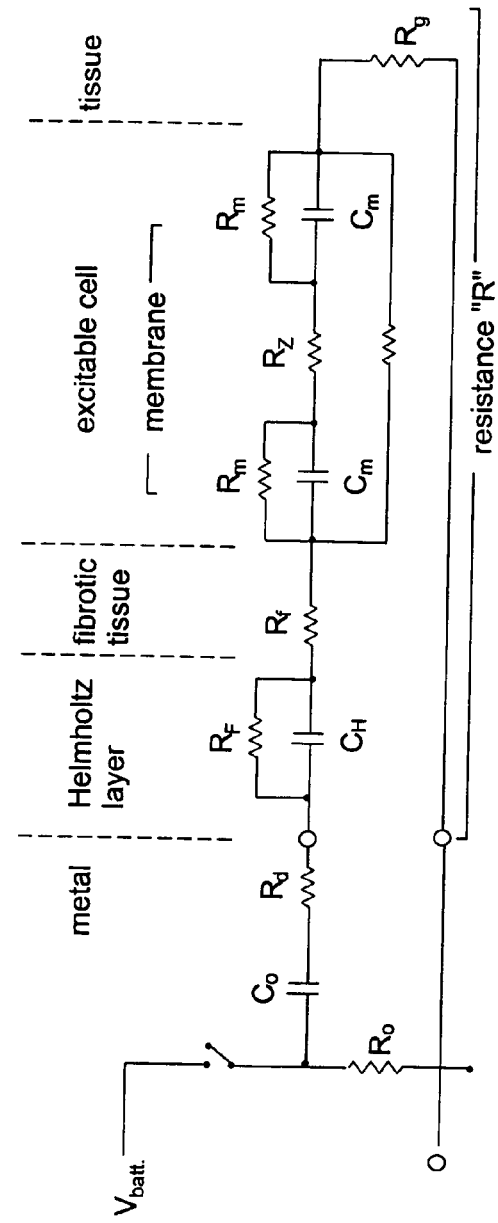
FIG. 22B is diagram depicting an electrical model of the electrode-tissue interface.

FIG. 22A summarizes electrode-tissue interface between the nerve tissue and electrodes 61, 62. There is a thin layer of fibrotic tissue between the stimulating electrode 61 and the excitable nerve fibers of the nerve tissue 54. FIG. 22B summarizes the most important properties of the metal/tissue phase boundary in an equivalent circuit diagram. Both the membrane of the nerve fibers and the electrode surface are represented by parallel capacitance and resistance. Application of a constant battery voltage Vbat from the pulse generator, produces voltage changes and current flow, the time course of which is crucially determined by the capacitive components in the equivalent circuit diagram. During the pulse, the capacitors Co, Ch and Cm are charged through the ohmic resistances, and when the voltage Vbat is turned off, the capacitors discharge with current flow on the opposite direction.

Implanted Stimulus-Receiver Comprising a High Value Capacitor for Storing Charge, Used in Conjunction with an External Stimulator In one embodiment, the implanted stimulus-receiver may be a system which is RF coupled combined with a power source. In this embodiment, the implanted stimulus-receiver contains high value, small sized capacitor(s) for storing charge and delivering electric stimulation pulses for up to for this purpose. The coil for the external transmitter (primary coil) may be placed in the pocket of a customized garment.

Figure 24:
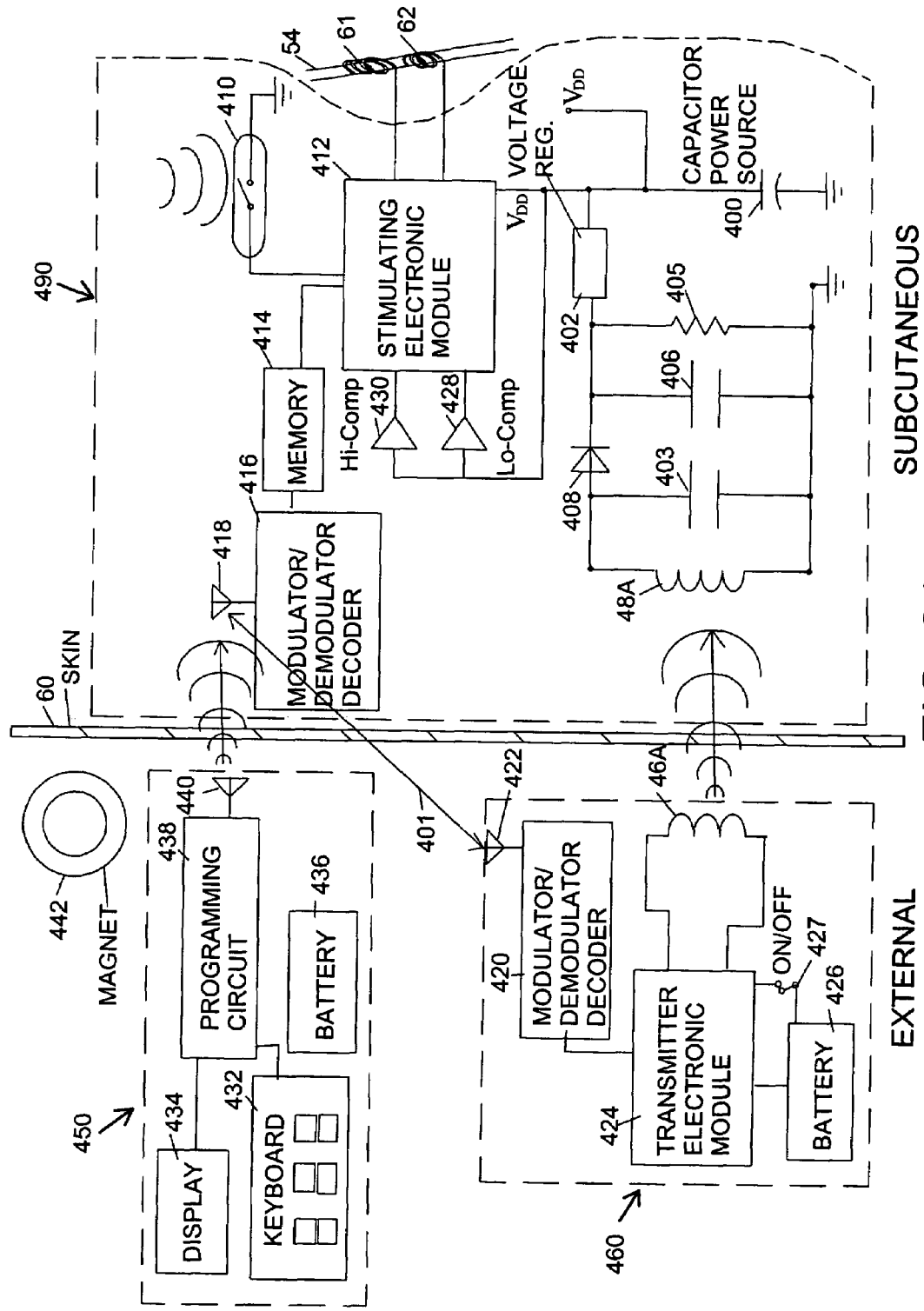
FIG. 24 is a schematic block diagram showing a system for neuromodulation of nerve tissue, with an implanted component which is both RF coupled and contains a capacitor power source.

As shown in conjunction with FIG. 24 of the implanted stimulus-receiver 490 and the system, the receiving inductor 48A and tuning capacitor 403 are tuned to the frequency of the transmitter. The diode 408 rectifies the AC signals, and a small sized capacitor 406 is utilized for smoothing the input voltage $V_I$ fed into the voltage regulator 402. The output voltage $V_D$ of regulator 402 is applied to capacitive energy power supply and source 400 which establishes source power $V_{DD}$. Capacitor 400 is a big value, small sized capacative energy source which is classified as low internal impedance, low power loss and high charge rate capacitor, such as Panasonic Model No. 641.

The refresh-recharge transmitter unit 460 includes a primary battery 426, an ON/Off switch 427, a transmitter electronic module 442, an RF inductor power coil 46A, a modulator/demodulator 420 and an antenna 422.

When the ON/OFF switch is on, the primary coil 46A is placed in close proximity to skin 60 and secondary coil 48A of the implanted stimulator 490. The inductor coil 46A emits RF waves establishing EMF wave fronts which are received by secondary inductor 48A. Further, transmitter electronic module 442 sends out command signals which are converted by modulator/demodulator decoder 420 and sent via antenna 422 to antenna 418 in the implanted stimulator 490. These received command signals are demodulated by decoder 416 and replied and responded to, based on a program in memory 414 (matched against a "command table" in the memory). Memory 414 then activates the proper controls and the inductor receiver coil 48A accepts the RF coupled power from inductor 46A.

The RF coupled power, which is alternating or AC in nature, is converted by the rectifier 408 into a high DC voltage. Small value capacitor 406 operates to filter and level this high DC voltage at a certain level. Voltage regulator 402 converts the high DC voltage to a lower precise DC voltage while capacitive power source 400 refreshes and replenishes.

When the voltage in capacative source 400 reaches a predetermined level (that is $V_{DD}$ reaches a certain predetermined high level), the high threshold comparator 430 fires and stimulating electronic module 412 sends an appropriate command signal to modulator/decoder 416. Modulator/decoder 416 then sends an appropriate "fully charged" signal indicating that capacitive power source 400 is fully charged, is received by antenna 422 in the refresh-recharge transmitter unit 460.

In one mode of operation, the patient may start or stop stimulation by waving the magnet 442 once near the implant. The magnet emits a magnetic force $L_m$ which pulls reed switch 410 closed. Upon closure of reed switch 410, stimulating electronic module 412 in conjunction with memory 414 begins the delivery (or cessation as the case may be) of controlled electronic stimulation pulses to the nerve tissue 54 via a pair of electrodes. In another mode (AUTO), the stimulation is automatically delivered to the implanted lead based upon programmed ON/OFF times.

The programmer unit 450 includes keyboard 432, programming circuit 438, rechargeable battery 436, and display 434. The physician or medical technician programs programming unit 450 via keyboard 432. This program regarding the frequency, pulse width, modulation program, ON time etc. is stored in programming circuit 438. The programming unit 450 must be placed relatively close to the implanted stimulator 490 in order to transfer the commands and programming information from antenna 440 to antenna 418. Upon receipt of this programming data, modulator/demodulator and decoder 416 decodes and conditions these signals, and the digital programming information is captured by memory 414. This digital programming information is further processed by stimulating electronic module 412. In the DEMAND operating mode, after programming the implanted stimulator, the patient turns ON and OFF the implanted stimulator via hand held magnet 442 and the reed switch 410. In the automatic mode (AUTO), the implanted stimulator turns ON and OFF automatically according to the programmed values for the ON and OFF times.

Other simplified versions of such a system may also be used. For example, a system such as this, where a separate programmer is eliminated, and simplified programming is performed with a magnet and reed switch, can also be used.

Programmer-Less Implantable Pulse Generator (IPG)

In one embodiment, a programmer-less implantable pulse generator (IPG) may be used. In this embodiment, shown in conjunction with FIG. 25, the implantable pulse generator 171 is provided with a reed switch 92 and memory circuitry 102. The reed switch 92 being remotely actuable by means of a magnet 90 brought into proximity of the pulse generator 171, in accordance with common practice in the art. In this embodiment, the reed switch 92 is coupled to a multi-state converter/timer circuit 96, such that a single short closure of the reed switch can be used as a means for non-invasive encoding and programming of the pulse generator 171 parameters.

Figure 26:
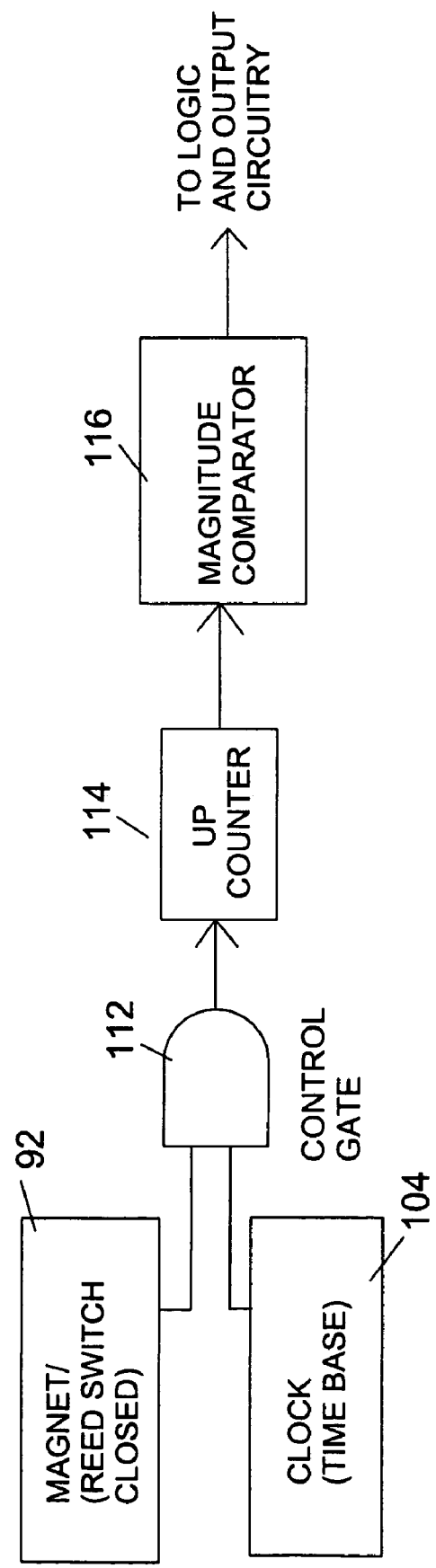
FIG. 26 is a schematic diagram showing implementation of a multi-state converter.

In one embodiment, shown in conjunction with FIG. 26, the closing of the reed switch 92 triggers a counter. The magnet 90 and timer are ANDed together. The system is configured such that during the time that the magnet 82 is held over the pulse generator 171, the output level goes from LOW stimulation state to the next higher stimulation state every 5 seconds. Once the magnet 82 is removed, regardless of the state of stimulation, an application of the magnet, without holding it over the pulse generator 171, triggers the OFF state, which also resets the counter.

Figure 25:
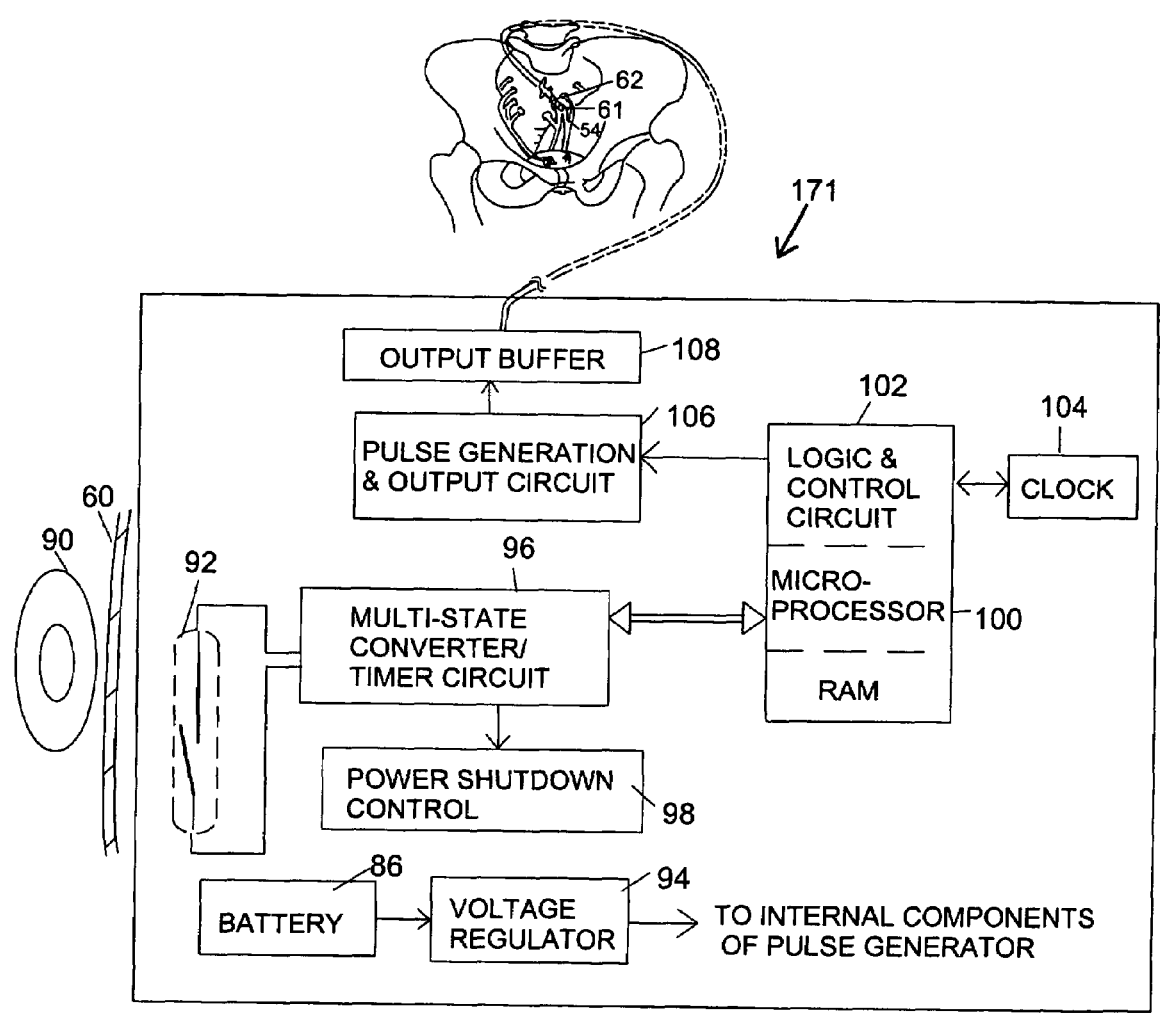
FIG. 25 is a simplified block diagram showing control of an implantable neurostimulator with a magnet.

Once the prepackaged/predetermined logic state is activated by the logic and control circuit 102, as shown in FIG. 25, the pulse generation and amplification circuit 106 deliver the appropriate electrical pulses to the nerve tissue 54 of the patient via an output buffer 108. The delivery of output pulses is configured such that the distal electrode 61 is the cathode and the proximal electrode 62 is the anode. Timing signals for the logic and control circuit 102 of the pulse generator 171 are provided by a crystal oscillator 104. The battery 86 of the pulse generator 171 has terminals connected to the input of a voltage regulator 94. The regulator 94 smoothes the battery output and supplies power to the internal components of the pulse generator 171. A microprocessor 100 controls the program parameters of the device, such as the voltage, pulse width, frequency of pulses, on-time and off-time. The microprocessor may be a commercially available, general purpose microprocessor or microcontroller, or may be a custom integrated circuit device augmented by standard RAM/ROM components.

In one embodiment, there are four stimulation states. A larger (or lower) number of states can be achieved using the same methodology, and such is considered within the scope of the invention. These four states are, LOW stimulation state, LOW-MED stimulation state, MED stimulation state, and HIGH stimulation state. Examples of stimulation parameters (delivered to the nerve tissue) for each state are as follows, LOW stimulation state example is,

| | |
|---|---|
| Current output: | 0.75 milliAmps. |
| Pulse width: | 0.20 msec. |
| Pulse frequency: | 40 Hz |
| ON for 5 minutes | |

LOW-MED stimulation state example is,

| | |
|---|---|
| Current output: | 1.5 milliAmps, |
| Pulse width: | 0.30 msec. |
| Pulse frequency: | 45 Hz |
| ON for 7.5 minutes | |

MED stimulation state example is,

| | |
|---|---|
| Current output: | 2.0 milliAmps. |
| Pulse width: | 0.40 msec. |
| Pulse frequency: | 50 Hz |
| ON for 15 minutes | |

HIGH stimulation state example is,

| | |
|---|---|
| Current output: | 3.0 milliAmps, |
| Pulse width: | 0.50 msec. |
| Pulse frequency: | 60 Hz |
| ON for 30 minutes | |

These prepackaged/predetermined programs are nearly examples, and the actual stimulation parameters will deviate from these depending on the treatment application.

It will be readily apparent to one skilled in the art, that other schemes can be used for the same purpose. For example, instead of placing the magnet 90 on the pulse generator 171 for a prolonged period of time, different stimulation states can be encoded by the sequence of magnet applications. Accordingly, in an alternative embodiment there can be three logic states, OFF, LOW stimulation (LS) state, and HIGH stimulation (HS) state. Each logic state again corresponds to a prepackaged/predetermined program such as presented above. In such an embodiment, the system could be configured such that one application of the magnet triggers the generator into LS State. If the generator is already in the LS state then one application triggers the device into OFF State. Two successive magnet applications triggers the generator into MED stimulation state, and three successive magnet applications triggers the pulse generator in the HIGH Stimulation State. Subsequently, one application of the magnet while the device is in any stimulation state, triggers the device OFF.

Figure 27:
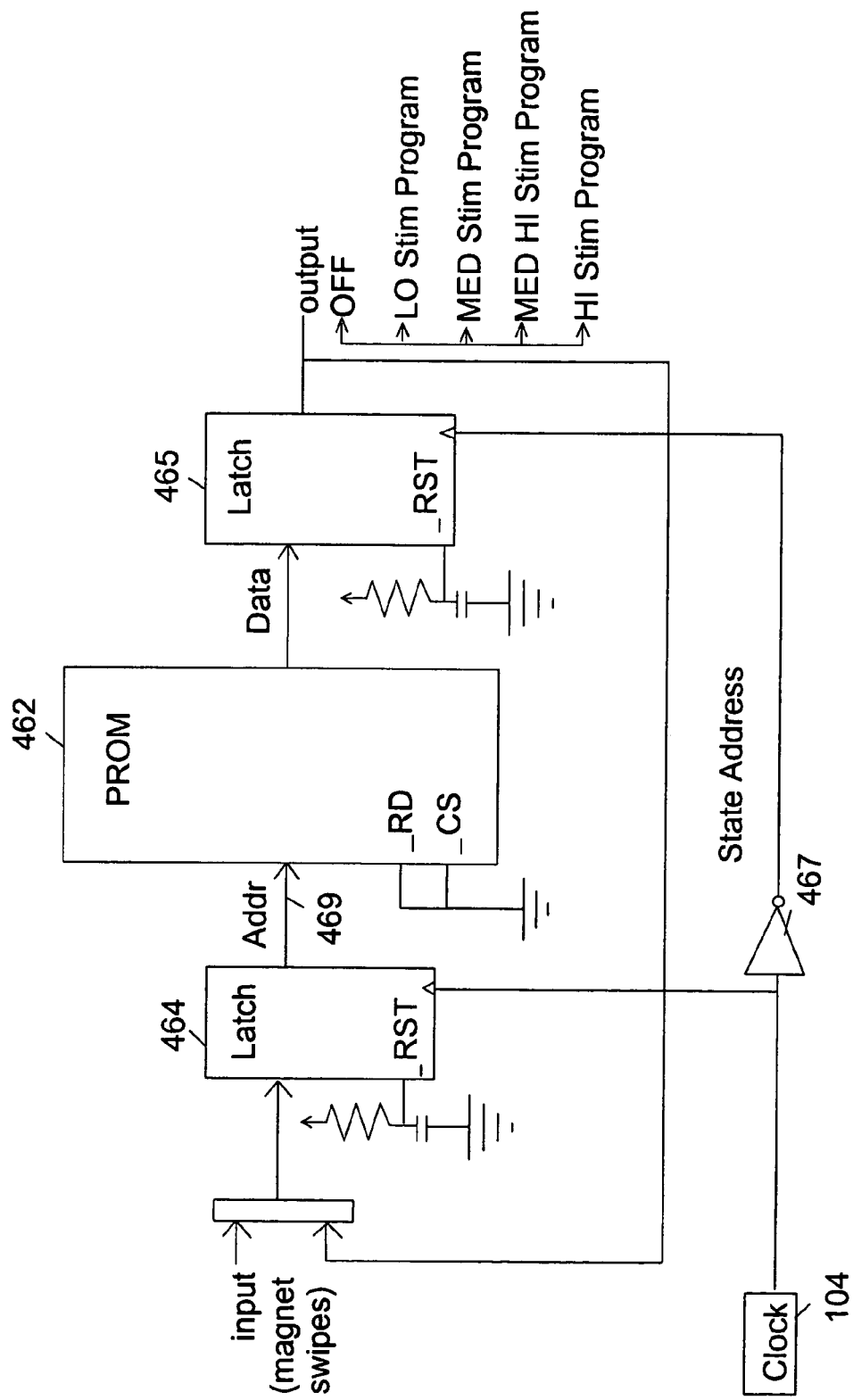
FIG. 27 is a schematic diagram depicting digital circuitry for state machine.

FIG. 27 shows a representative digital circuitry used for the basic state machine circuit. The circuit consists of a PROM 462 that has part of its data fed back as a state address. Other address lines 469 are used as circuit inputs, and the state machine changes its state address on the basis of these inputs. The clock 104 is used to pass the new address to the PROM 462 and then pass the output from the PROM 462 to the outputs and input state circuits. The two latches 464, 465 are operated 180° out of phase to prevent glitches from unexpectedly affecting any output circuits when the ROM changes state. Each state responds differently according to the inputs it receives.

The advantage of this embodiment is that it is cheaper to manufacture than a fully programmable implantable pulse generator (IPG).

Programmable Implantable Pulse Generator (IPG)

Figure 28:
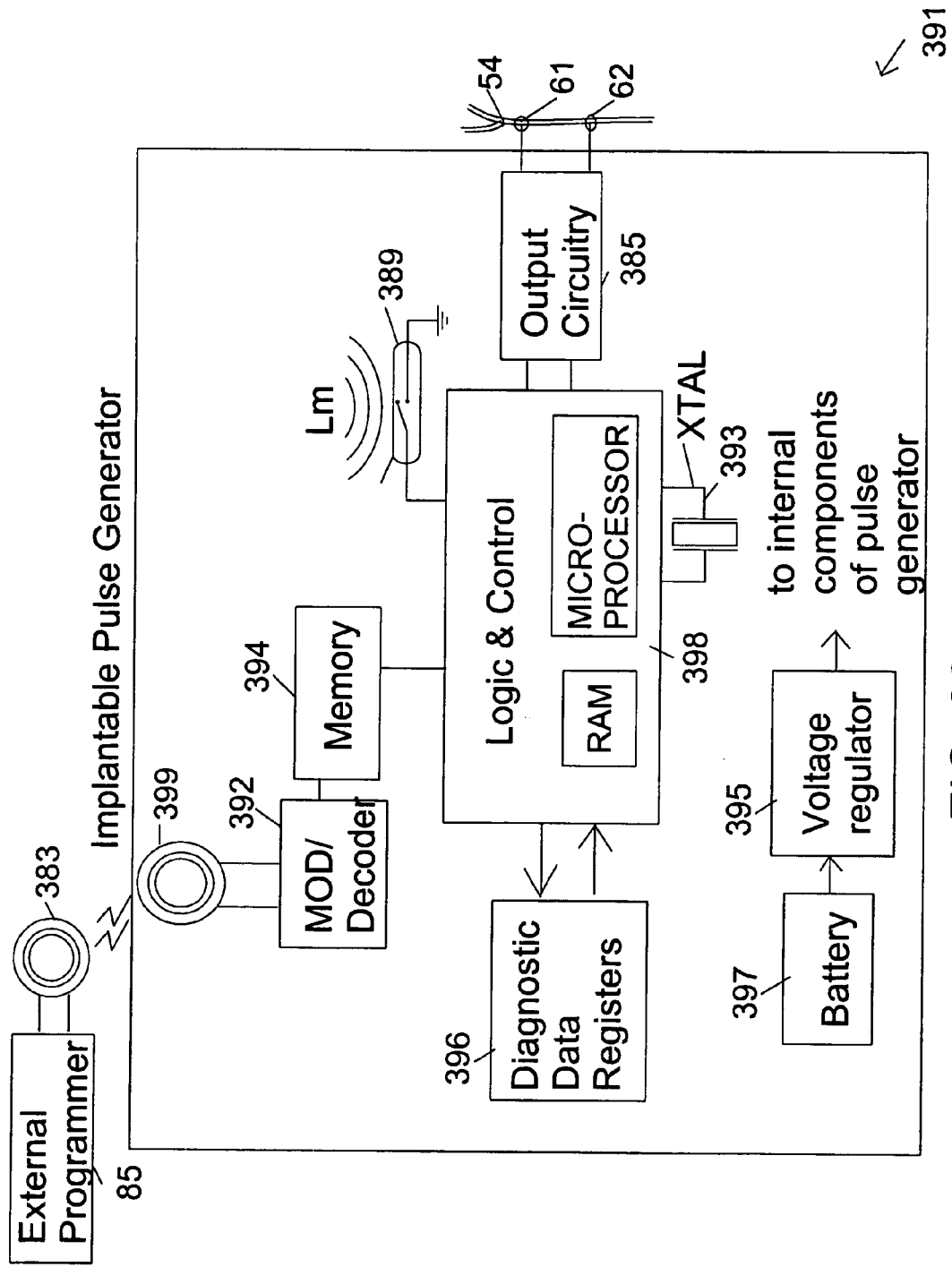
FIG. 28 is a simplified block diagram of the implantable pulse generator.

In one embodiment, a fully programmable implantable pulse generator (IPG) may be used. Shown in conjunction with FIG. 28, the implantable pulse generator unit 391 is preferably a microprocessor based device, where the entire circuitry is encased in a hermetically sealed titanium can. As shown in the overall block diagram, the logic & control unit 398 provides the proper timing for the output circuitry 385 to generate electrical pulses that are delivered to a pair of electrodes via a lead 40. The pair of electrodes to which the stimulation energy is delivered is switchable. Programming of the implantable pulse generator (I PG) is done via an external programmer 85, as described later. Once programmed via an external programmer 85, the implanted pulse generator 391 provides appropriate electrical stimulation pulses to the nerve tissue 54 via the stimulating electrode pair.

This embodiment may also comprise fixed pre-determined/pre-packaged programs. Examples of LOW, LOW-MED, MED, and HIGH stimulation states were given in the previous section, under "Programmer-less Implantable Pulse Generator (IPG)". These pre-packaged/pre-determined programs comprise unique combinations of pulse amplitude, pulse width, pulse frequency, ON-time and OFF-time.

In addition, each parameter may be individually programmed and stored in memory. A small library of "customized" programs that work particularly well for the patient, may be programmed and stored in the implanted device. Any of the program can be activated on demand. The range of programmable electrical stimulation parameters are shown in table 4 below.

TABLE 4

Programmable electrical parameter range

| PARAMER | RANGE |
|---|---|
| Pulse Amplitude | 0.1 Volt-10 Volts |
| Pulse width | 20 µS-5 mSec. |
| Frequency | 3 Hz-300 Hz |
| On-time | 5 Secs-24 hours |
| Ramp | ON/OFF |

Figure 29:
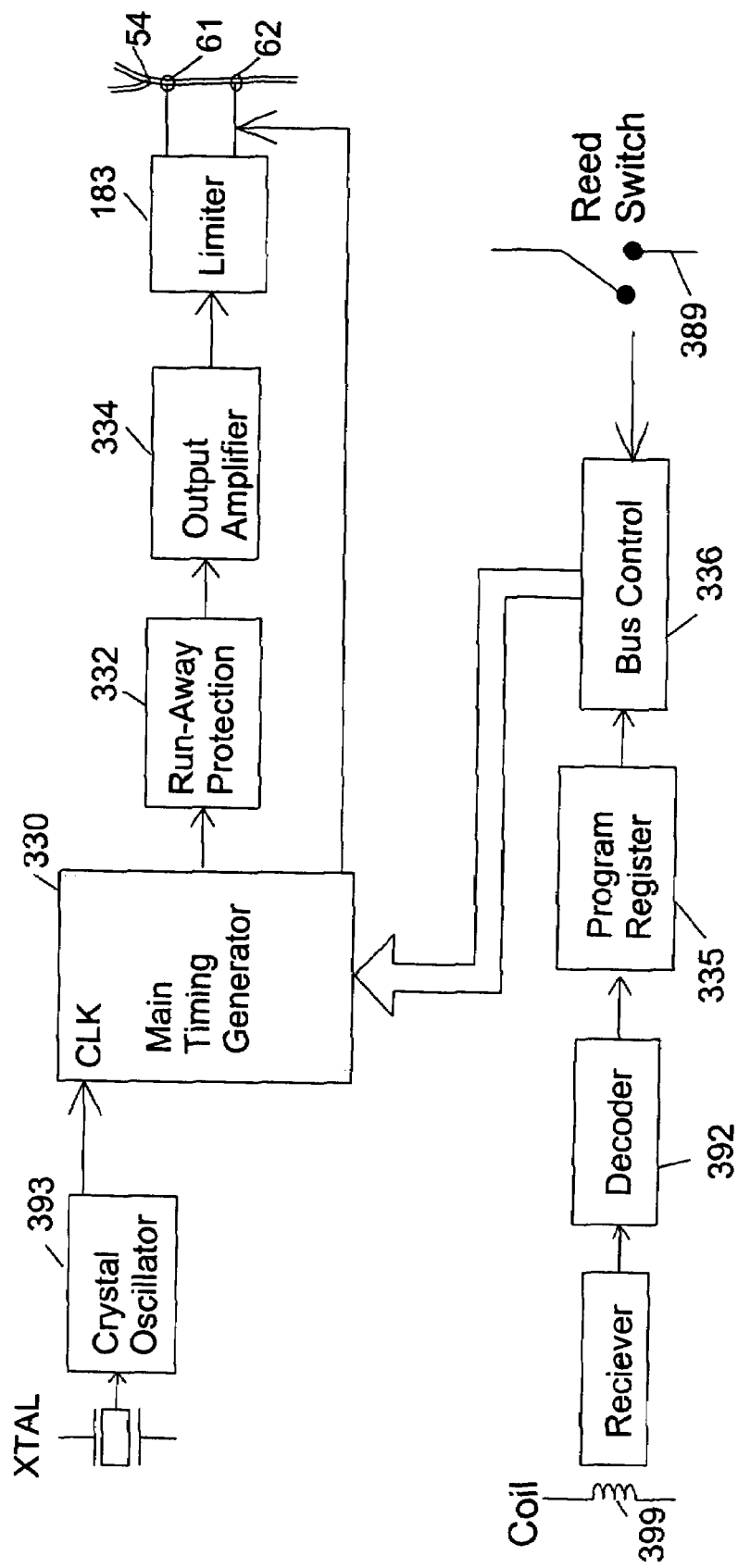
FIG. 29 is a functional block diagram of a microprocessor-based implantable pulse generator.
Figure 30:
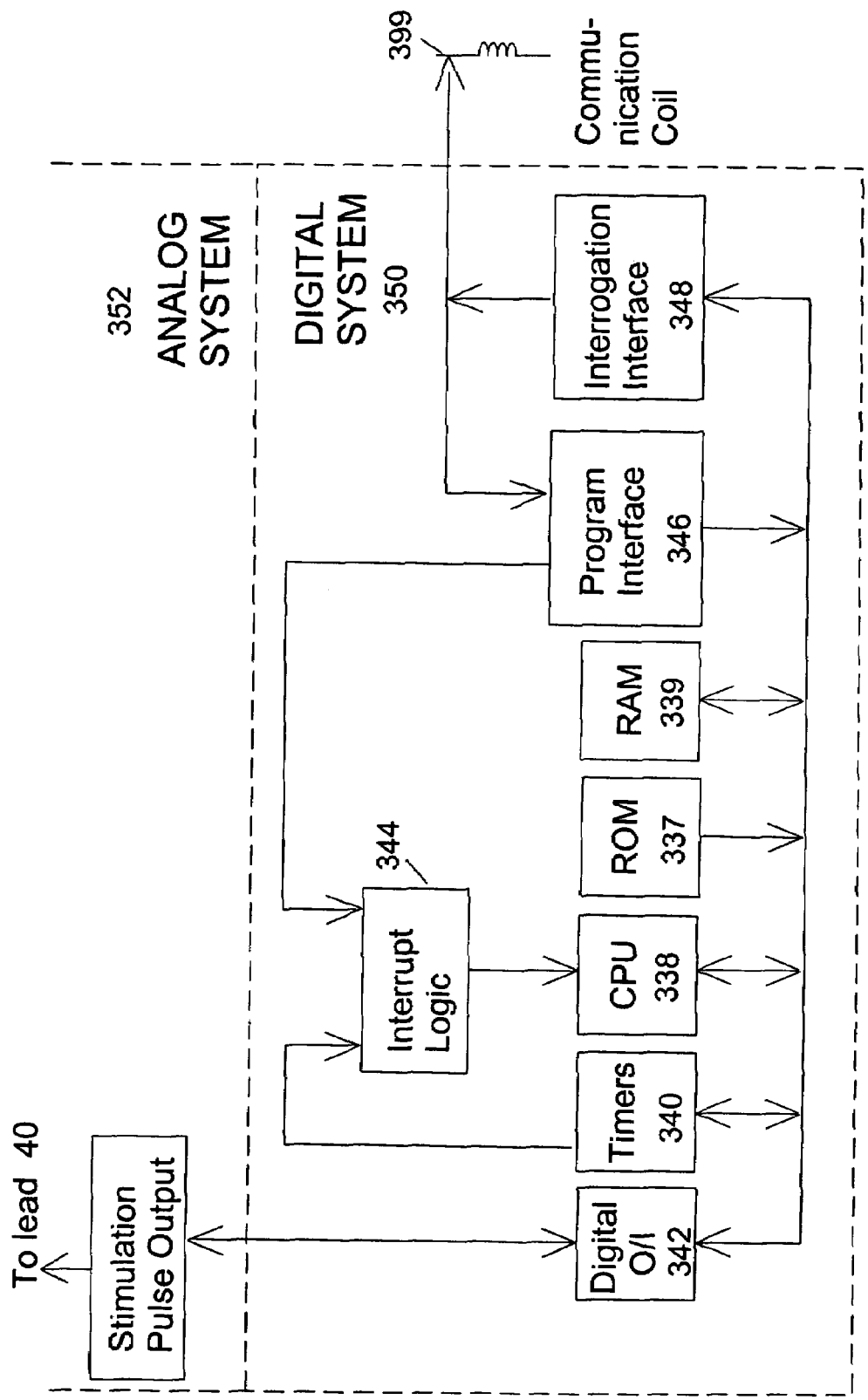
FIG. 30 shows details of implanted pulse generator.

Shown in conjunction with FIGS. 29 and 30, the electronic stimulation module comprises both digital 350 and analog 352 circuits. A main timing generator 330 (shown in FIG. 29), controls the timing of the analog output circuitry for delivering neuromodulating pulses to nerve tissue 54, via output amplifier 334. Limiter 183 prevents excessive stimulation energy from getting to the nerve tissue 54. The main timing generator 330 receiving clock pulses from crystal oscillator 393. Main timing generator 330 also receiving input from programmer 85 via coil 399. FIG. 30 highlights other portions of the digital system such as CPU 338, ROM 337, RAM 339, program interface 346, interrogation interface 348, timers 340, and digital O/I 342.

Most of the digital functional circuitry 350 is on a single chip (IC). This monolithic chip along with other IC's and components such as capacitors and the input protection diodes are assembled together on a hybrid circuit. As well known in the art, hybrid technology is used to establish the connections between the circuit and the other passive components. The integrated circuit is hermetically encapsulated in a chip carrier. A coil 399 situated under the hybrid substrate is used for bidirectional telemetry. The hybrid and battery 397 are encased in a titanium can 65. This housing is a two-part titanium capsule that is hermetically sealed by laser welding. Alternatively, electron-beam welding can also be used. The header 79 is a cast epoxy-resin with hermetically sealed feed-through, and form the lead 40 connection block.

Figure 31A:
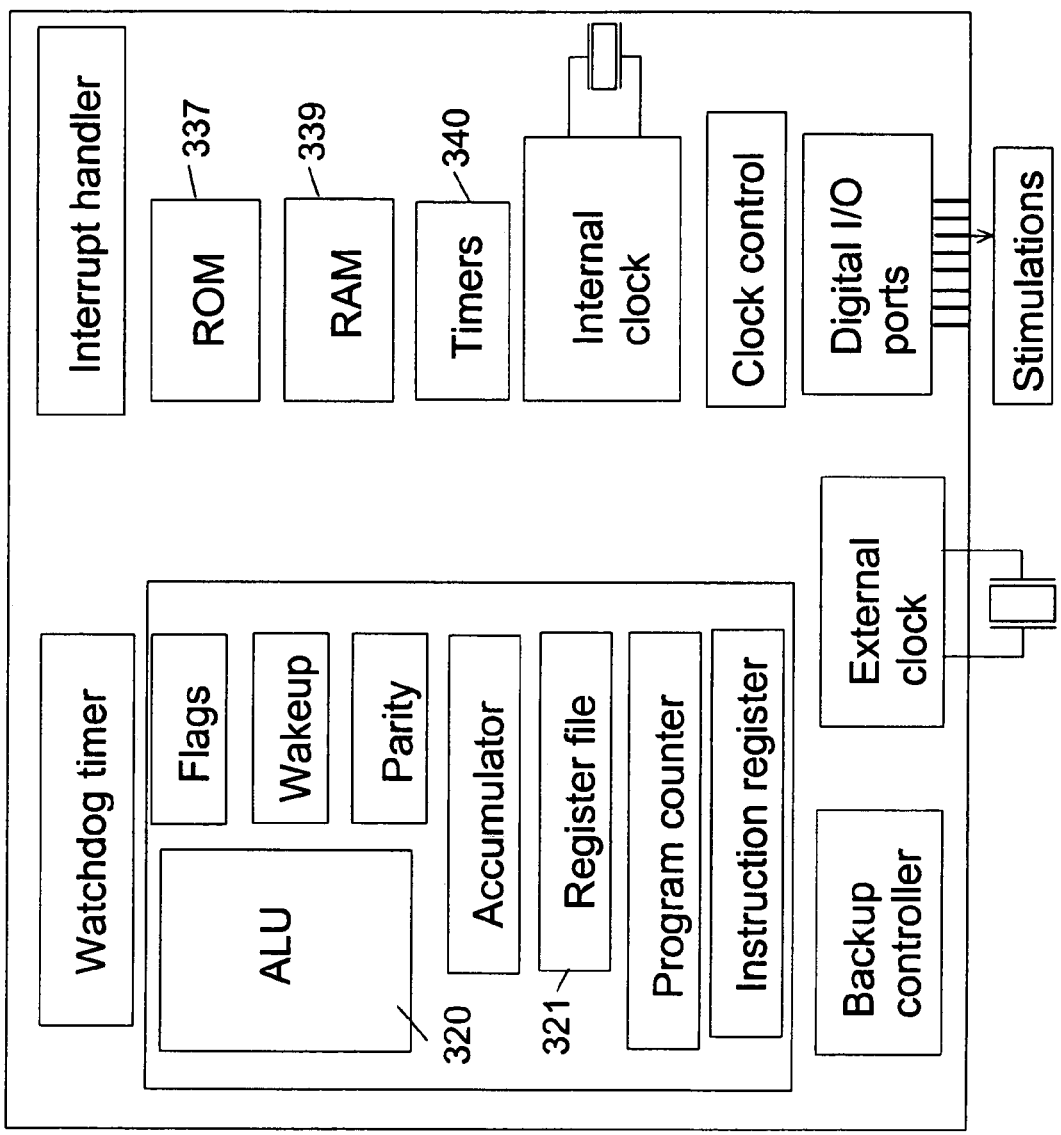
FIGS. 31A and 31B show details of digital components of the implantable circuitry.

For further details, FIG. 31A highlights the general components of an 8-bit microprocessor as an example. It will be obvious to one skilled in the art that higher level microprocessor, such as a 16-bit or 32-bit may be utilized, and is considered within the scope of this invention. It comprises a ROM 337 to store the instructions of the program to be executed and various programmable parameters, a RAM 339 to store the various intermediate parameters, timers 340 to track the elapsed intervals, a register file 321 to hold intermediate values, an ALU 320 to perform the arithmetic calculation, and other auxiliary units that enhance the performance of a microprocessor-based IPG system.

Figure 31B:
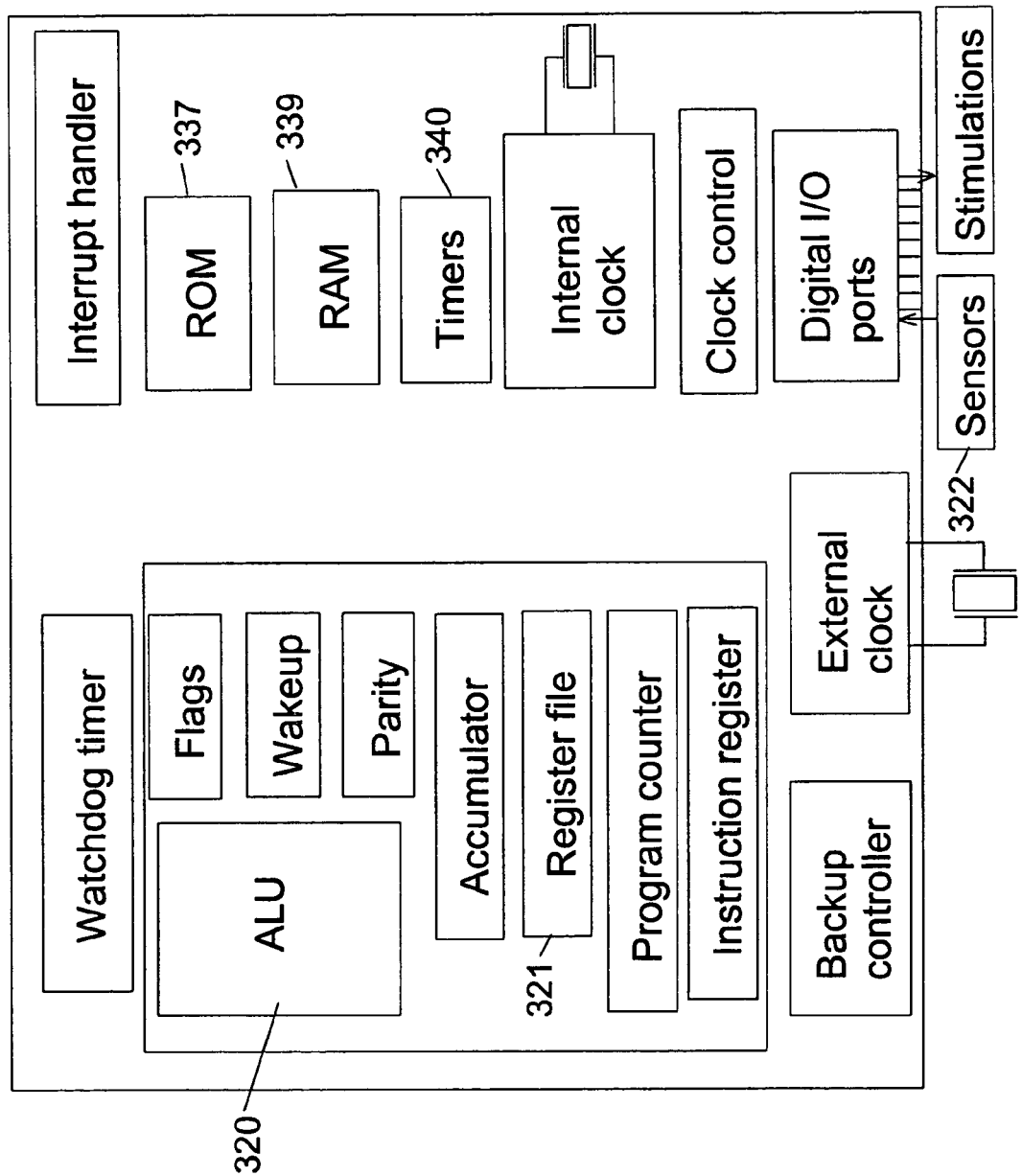

The size of ROM 337 and RAM 339 units are selected based on the requirements of the algorithms and the parameters to be stored. The number of registers in the register file 321 are decided based upon the complexity of computation and the required number of intermediate values. Timers 340 of different precision are used to measure the elapsed intervals. Even though this embodiment does not have external sensors to control timing, future embodiments may have sensors 322 to effect the timing as shown in conjunction with FIG. 31B.

In this embodiment, the two main components of microprocessor are the datapath and control. The datapath performs the arithmetic operation and the control directs the datapath, memory, and I/O devices to execute the instruction of the program. The hardware components of the microprocessor are designed to execute a set of simple instructions. In general the complexity of the instruction set determines the complexity of datapth elements and controls of the microprocessor.

In this embodiment, the microprocessor is provided with a fixed operating routine. Future embodiments may be provided with the capability of actually introducing program changes in the implanted pulse generator. The instruction set of the microprocessor, the size of the register files, RAM 339 and ROM 337 are selected based on the performance needed and the type of the algorithms used. In this application of pulse generator, in which several algorithms can be loaded and modified, Reduced Instruction Set Computer (RISC) architecture is useful. RISC architecture offers advantages because it can be optimized to reduce the instruction cycle which in turn reduces the run time of the program and hence the current drain. The simple instruction set architecture of RISC and its simple hardware can be used to implement any algorithm without much difficulty. Since size is also a major consideration, an 8-bit microprocessor is used for the purpose. As most of the arithmetic calculation are based on a few parameters and are rather simple, an accumulator architecture is used to save bits from specifying registers. Each instruction is executed in multiple clock cycles, and the clock cycles are broadly classified into five stages: an instruction fetch, instruction decode, execution, memory reference, and write back stages. Depending on the type of the instruction, all or some of these stages are executed for proper completion.

Initially, an optimal instruction set architecture is selected based on the algorithm to be implemented and also taking into consideration the special needs of a microprocessor based implanted pulse generator (IPG). The instructions are broadly classified into Load/store instructions, Arithmetic and logic instructions (ALU), control instructions and special purpose instructions.

The instruction format is decided based upon the total number of instructions in the instruction set. The instructions fetched from memory are 8 bits long in this example. Each instruction has an opcode field (2 bits), a register specifier field (3-bits), and a 3-bit immediate field. The opcode field indicates the type of the instruction that was fetched. The register specifier indicates the address of the register in the register file on which the operations are performed. The immediate field is shifted and sign extended to obtain the address of the memory location in load/store instruction. Similarly, in branch and jump instruction, the offset field is used to calculate the address of the memory location the control needs to be transferred to.

Figure 32A:
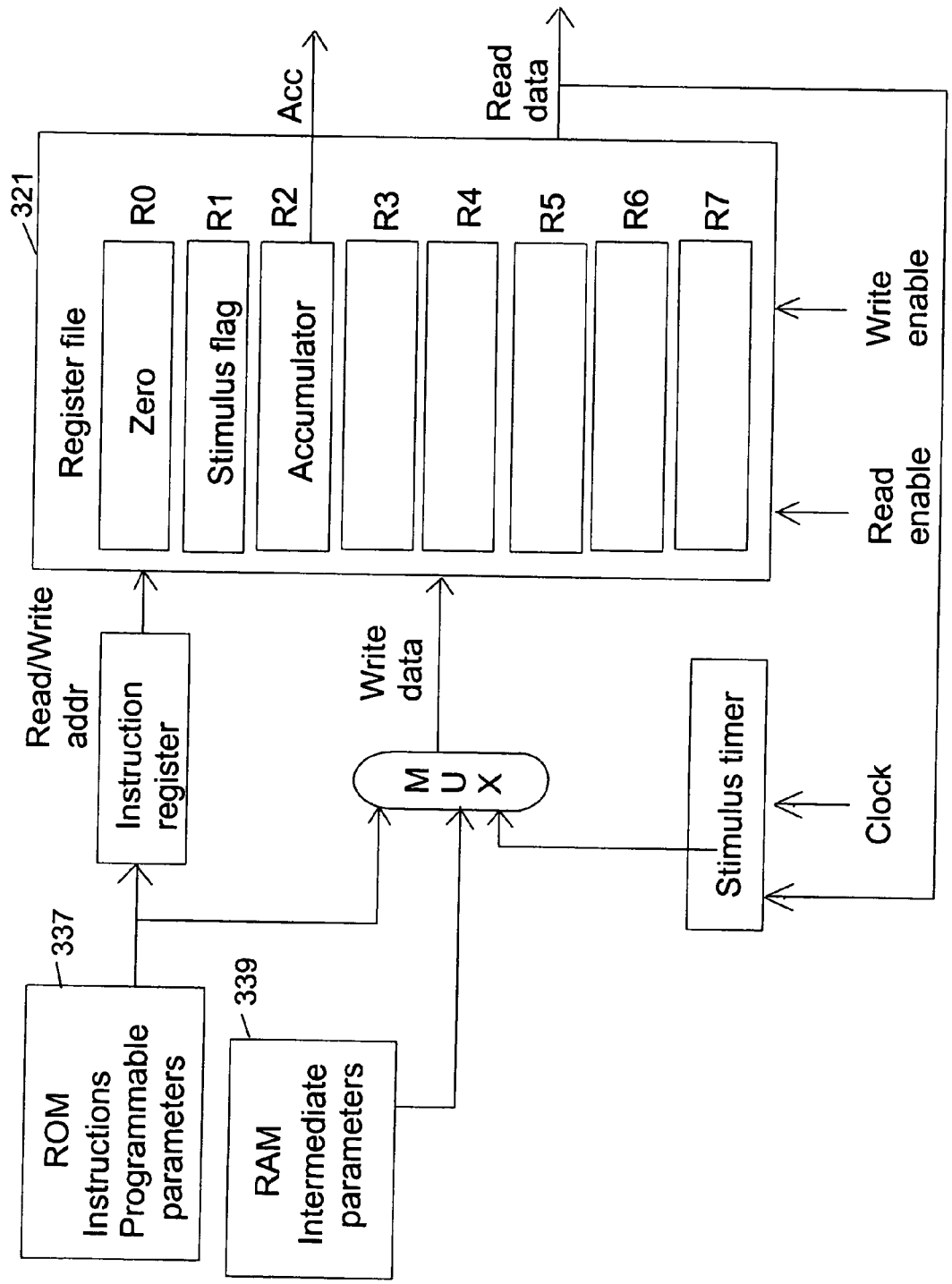
FIG. 32A shows a schematic diagram of the register file, timers and ROM/RAM.

Shown in conjunction with FIG. 32A, the register file 321, which is a collection of registers in which any register can be read from or written to specifying the number of the register in the file. Based on the requirements of the design, the size of the register file is decided. For the purposes of implementation of stimulation pulses algorithms, a register file of eight registers is sufficient, with three special purpose register (0-2) and five general purpose registers (3-7), as shown in FIG. 32A. Register "0" always holds the value "zero". Register "1" is dedicated to the pulse flags. Register "2" is an accumulator in which all the arithmetic calculations are performed. The read/write address port provides a 3-bit address to identify the register being read or written into. The write data port provides 8-bit data to be written into the registers either from ROM/RAM or timers. Read enable control, when asserted enables the register file to provide data at the read data port. Write enable control enables writing of data being provided at the write data port into a register specified by the read/write address.

Generally, two or more timers are required to implement the algorithm for the IPG 391. The timers are read and written into just as any other memory location. The timers are provided with read and write enable controls.

The arithmetic logic unit 320 is an important component of the microprocessor. It performs the arithmetic operation such as addition, subtraction and logical operations such as AND and OR. The instruction format of ALU instructions consists of an opcode field (2 bits), a function field (2 bits) to indicate the function that needs to be performed, and a register specifier (3 bits) or an immediate field (4 bits) to provide an operand.

Figure 32B:
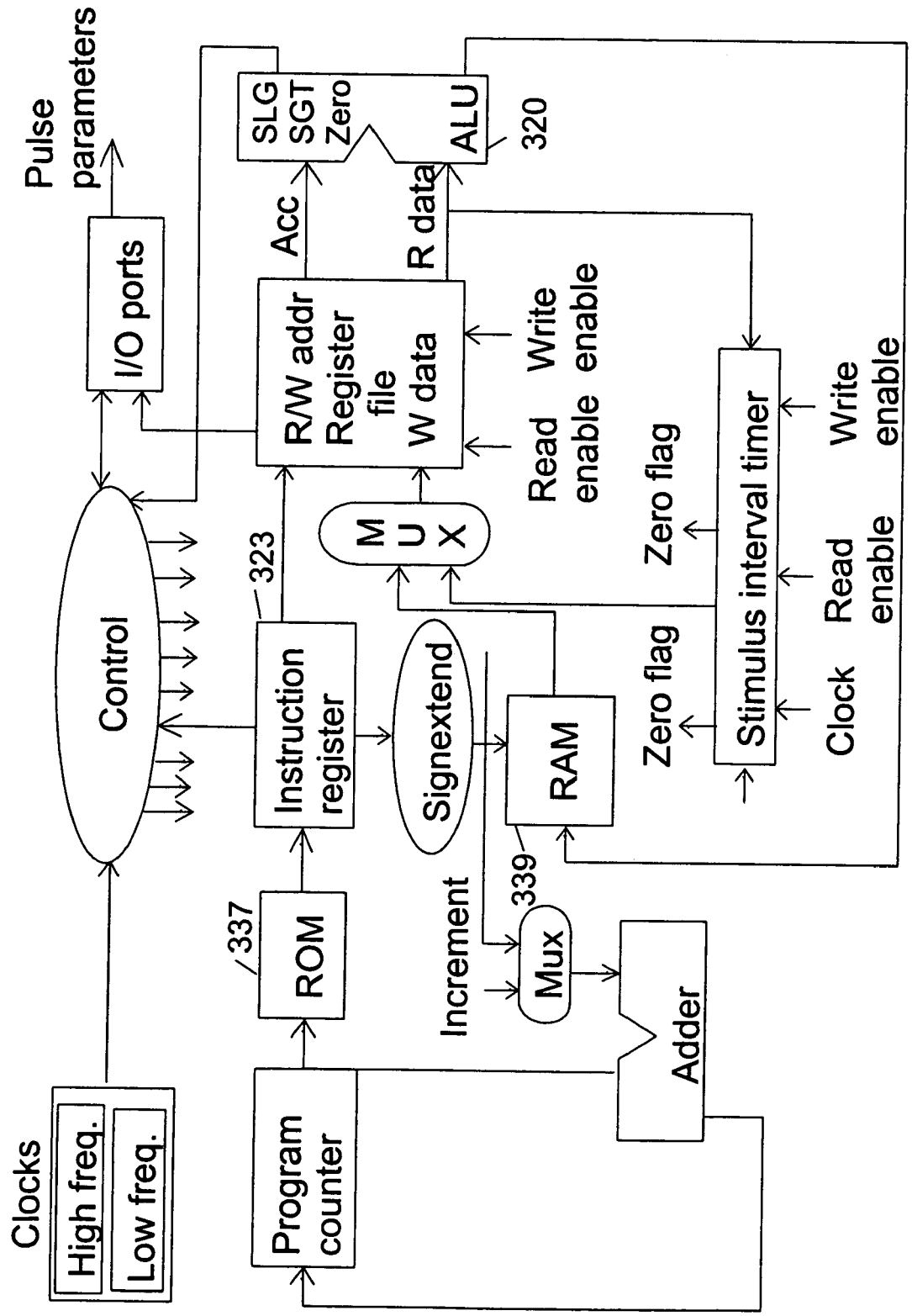
FIG. 32B shows datapath and control of custom-designed microprocessor based pulse generator.

The hardware components discussed above constitute the important components of a datapath. Shown in conjunction with FIG. 32B, there are some special purpose registers such a program counter (PC) to hold the address of the instruction being fetched from ROM 337 and instruction register (IR) 323, to hold the instruction that is fetched for further decoding and execution. The program counter is incremented in each instruction fetch stage to fetch sequential instruction from memory. In the case of a branch or jump instruction, the PC multiplexer allows to choose from the incremented PC value or the branch or jump address calculated. The opcode of the instruction fetched is provided to the control unit to generate the appropriate sequence of control signals, enabling data flow through the datapath. The register specification field of the instruction is given as read/write address to the register file, which provides data from the specified field on the read data port. One port of the ALU is always provided with the contents of the accumulator and the other with the read data port. This design is therefore referred to as accumulator-based architecture. The sign-extended offset is used for address calculation in branch and jump instructions. The timers are used to measure the elapsed interval and are enabled to count down on a low-frequency clock. The timers are read and written into, just as any other memory location (FIG. 32B).

In a multicycle implementation, each stage of instruction execution takes one clock cycle. Since the datapath takes multiple clock cycles per instruction, the control must specify the signals to be asserted in each stage and also the next step in the sequence. This can be easily implemented as a finite state machine.

A finite state machine consists of a set of states and directions on how to change states. The directions are defined by a next-state function, which maps the current state and the inputs to a new state. Each stage also indicates the control signals that need to be asserted. Every state in the finite state machine takes one clock cycle. Since the instruction fetch and decode stages are common to all the instruction, the initial two states are common to all the instruction. After the execution of the last step, the finite state machine returns to the fetch state.

A finite state machine can be implemented with a register that holds the current stage and a block of combinational logic such as a PLA. It determines the datapath signals that need to be asserted as well as the next state. A PLA is described as an array of AND gates followed by an array of OR gates. Since any function can be computed in two levels of logic, the two-level logic of PLA is used for generating control signals.

The occurrence of a wakeup event initiates a stored operating routine corresponding to the event. In the time interval between a completed operating routine and a next wake up event, the internal logic components of the processor are deactivated and no energy is being expended in performing an operating routine.

A further reduction in the average operating current is obtained by providing a plurality of counting rates to minimize the number of state changes during counting cycles. Thus intervals which do not require great precision, may be timed using relatively low counting rates, and intervals requiring relatively high precision, such as stimulating pulse width, may be timed using relatively high counting rates.

Figure 33:
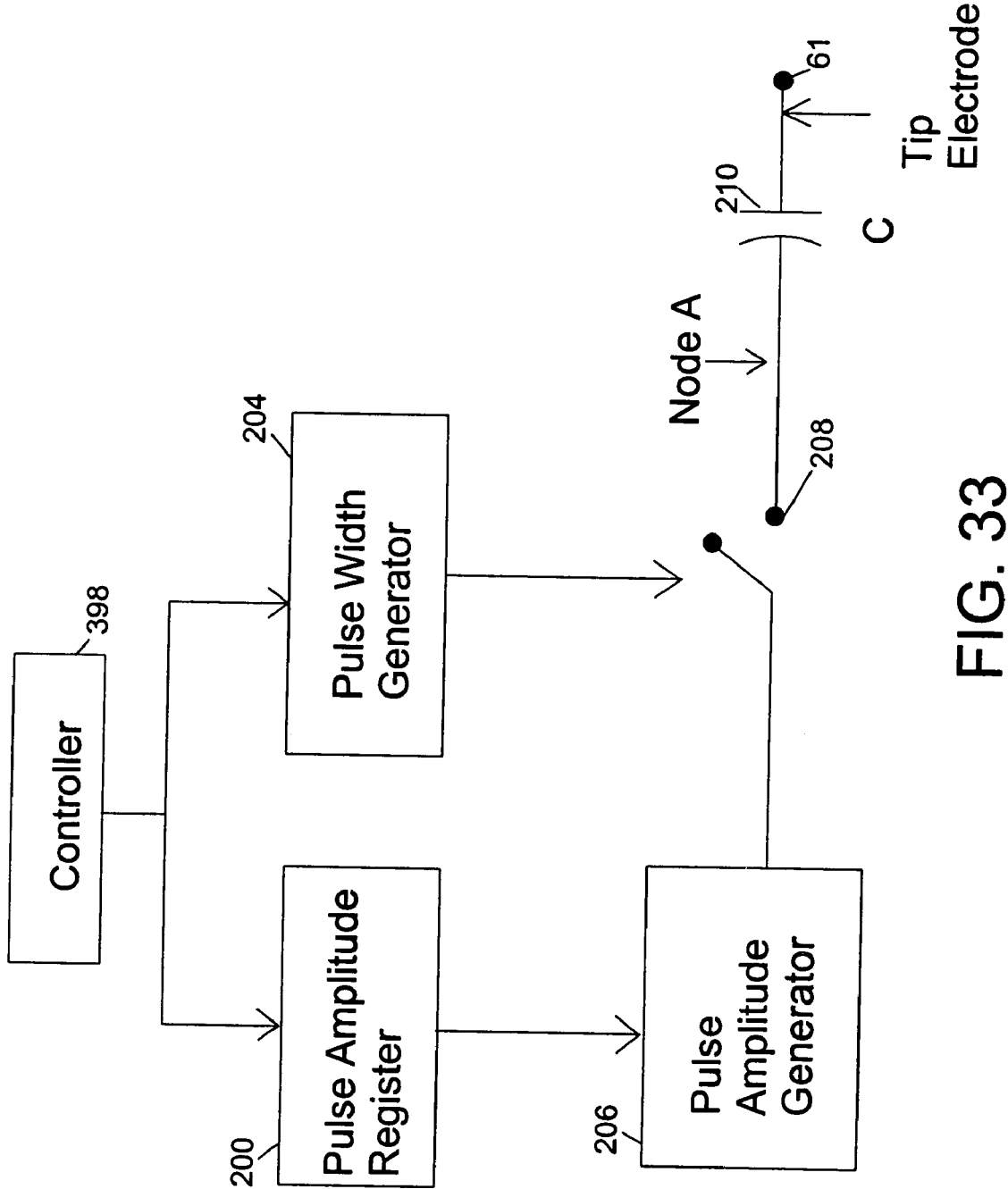
FIG. 33 is a block diagram for generation of a predetermined stimulation pulse.

The logic and control unit 398 of the IPG controls the output amplifiers. The pulses have predetermined energy (pulse amplitude and pulse width) and are delivered at a time determined by the therapy stimulus controller. The circuitry in the output amplifier, shown in conjunction with (FIG. 33) generates an analog voltage or current that represents the pulse amplitude. The stimulation controller module initiates a stimulus pulse by closing a switch 208 that transmits the analog voltage or current pulse to the nerve tissue through the tip electrode 61 of the lead 40. The output circuit receiving instructions from the stimulus therapy controller 398 that regulates the timing of stimulus pulses and the amplitude and duration (pulse width) of the stimulus. The pulse amplitude generator 206 determines the configuration of charging and output capacitors necessary to generate the programmed stimulus amplitude. The output switch 208 is closed for a period of time that is controlled by the pulse width generator 204. When the output switch 208 is closed, a stimulus is delivered to the tip electrode 61 of the lead 40.

Figure 34:
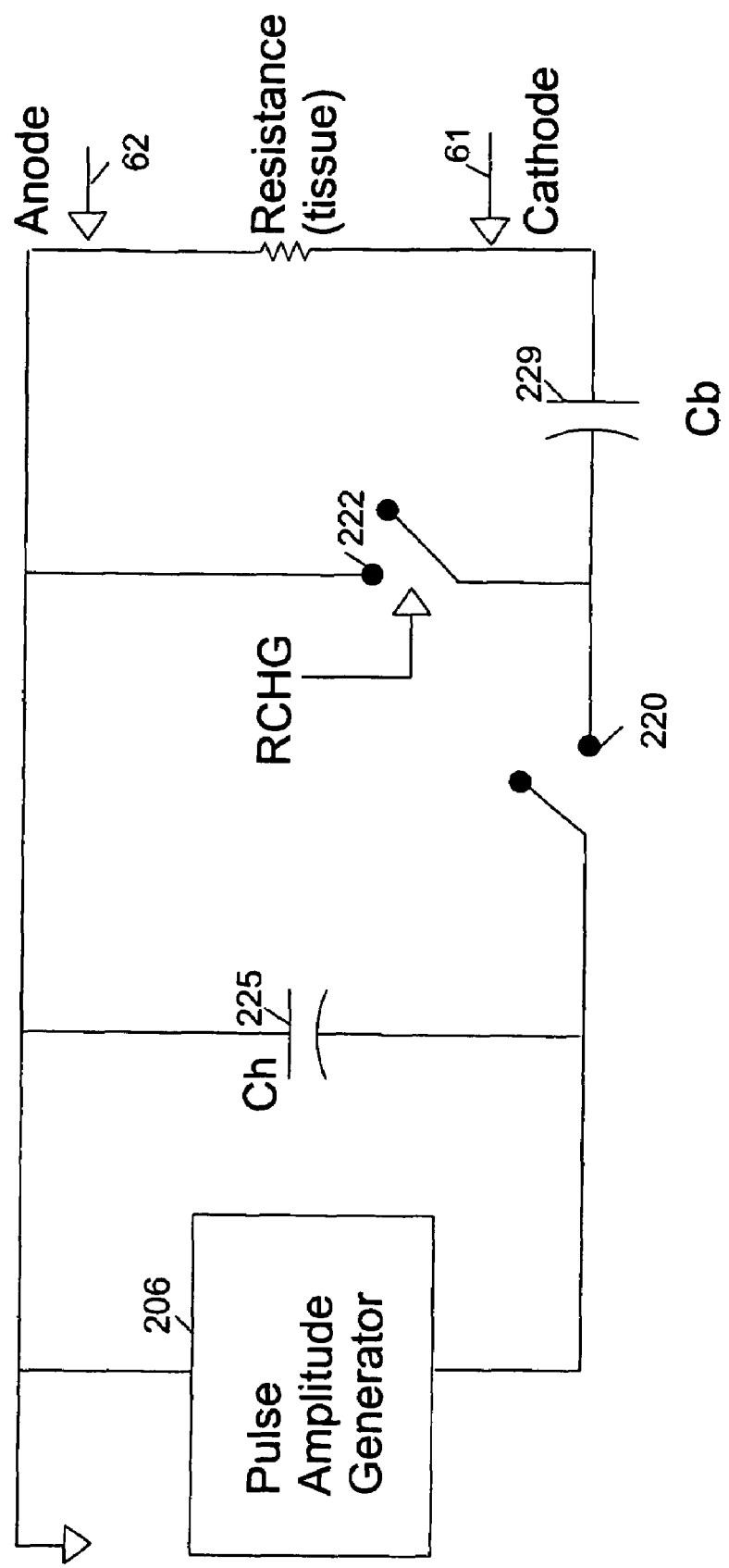
FIG. 34 is a simplified schematic for delivering stimulation pulses.

The constant-voltage output amplifier applies a voltage pulse to the distal electrode (cathode) 61 of the lead 40. A typical circuit diagram of a voltage output circuit is shown in FIG. 34. This configuration contains a stimulus amplitude generator 206 for generating an analog voltage. The analog voltage represents the stimulus amplitude and is stored on a holding capacitor $C_h$ 225. Two switches are used to deliver the stimulus pulses to the lead 40, a stimulating delivery switch 220, and a recharge switch 222, that reestablishes the charge equilibrium after the stimulating pulse has been delivered to the nerve tissue. Since these switches have leakage currents that can cause direct current (DC) to flow into the lead system 40, a DC blocking capacitor $C_b$ 229, is included. This is to prevent any possible corrosion that may result from the leakage of current in the lead 40. When the stimulus delivery switch 220 is closed, the pulse amplitude analog voltage stored in the ($C_h$ 225) holding capacitor is transferred to the cathode electrode 61 of the lead 40 through the coupling capacitor, $C_b$ 229. At the end of the stimulus pulse, the stimulus delivery switch 220 opens. The pulse duration being the interval from the closing of the switch 220 to its reopening. During the stimulus delivery, some of the charge stored on $C_h$ 225 has been transferred to $C_b$ 229, and some has been delivered to the lead system 40 to stimulate the nerve tissue.

To re-establish equilibrium, the recharge switch 222 is closed, and a rapid recharge pulse is delivered. This is intended to remove any residual charge remaining on the coupling capacitor $C_b$ 229, and the stimulus electrodes on the lead (polarization). Thus, the stimulus is delivered as the result of closing and opening of the stimulus delivery 220 switch and the closing and opening of the RCHG switch 222. At this point, the charge on the holding $C_h$ 225 must be replenished by the stimulus amplitude generator 206 before another stimulus pulse can be delivered.

The pulse generating unit charges up a capacitor and the capacitor is discharged when the control (timing) circuitry requires the delivery of a pulse. This embodiment utilizes a constant voltage pulse generator, even though a constant current pulse generator can also be utilized. Pump-up capacitors are used to deliver pulses of larger magnitude than the potential of the batteries. The pump up capacitors are charged in parallel and discharged into the output capacitor in series. Shown in conjunction with FIG. 35 is a circuit diagram of a voltage doubler which is shown here as an example. For higher multiples of battery voltage, this doubling circuit can be cascaded with other doubling circuits. As shown in FIG. 35, during phase I (top of FIG. 35), the pump capacitor $C_p$ is charged to $V_{bat}$ and the output capacitor $C_o$ supplies charge to the load. During phase II, the pump capacitor charges the output capacitor, which is still supplying the load current. In this case, the voltage drop across the output capacitor is twice the battery voltage.

Figure 36:
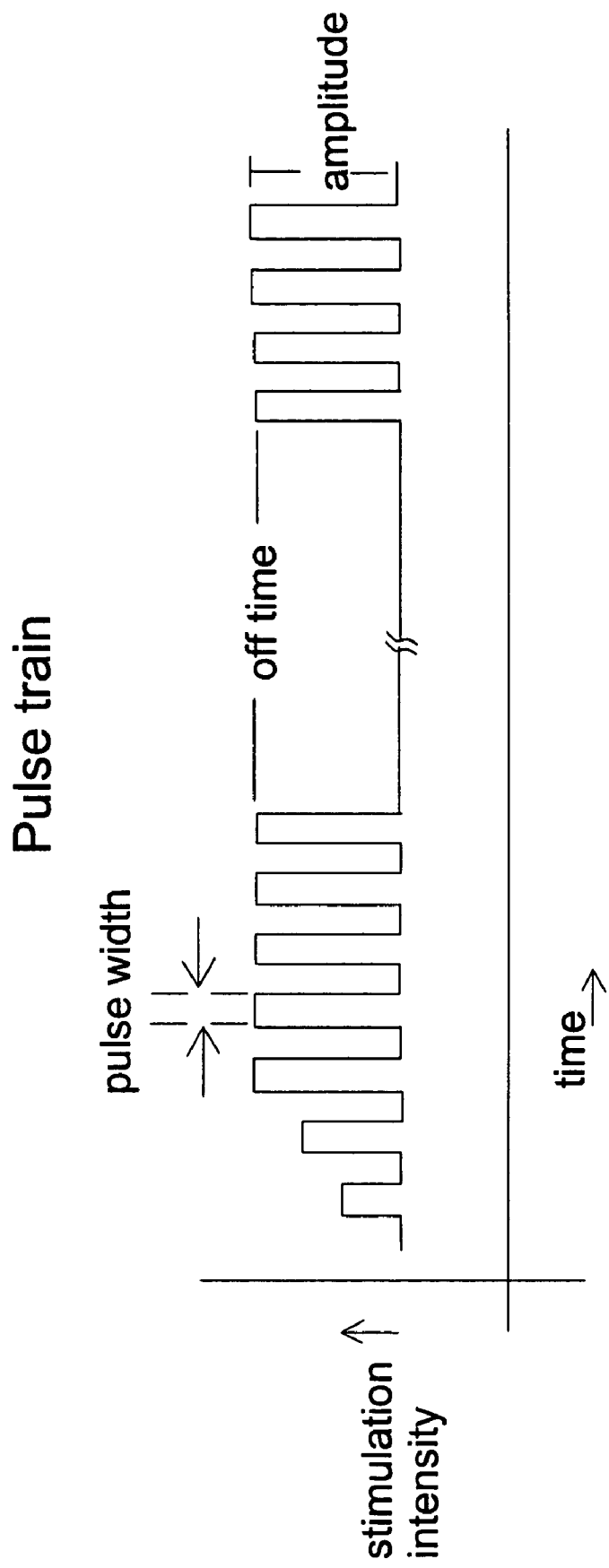
FIG. 36 is a diagram depicting ramping-up of a pulse train.

FIG. 36 shows an example of the pulse trains that are delivered with this embodiment. The microcontroller is configured to deliver the pulse train as shown in the figure, i.e. there is "ramping up" of the pulse train. The purpose of the ramping-up is to avoid sudden changes in stimulation, when the pulse train begins.

Figure 37:
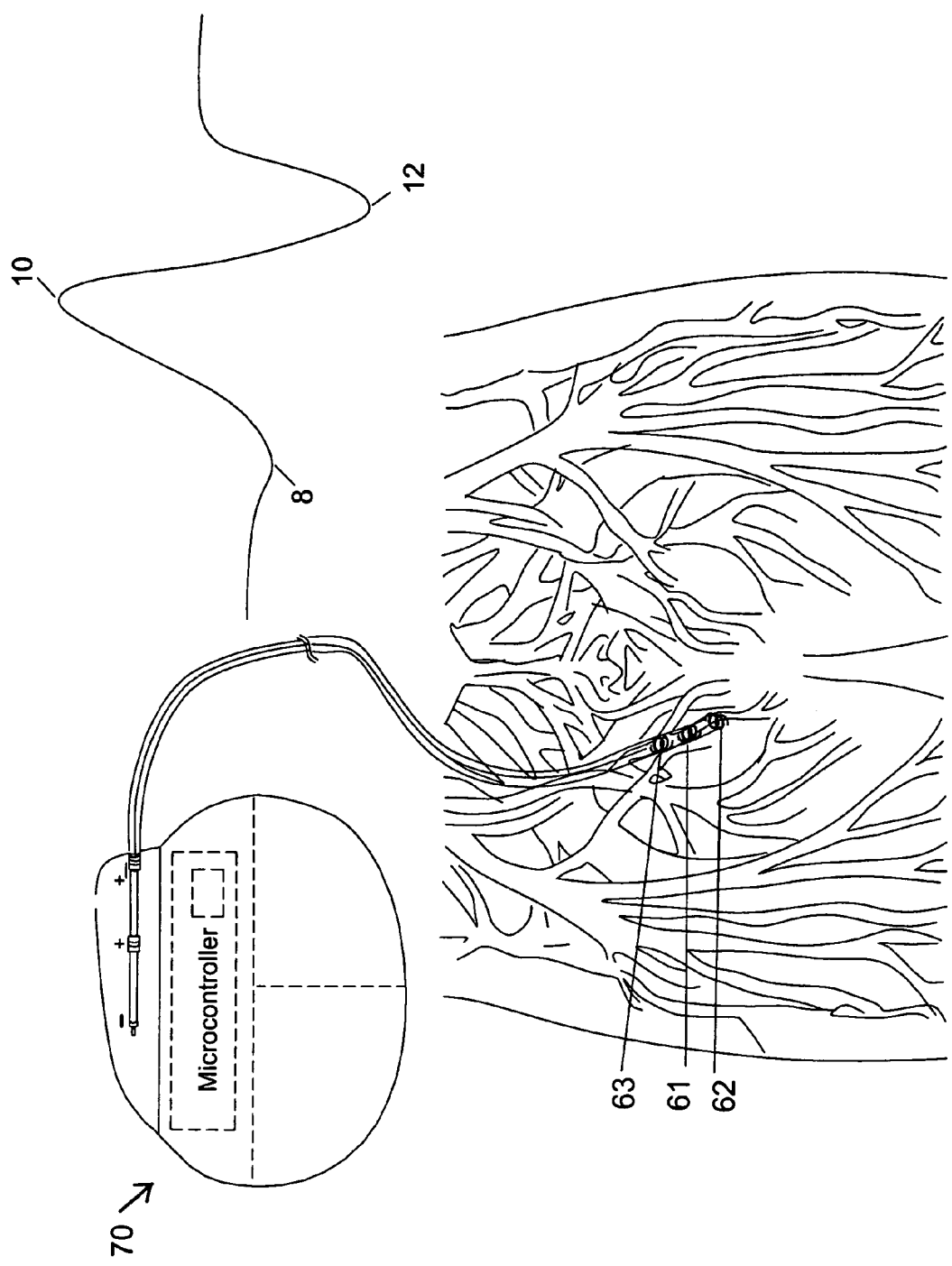
FIG. 37 depicts an implantable system with tripolar lead for selective unidirectional blocking of nerve stimulation.
Figure 39:
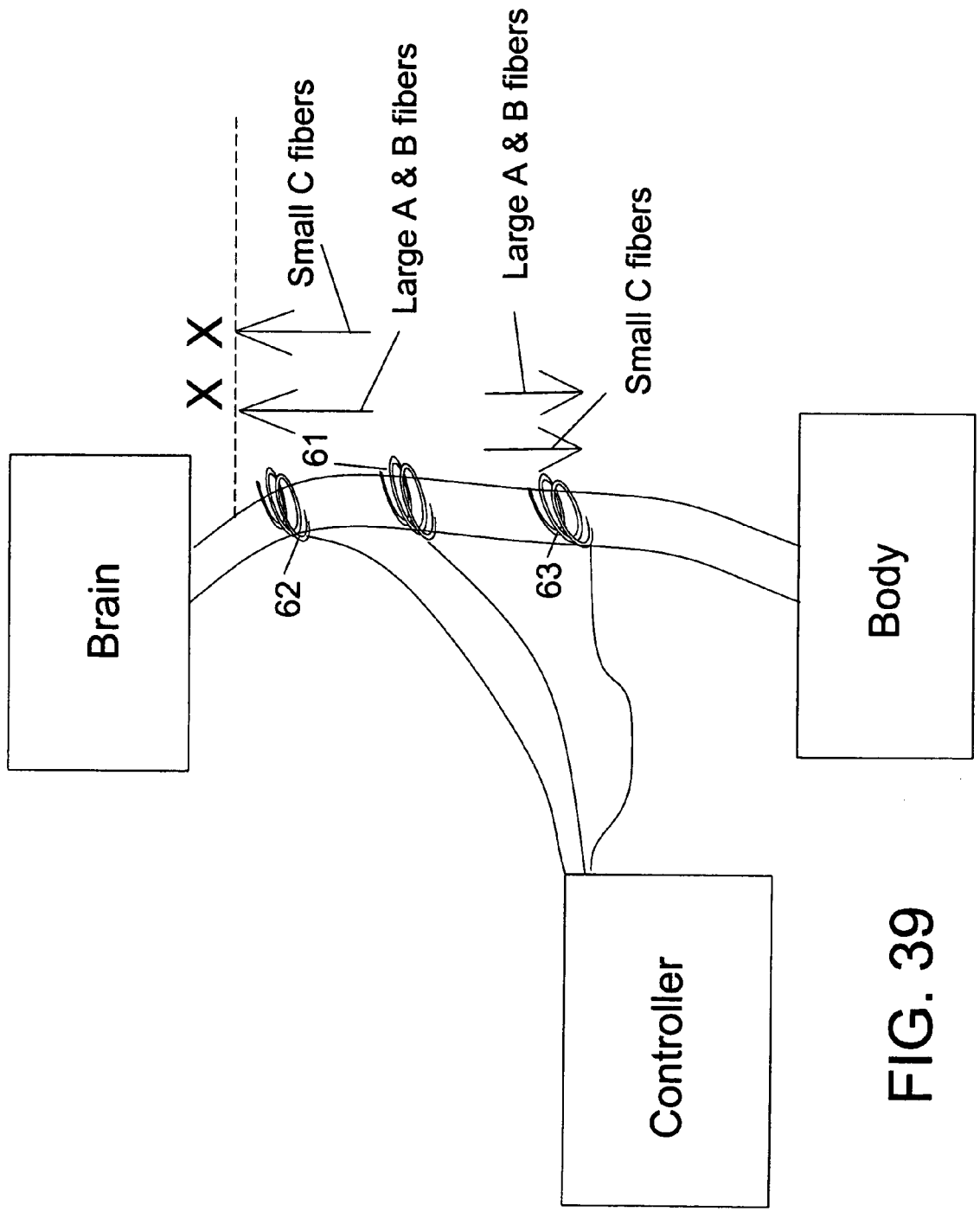
FIG. 39 depicts selective unidirectional blocking with nerve stimulation.

In one aspect of the invention, the electrical stimulation can be supplied uni-directionally and substantially blocked in the other direction, utilizing the "greenwave" effect. In such a case, as shown in conjunction with FIGS. 37 and 39, a tripolar lead is utilized. As depicted on the top right portion of FIG. 37, a depolarization peak 10 on the nerve bundle corresponding to electrode 61 (cathode) and the two hyper-polarization peaks 8, 12 corresponding to electrodes 62, 63 (anodes). With the microcontroller controlling the tripolar device, the size and timing of the hyper-polarizations 8, 12 can be controlled. As shown in conjunction with FIG. 38, since the speed of conduction is different between the larger diameter A and B fibers and the smaller diameter c-fibers, by appropriately timing the pulses, collision blocks can be created for conduction via the large diameter A and B fibers in the afferent direction. This is depicted schematically in FIG. 39. A number of blocking techniques are known in the art, such as collision blocking, high frequency blocking, and anodal blocking. Any of these well known blocking techniques may be used with the practice of this invention, and are considered within the scope of this invention.

The programming of the implanted pulse generator (IPG) 391 is shown in conjunction with FIGS. 40A and 40B. With the magnetic Reed Switch 389 (FIGS. 28, 42) in the closed position, a coil in the head of the programmer 85, communicates with a telemetry coil 399 of the implanted pulse generator 391. Bi-directional inductive telemetry is used to exchange data with the implanted unit 391 by means of the external programming unit 85.

The transmission of programming information involves manipulation of the carrier signal in a manner that is recognizable by the pulse generator 391 as a valid set of instructions. The process of modulation serves as a means of encoding the programming instruction in a language that is interpretable by the implanted pulse generator 391. Modulation of signal amplitude, pulse width, and time between pulses are all used in the programming system, as will be appreciated by those skilled in the art. FIG. 41A shows an example of pulse count modulation, and FIG. 41B shows an example of pulse width modulation, that can be used for encoding.

Figure 42:
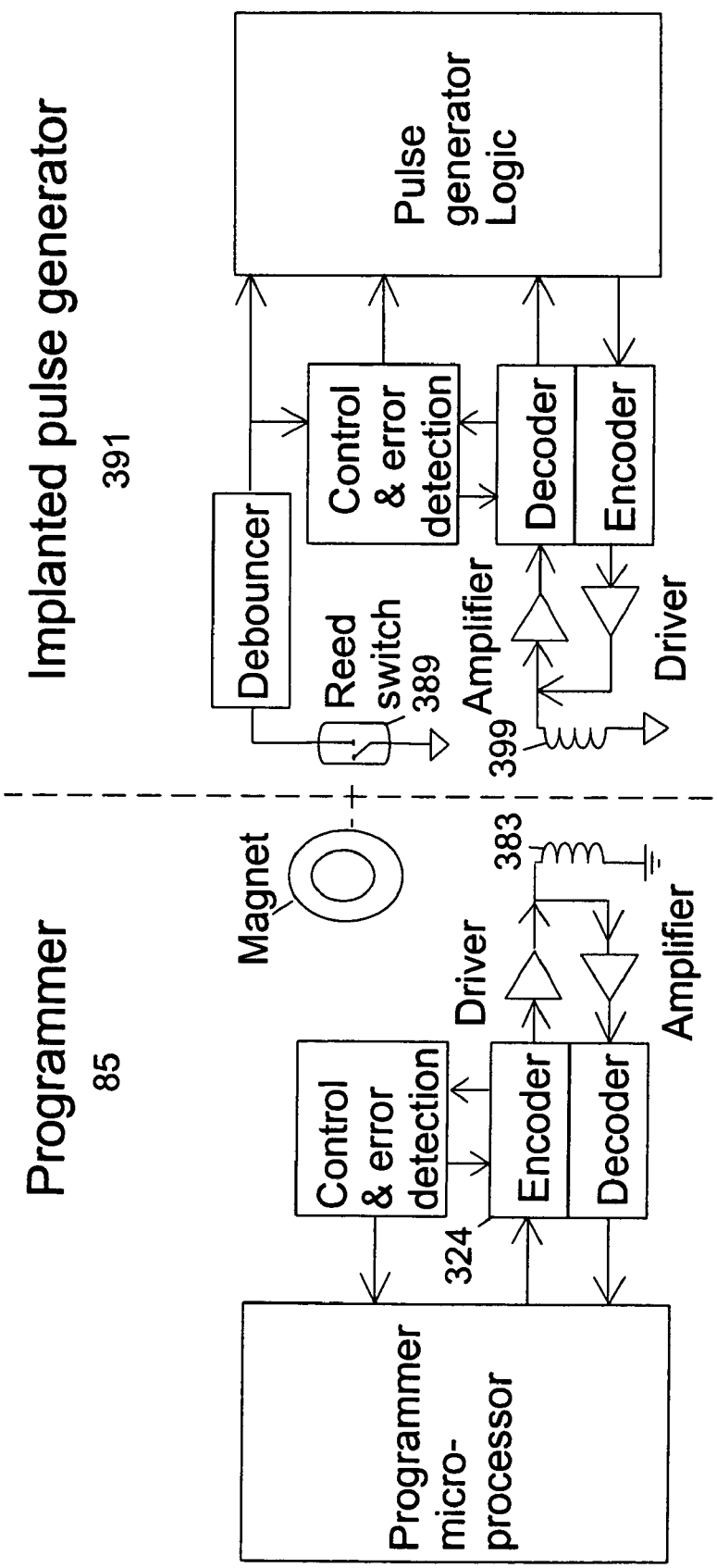
FIG. 42 is a simplified overall block diagram of implanted pulse generator (IPG) programmer.

FIG. 42 shows a simplified overall block diagram of the implanted pulse generator (IPG) 391 programming and telemetry interface. The left half of FIG. 42 is programmer 85 which communicates programming and telemetry information with the IPG 391. The sections of the IPG 391 associated with programming and telemetry are shown on the right half of FIG. 42. In this case, the programming sequence is initiated by bringing a permanent magnet in the proximity of the IPG 391 which closes a reed switch 389 in the IPG 391. Information is then encoded into a special error-correcting pulse sequence and transmitted electromagnetically through a set of coils. The received message is decoded, checked for errors, and passed on to the unit's logic circuitry. The IPG 391 of this embodiment includes the capability of bi-directional communication.

The reed switch 389 is a magnetically-sensitive mechanical switch, which consists of two thin strips of metal (the "reed") which are ferromagnetic. The reeds normally spring apart when no magnetic field is present. When a field is applied, the reeds come together to form a closed circuit because doing so creates a path of least reluctance. The programming head of the programmer contains a high-field-strength ceramic magnet.

When the switch closes, it activates the programming hardware, and initiates an interrupt of the IPG central processor. Closing the reed switch 389 also presents the logic used to encode and decode programming and telemetry signals. A nonmaskable interrupt (NMI) is sent to the IPG processor, which then executes special programming software. Since the NMI is an edge-triggered signal and the reed switch is vulnerable to mechanical bounce, a debouncing circuit is used to avoid multiple interrupts. The overall current consumption of the IPG increases during programming because of the debouncing circuit and other communication circuits.

A coil 399 is used as an antenna for both reception and transmission. Another set of coils 383 is placed in the programming head, a relatively small sized unit connected to the programmer 85. All coils are tuned to the same resonant frequency. The interface is half-duplex with one unit transmitting at a time.

Figure 43:
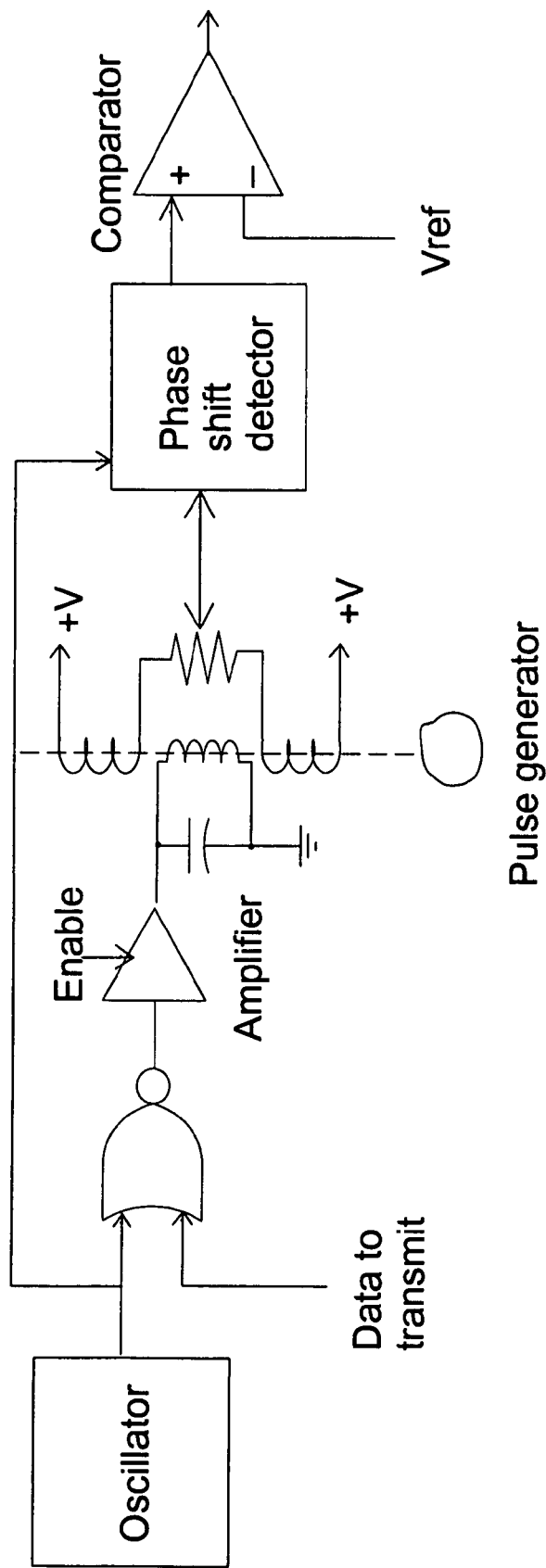
FIG. 43 shows a programmer head positioning circuit.

Since the relative positions of the programming head 87 and IPG 391 determine the coupling of the coils, this embodiment utilizes a special circuit which has been devised to aid the positioning of the programming head, and is shown in FIG. 43. It operates on similar principles to the linear variable differential transformer. An oscillator tuned to the resonant frequency of the pacemaker coil 399 drives the center coil of a three-coil set in the programmer head. The phase difference between the original oscillator signal and the resulting signal from the two outer coils is measured using a phase shift detector. It is proportional to the distance between the implanted pulse generator and the programmer head. The phase shift, as a voltage, is compared to a reference voltage and is then used to control an indicator such as an LED. An enable signal allows switching the circuit on and off.

Figure 44:
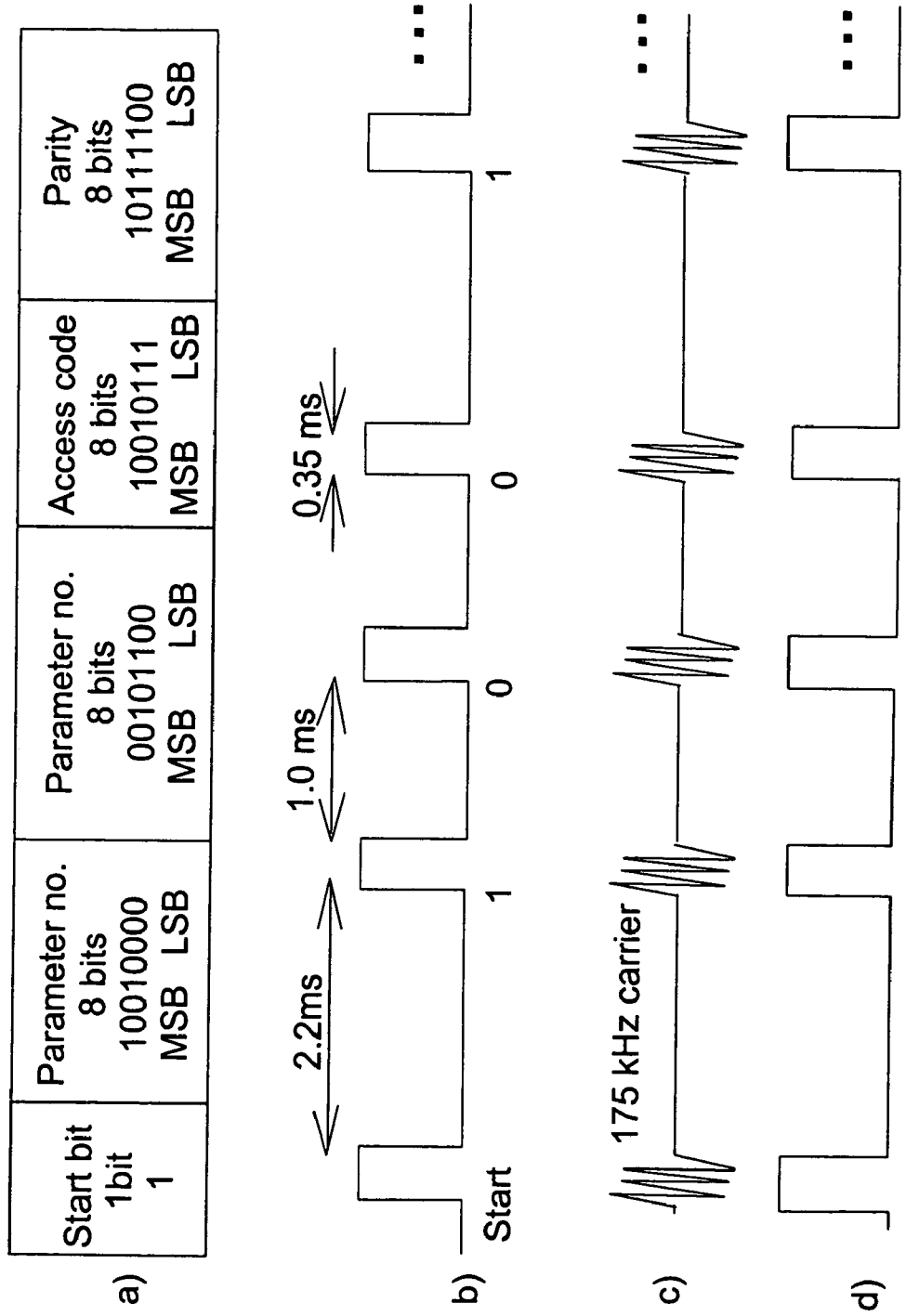
FIG. 44 depicts typical encoding and modulation of programming messages.
Figure 45:
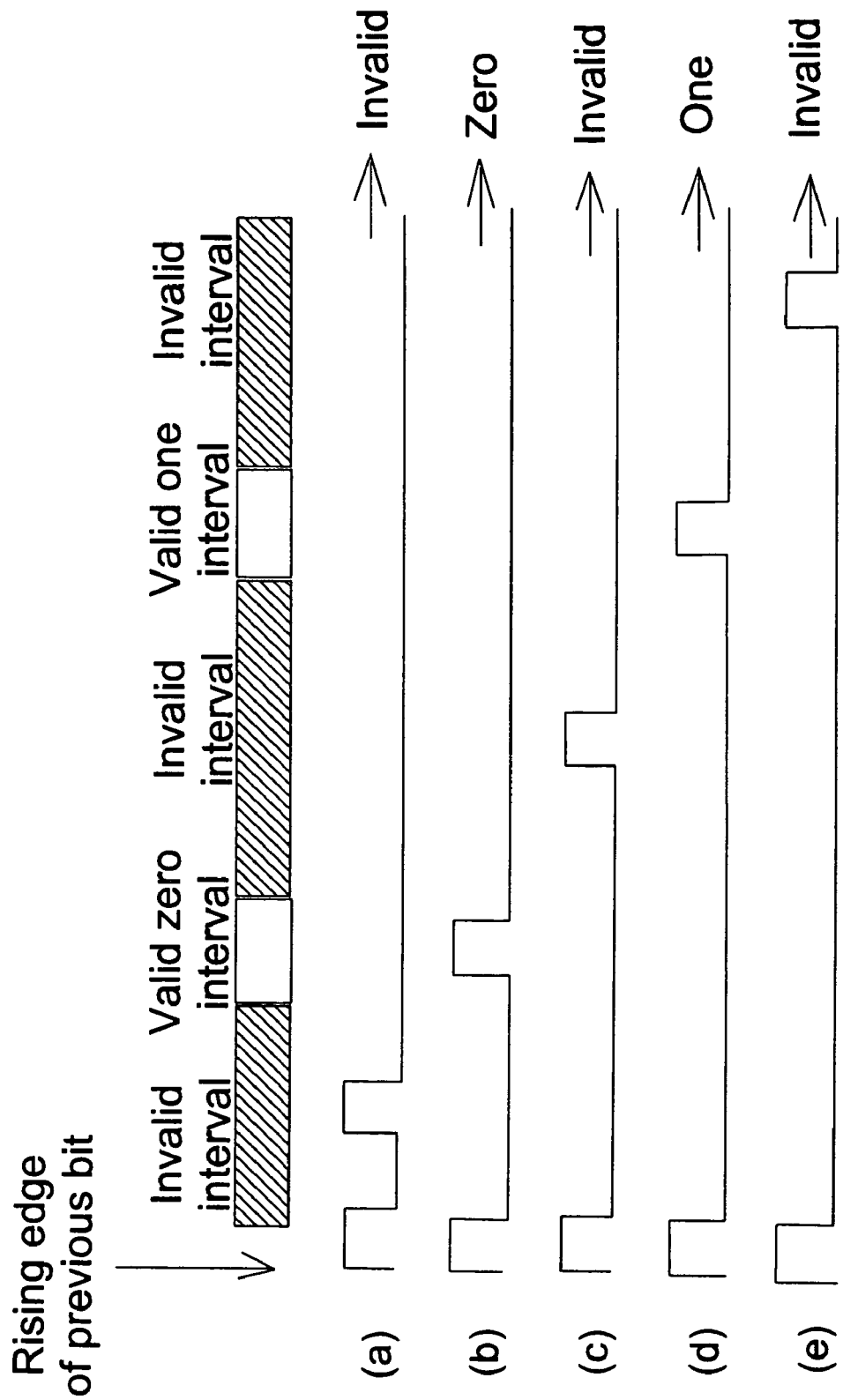
FIG. 45 shows decoding bits of signals.

Actual programming is shown in conjunction with FIGS. 44 and 45. Programming and telemetry messages comprise many bits; however, the coil interface can only transmit one bit at a time. In addition, the signal is modulated to the resonant frequency of the coils, and must be transmitted in a relatively short period of time, and must provide detection of erroneous data.

A programming message is comprised of five parts FIG. 44(a). The start bit indicates the beginning of the message and is used to synchronize the timing of the rest of the message. The parameter number specifies which parameter (e.g., mode, pulse width, delay) is to be programmed. In the example, in FIG. 44(a) the number 10010000 specifies the pulse rate to be specified. The parameter value represents the value that the parameter should be set to. This value may be an index into a table of possible values; for example, the value 00101100 represents a pulse stimulus rate of 80 pulses/min. The access code is a fixed number based on the stimulus generator model which must be matched exactly for the message to succeed. It acts as a security mechanism against use of the wrong programmer, errors in the message, or spurious programming from environmental noise. It can also potentially allow more than one programmable implant in the patient. Finally, the parity field is the bitwise exclusive-OR of the parameter number and value fields. It is one of several error-detection mechanisms.

All of the bits are then encoded as a sequence of pulses of 0.35-ms duration FIG. 44(b). The start bit is a single pulse. The remaining bits are delayed from their previous bit according to their bit value. If the bit is a zero, the delay is short (1.0); if it is a one, the delay is long (2.2 ms). This technique of pulse position coding, makes detection of errors easier.

The serial pulse sequence is then amplitude modulated for transmission FIG. 44(c). The carrier frequency is the resonant frequency of the coils. This signal is transmitted from one set of coils to the other and then demodulated back into a pulse sequence FIG. 44(d).

FIG. 45 shows how each bit of the pulse sequence is decoded from the demodulated signal. As soon as each bit is received, a timer begins timing the delay to the next pulse. If the pulse occurs within a specific early interval, it is counted as a zero bit (FIG. 45(b)). If it otherwise occurs with a later interval, it is considered to be a one bit (FIG. 45(d)). Pulses that come too early, too late, or between the two intervals are considered to be errors and the entire message is discarded (FIG. 45(a, c, e)). Each bit begins the timing of the bit that follows it. The start bit is used only to time the first bit.

Telemetry data may be either analog or digital. Digital signals are first converted into a serial bit stream using an encoding such as shown in FIG. 45(b). The serial stream or the analog data is then frequency modulated for transmission.

An advantage of this and other encodings is that they provide multiple forms of error detection. The coils and receiver circuitry are tuned to the modulation frequency, eliminating noise at other frequencies. Pulse-position coding can detect errors by accepting pulses only within narrowly-intervals. The access code acts as a security key to prevent programming by spurious noise or other equipment. Finally, the parity field and other checksums provides a final verification that the message is valid. At any time, if an error is detected, the entire message is discarded.

Another more sophisticated type of pulse position modulation may be used to increase the bit transmission rate. In this, the position of a pulse within a frame is encoded into one of a finite number of values, e.g. 16. A special synchronizing bit is transmitted to signal the start of the frame. Typically, the frame contains a code which specifies the type or data contained in the remainder of the frame.

Figure 46:
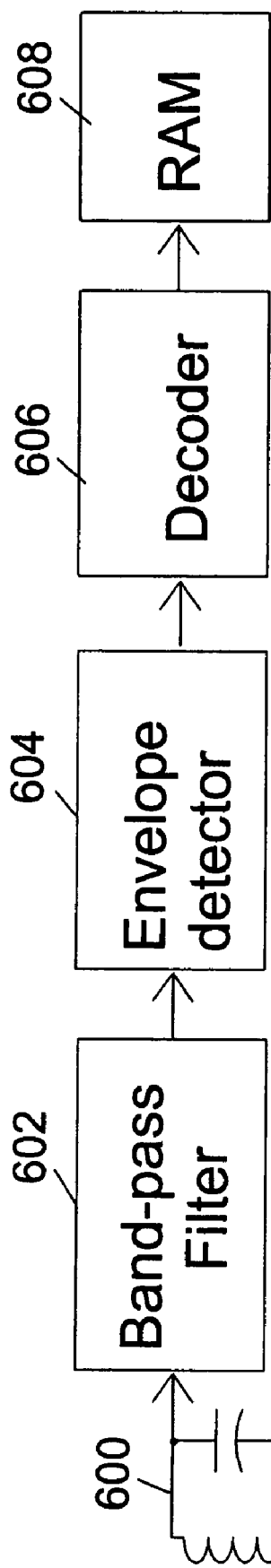
FIG. 46 shows a diagram of receiving and decoding circuitry for programming data.

FIG. 46 shows a diagram of receiving and decoding circuitry for programming data. The IPG coil, in parallel with capacitor creates a tuned circuit for receiving data. The signal is band-pass filtered 602 and envelope detected 604 to create the pulsed signal in FIG. 44(*d*). After decoding, the parameter value is placed in a RAM at the location specified by the parameter number. The IPG can have two copies of the RAM—a permanent set and a temporary set—which makes it easy for the physician to set the IPG to a temporary configuration and later reprogram it back to the usual settings.

Figure 47:
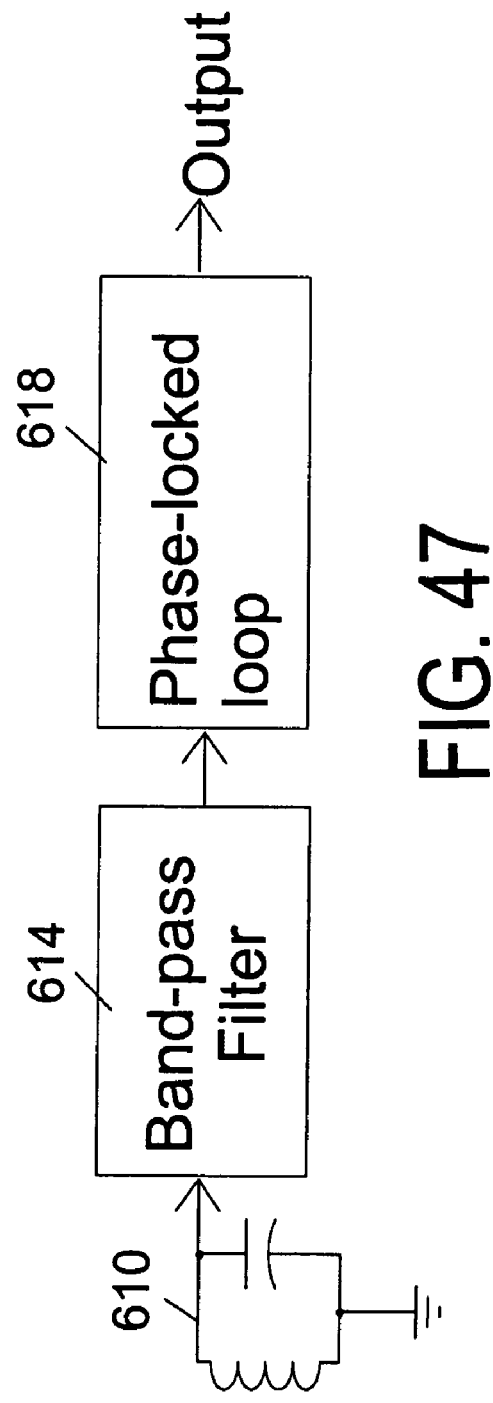
FIG. 47 shows a diagram of receiving and decoding circuitry for telemetry data.

FIG. 47 shows the basic circuit used to receive telemetry data. Again, a coil and capacitor create a resonant circuit tuned to the carrier frequency. The signal is further band-pass filtered 614 and then frequency-demodulated using a phase-locked loop 618.

Figure 48:
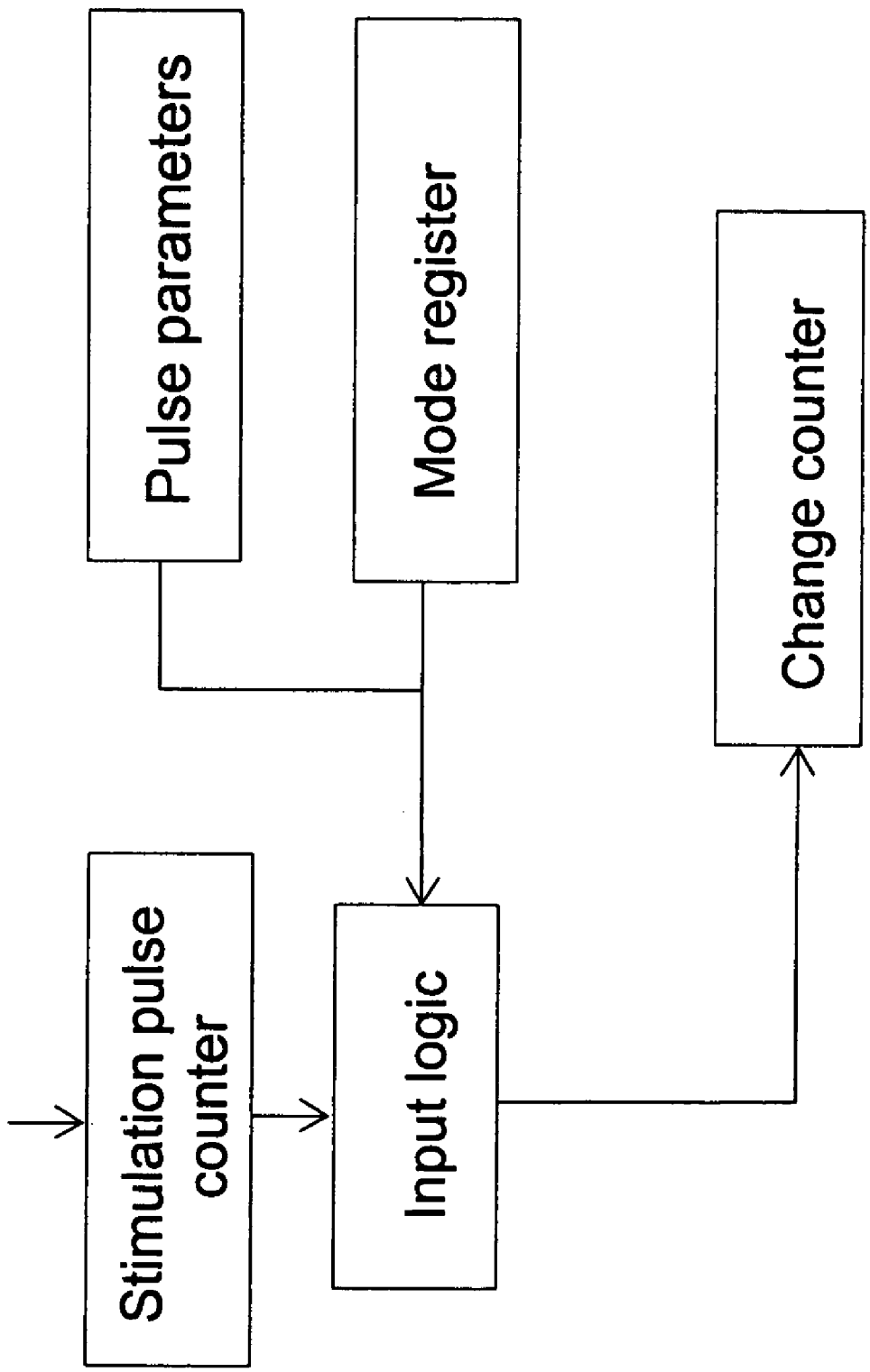
FIG. 48 is a block diagram of a battery status test circuit.

This embodiment also comprises an optional battery status test circuit. Shown in conjunction with FIG. 48, the charge delivered by the battery is estimated by keeping track of the number of pulses delivered by the IPG 391. An internal charge counter is updated during each test mode to read the total charge delivered. This information about battery status is read from the IPG 391 via telemetry.

Combination Implantable Device Comprising both a Stimulus-Receiver and a Programmable Implantable Pulse Generator (IPG)

Figure 49:
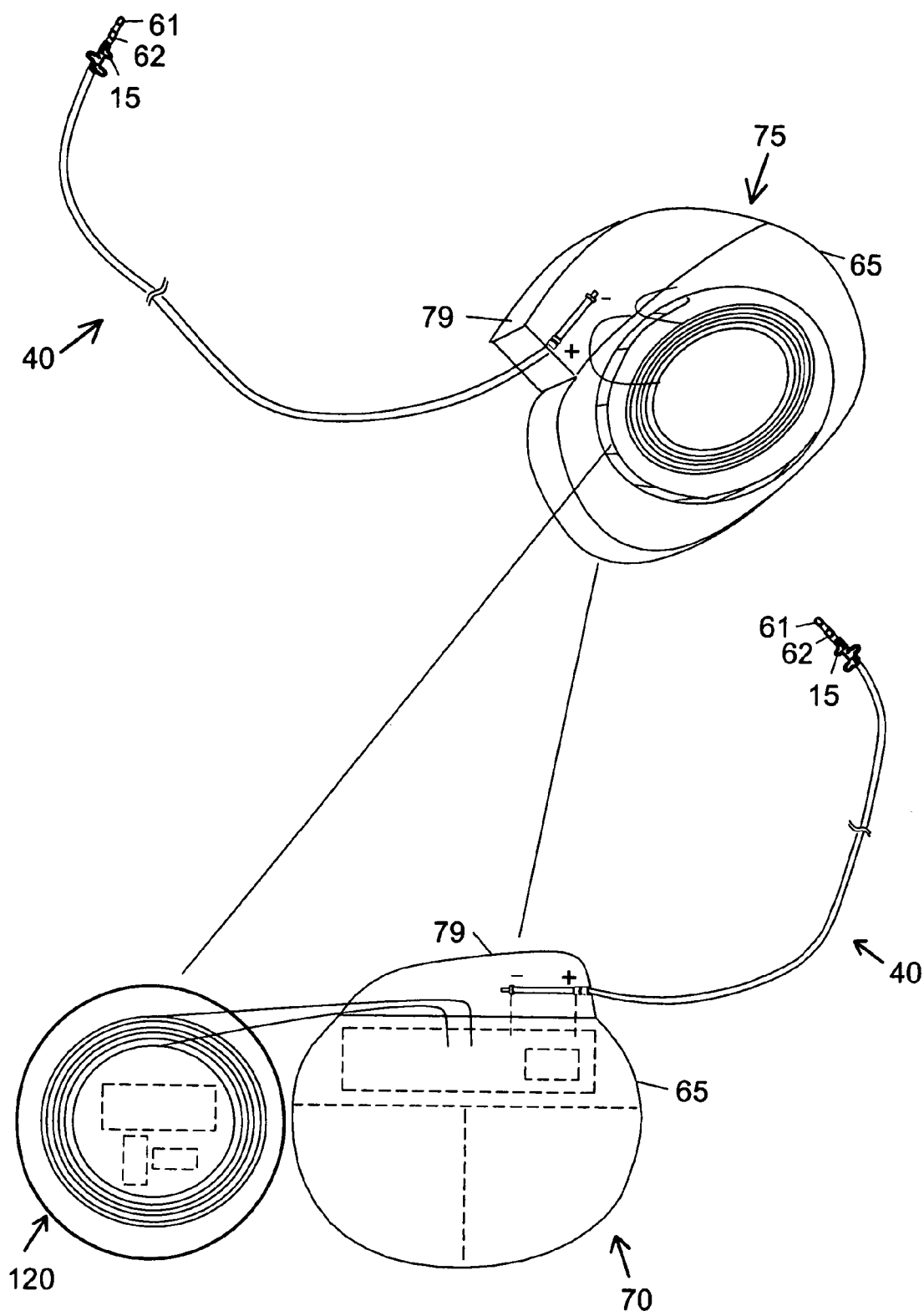
FIG. 49 is a diagram showing the two modules of the implanted pulse generator (IPG).

In one embodiment, the implantable device may comprise both a stimulus-receiver and a programmable implantable pulse generator (IPG). FIG. 49 shows a close up view of the packaging of the implanted stimulator 75 of this embodiment, showing the two subassemblies 120, 70. The two subassemblies are the stimulus-receiver module 120 and the battery operated pulse generator module 70. The external stimulator 42, and programmer 85 also being remotely controllable from a distant location via the internet. Controlling circuitry means within the stimulator 75, makes the inductively coupled stimulator 120 and the IPG 70 operate in harmony with each other. For example, when stimulation is applied via the inductively coupled system, the battery operated portion of the stimulator is triggered to go into the "sleep" mode. Conversely, when programming pulses (which are also inductively coupled) are being applied to the implanted battery operated pulse generator 70, the inductively coupled stimulation circuitry 120 is disconnected.

Figure 52A:
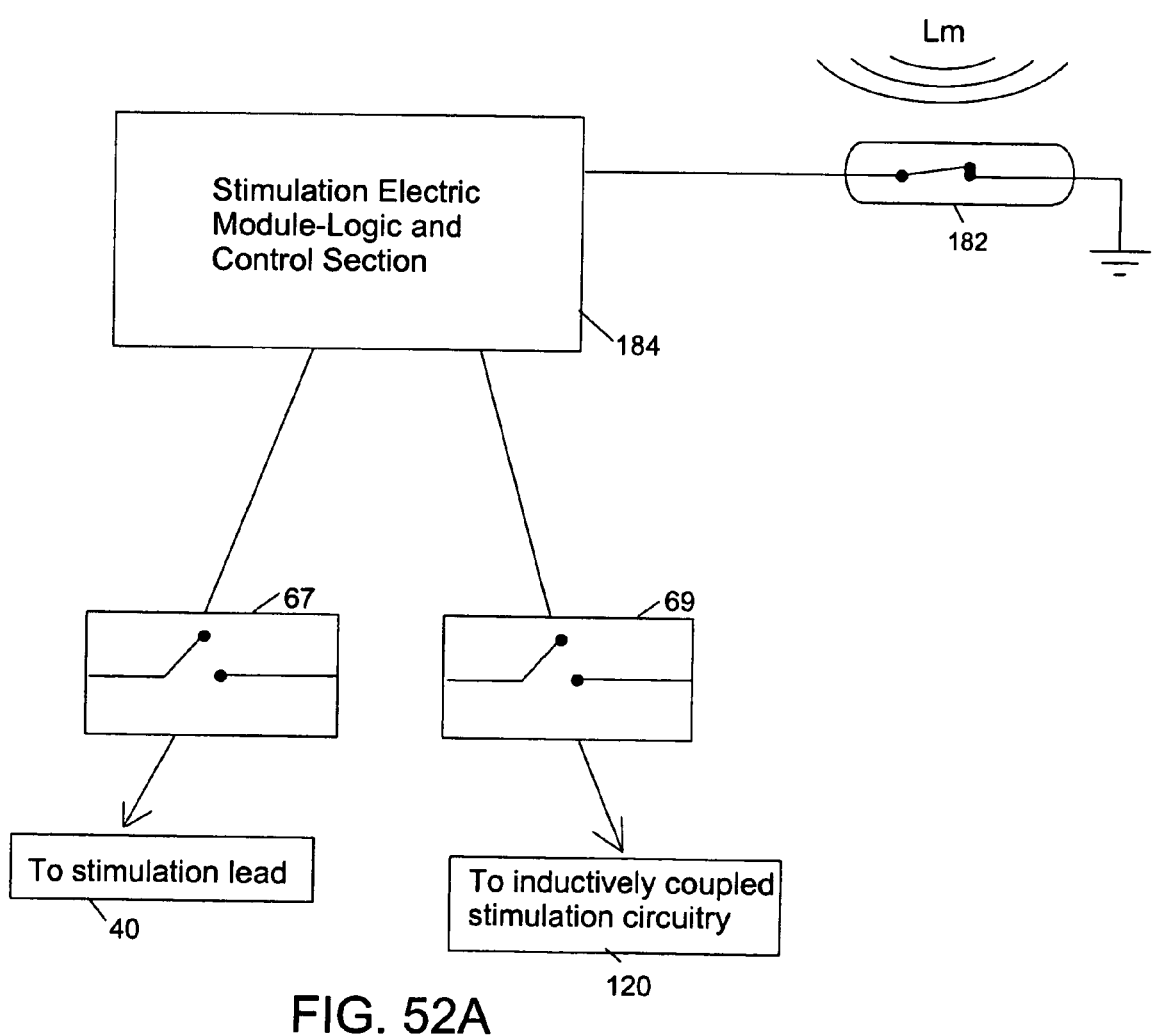
FIGS. 52A and 52B are simplified block diagrams showing the switching relationships between the inductively coupled and battery powered assemblies of the pulse generator.
Figure 52B:
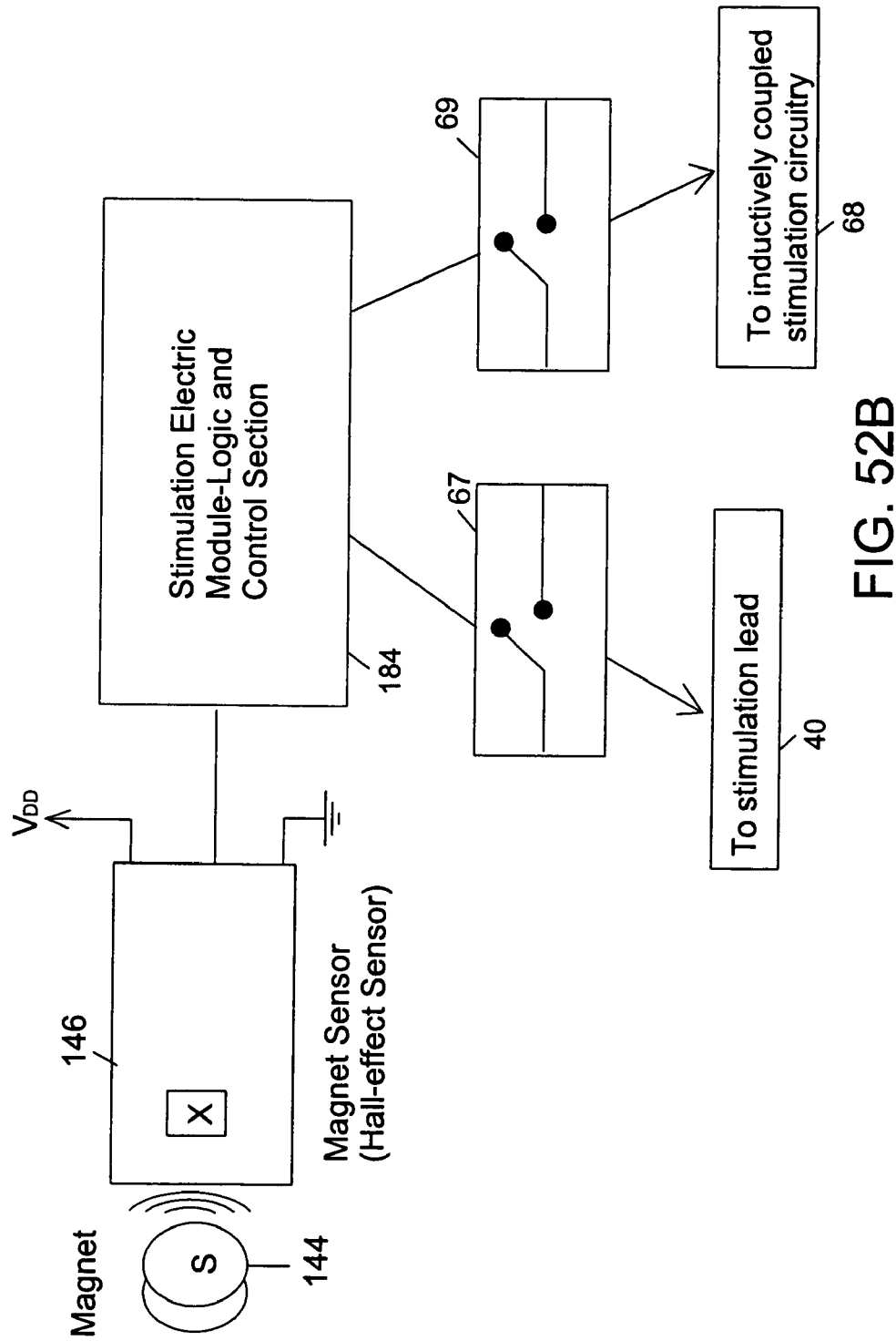

FIG. 52A is a simplified diagram of one aspect of control circuitry. In this embodiment, to program the implanted portion of the stimulator 70, a magnet 144 is placed over the implanted pulse generator 70, causing a magnetically controlled Reed Switch 182 (which is normally in the open position) to be closed. As is also shown in FIG. 52A, at the same time a switch 67 going to the stimulator lead 40, and a switch 69 going to the circuit of the stimulus-receiver module 120 are both opened, disconnecting both subassemblies electrically. Further, protection circuitry 181 is an additional safeguard for inadvertent leakage of electrical energy into the nerve tissue 54 during programming. Alternatively, as shown in FIG. 52B, instead of a reed switch 182, a solid state magnet sensor (Hall-effect sensor) 146 may be used for the same purpose. The solid-state magnet sensor 146 is preferred, since there are no moving parts that can get stuck.

Figure 50:
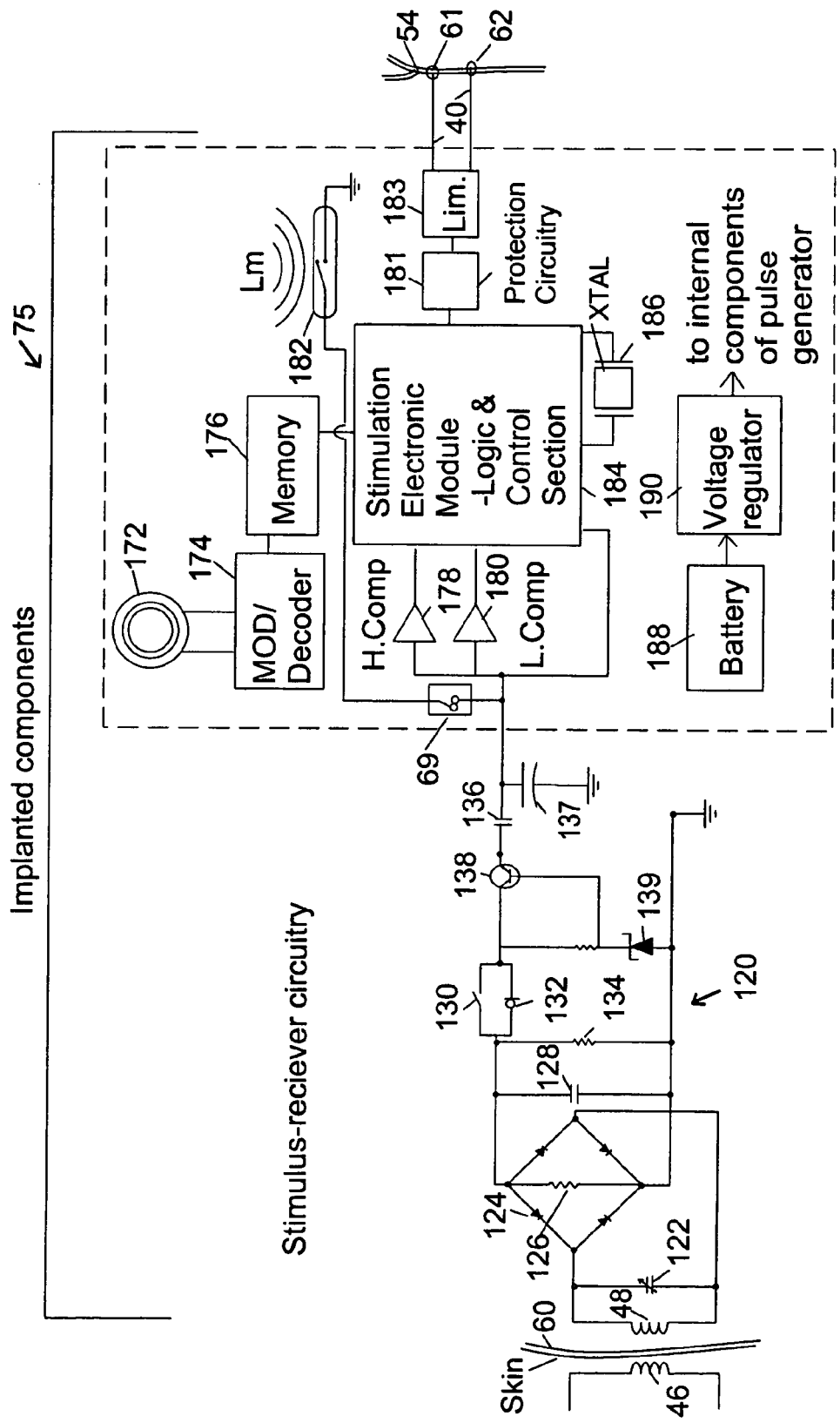
FIG. 50 is a schematic and functional block diagram showing the components and their relationships to the implantable pulse generator/stimulus-receiver.

With reference to FIG. 50, for the functioning of the inductively coupled stimulus-receiver 120, a primary (external) coil 46 is placed in close proximity to secondary (implanted) coil 48. The primary coil 46 may be taped to skin 60, or other means may be used for keeping the primary coil 46 in close proximity to the implanted (secondary) coil 48. Referring to the left portion of FIG. 50, the amplitude and pulse width modulated radiofrequency signals from the primary (external) coil 46 are inductively coupled to the secondary (implanted) coil 48 in the implanted unit 75. The two coils 46 and 48 thus act like an air-gap transformer. The system having means for proximity sensing between the two coils 46,48, and feedback regulation of signals as described earlier.

Again with reference to FIG. 50, the combination of capacitor 122 and inductor 48 tunes the receiver circuitry to the high frequency of the transmitter with the capacitor 122. The receiver is made sensitive to frequencies near the resonant frequency of the tuned circuit, and less sensitive to frequencies away from the resonant frequency. A diode bridge 124 rectifies the alternating voltages. Capacitor 128 and resistor 134 filter out the high-frequency component of the receiver signal, and leaves the current pulse of the same duration as the bursts of the high-frequency signal. A zenor diode 139 is used for regulation and capacitor 136 blocks any net direct current.

Figure 51A:
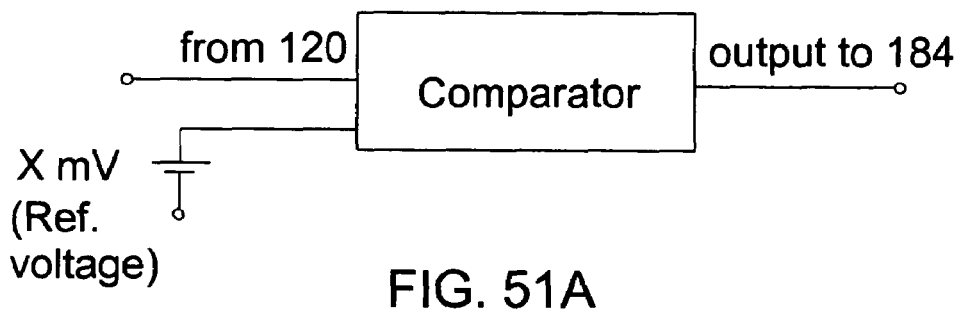
FIGS. 51A, 51B and 51C show output pulses from a comparator when input exceeds a reference voltage.
Figure 51B:
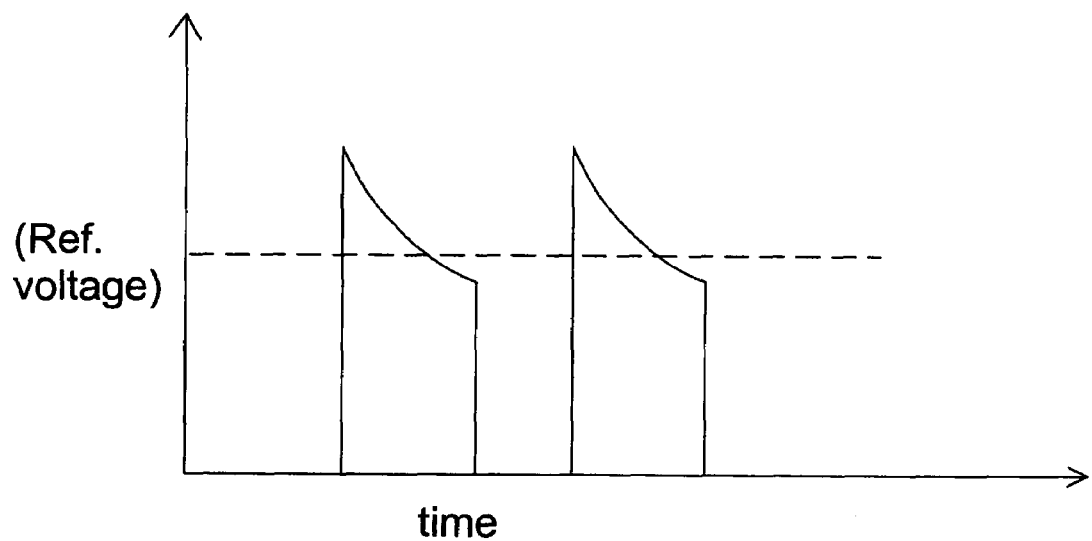
Figure 51C:
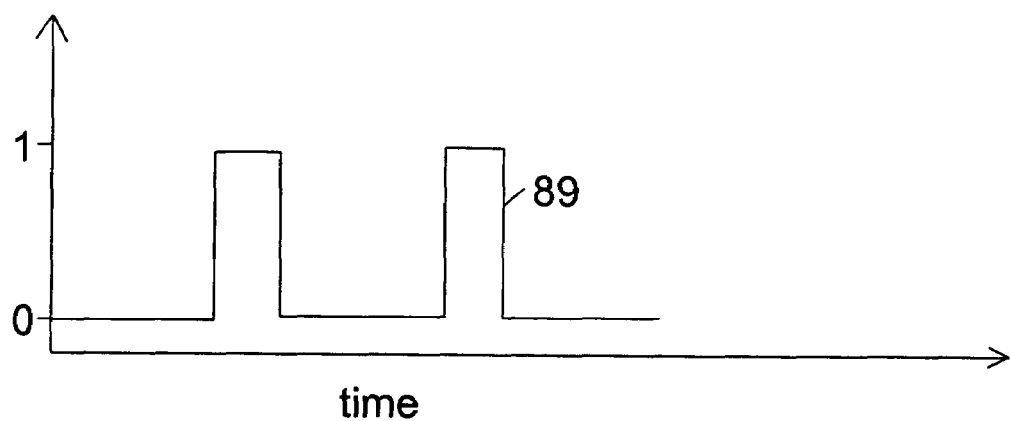

As shown in conjunction with FIGS. 50 and 51A the pulses generated from the stimulus-receiver circuitry 120 are compared to a reference voltage, which is programmed in the implanted pulse generator 70. When the voltage of incoming pulses exceeds the reference voltage (FIG. 51B), the output of the comparator 178, 180 sends digital pulse 89 (shown in FIG. 51C) to the stimulation electric module 184. At this predetermined level, the high threshold comparator 178 fires and the controller 184 suspends any stimulation from the implanted pulse generator 70. The implanted pulse generator 70 goes into "sleep" mode for a predetermined period of time. In one preferred embodiment, the level of voltage needed for the battery operated stimulator to go into "sleep" mode is a programmable parameter. The length of time, the implanted pulse generator 70 remains in "sleep" mode is also a programmable parameter. Therefore, advantageously the external stimulator 42 in conjunction with the inductively coupled part of the stimulator 120 can be used to save the battery life of the implanted stimulator 75.

In one embodiment, the external stimulator 42 is networked using the internet, giving the attending physician full control for activating and de-activating selected programs. Using "trial and error" various programs for electrical pulse therapy can be custom adjusted for the physiology of the individual patent. Also, by using the external stimulator 42, the battery 188 of the implanted stimulator unit 75 can be greatly extended. Further, even after the battery 188 is depleted, the system can still be used for neuromodulation using the stimulus-receiver module 120, and the external stimulator 42.

FIG. 53 shows a diagram of the finished implantable stimulator 75. FIG. 54 shows the pulse generator with some of the components used in assembly in an exploded view. These components include a coil cover 7, the secondary coil 48 and associated components, a magnetic shield 9, and a coil assembly carrier 11. The coil assembly carrier 11 has at least one positioning detail 13 located between the coil assembly and the feed through for positioning the electrical connection. The positioning detail 13 secures the electrical connection.

Implantable Pulse Generator (IPG) Comprising a Rechargeable Battery

Figure 55:
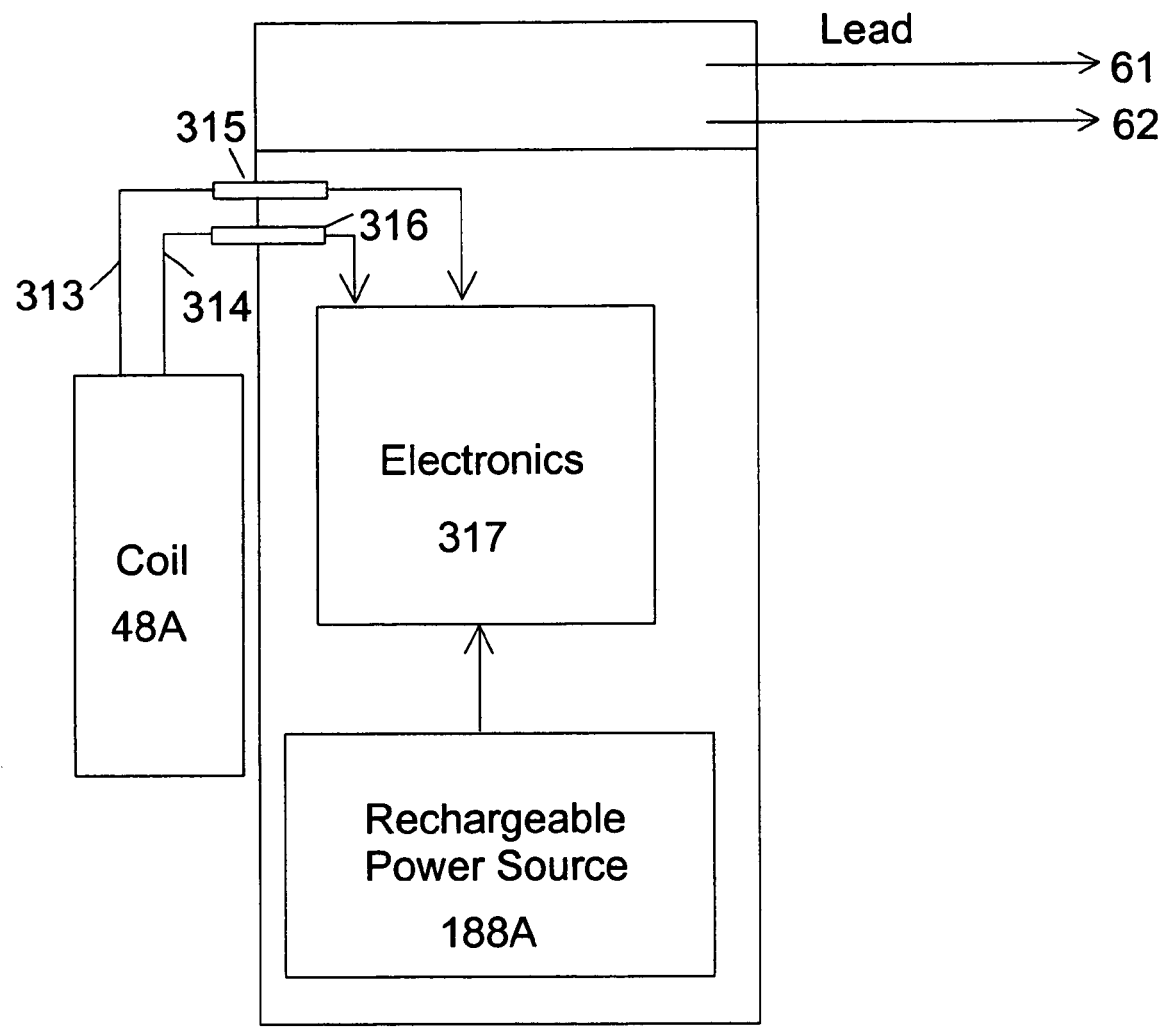
FIG. 55 depicts an embodiment where the implantable system is used as an implantable, rechargeable system.

In one embodiment, an implantable pulse generator with rechargeable power source can be used. In such an embodiment (shown in conjunction with FIG. 55), a recharge coil is external to the pulse generator titanium can. The RF pulses transmitted via coil 46 and received via subcutaneous coil 48A are rectified via diode bridge 154. These DC pulses are processed and the resulting current applied to recharge the battery 188A in the implanted pulse generator.

In summary, in the of current invention for providing pulse electrical stimulation to one of sacral plexus or branches, inferior hypogastric plexus or branches, superior hypogastric plexus or branches in a patient, to provide therapy for one of erectile/sexual dysfunction, prostatitis, pelvic pain, pain originating from prostatitis pathology, can be practiced with any of the several power sources disclosed including, a) an implanted stimulus-receiver with an external stimulator;

b) an implanted stimulus-receiver comprising a high value capacitor for storing charge, used in conjunction with an external stimulator;

c) a programmer-less implantable pulse generator (IPG) which is operable with a magnet;

d) a programmable implantable pulse generator;

e) a combination implantable device comprising both a stimulus-receiver and a programmable IPG; and f) an IPG comprising a rechargeable battery.

Neuromodulation of the appropriate nerve tissue(s) with any of these systems is considered within the scope of this invention.

In one embodiment, the external stimulator and/or the programmer has a telecommunications module, as described in a co-pending application, and summarized here for reader convenience. The telecommunications module has two-way communications capabilities.

Figure 57:
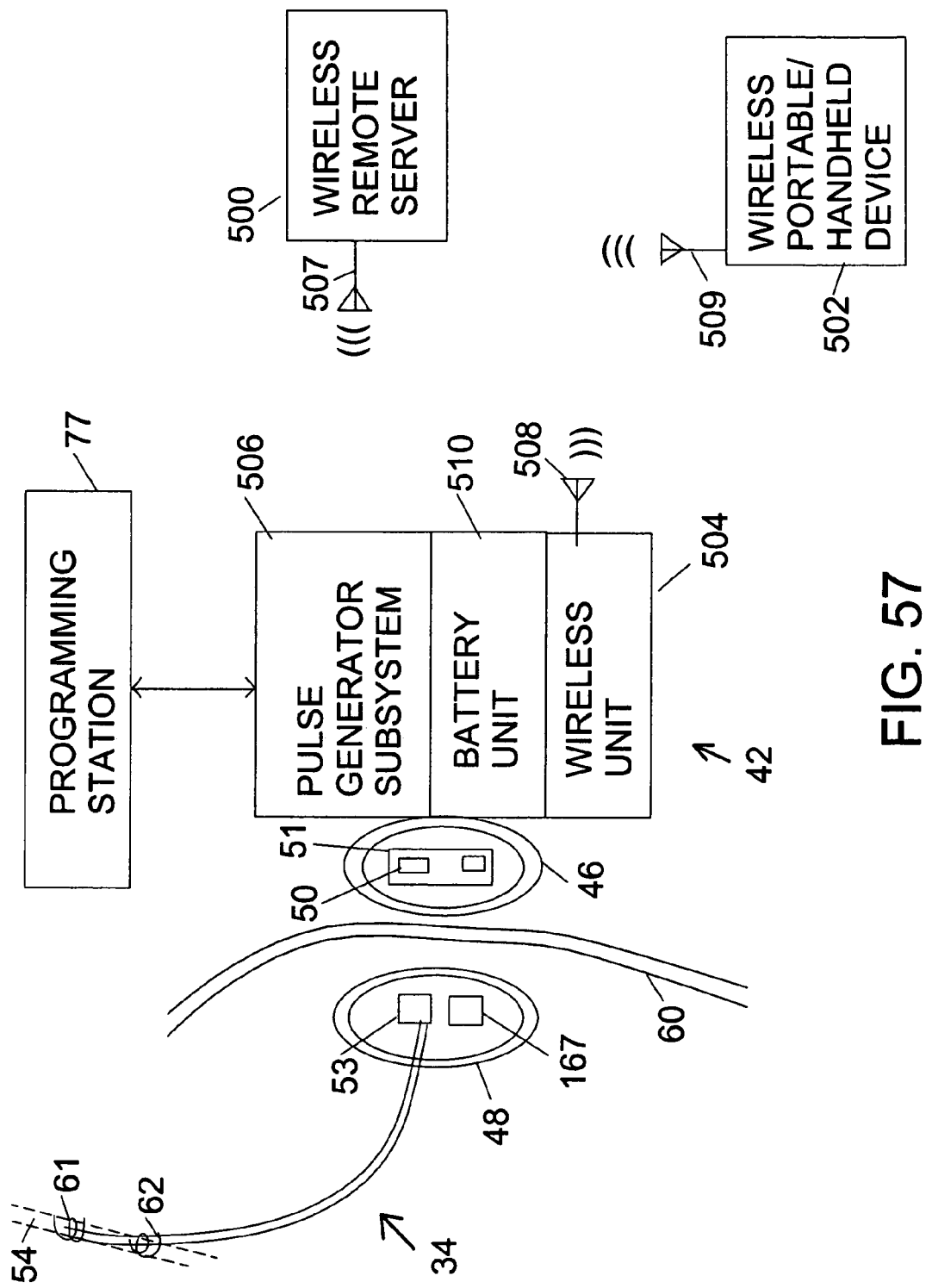
FIG. 57 is an overall schematic diagram of the external stimulator, showing wireless communication.

FIGS. 56 and 57 depict communication between an external stimulator 42 and a remote hand-held computer 502. A desktop or laptop computer can be a server 500 which is situated remotely, perhaps at a physician's office or a hospital. The stimulation parameter data can be viewed at this facility or reviewed remotely by medical personnel on a hand-held personal data assistant (PDA) 502, such as a "palm-pilot" from PALM corp. (Santa Clara, Calif.), a "Visor" from Handspring Corp. (Mountain view, Calif.) or on a personal computer (PC). The physician or appropriate medical personnel, is able to interrogate the external stimulator 42 device and know what the device is currently programmed to, as well as, get a graphical display of the pulse train. The wireless communication with the remote server 500 and hand-held PDA 502 would be supported in all geographical locations within and outside the United States (US) that provides cell phone voice and data communication service.

In one aspect of the invention, the telecommunications component can use Wireless Application Protocol (WAP). The Wireless Application Protocol (WAP), which is a set of communication protocols standardizing Internet access for wireless devices. While previously, manufacturers used different technologies to get Internet on hand-held devices, with WAP devices and services interoperate. WAP also promotes convergence of wireless data and the Internet. The WAP programming model is heavily based on the existing Internet programming model, and is shown schematically in FIG. 58. Introducing a gateway function provides a mechanism for optimizing and extending this model to match the characteristics of the wireless environment. Over-the-air traffic is minimized by binary encoding/decoding of Web pages and readapting the Internet Protocol stack to accommodate the unique characteristics of a wireless medium such as call drops.

Figure 58:
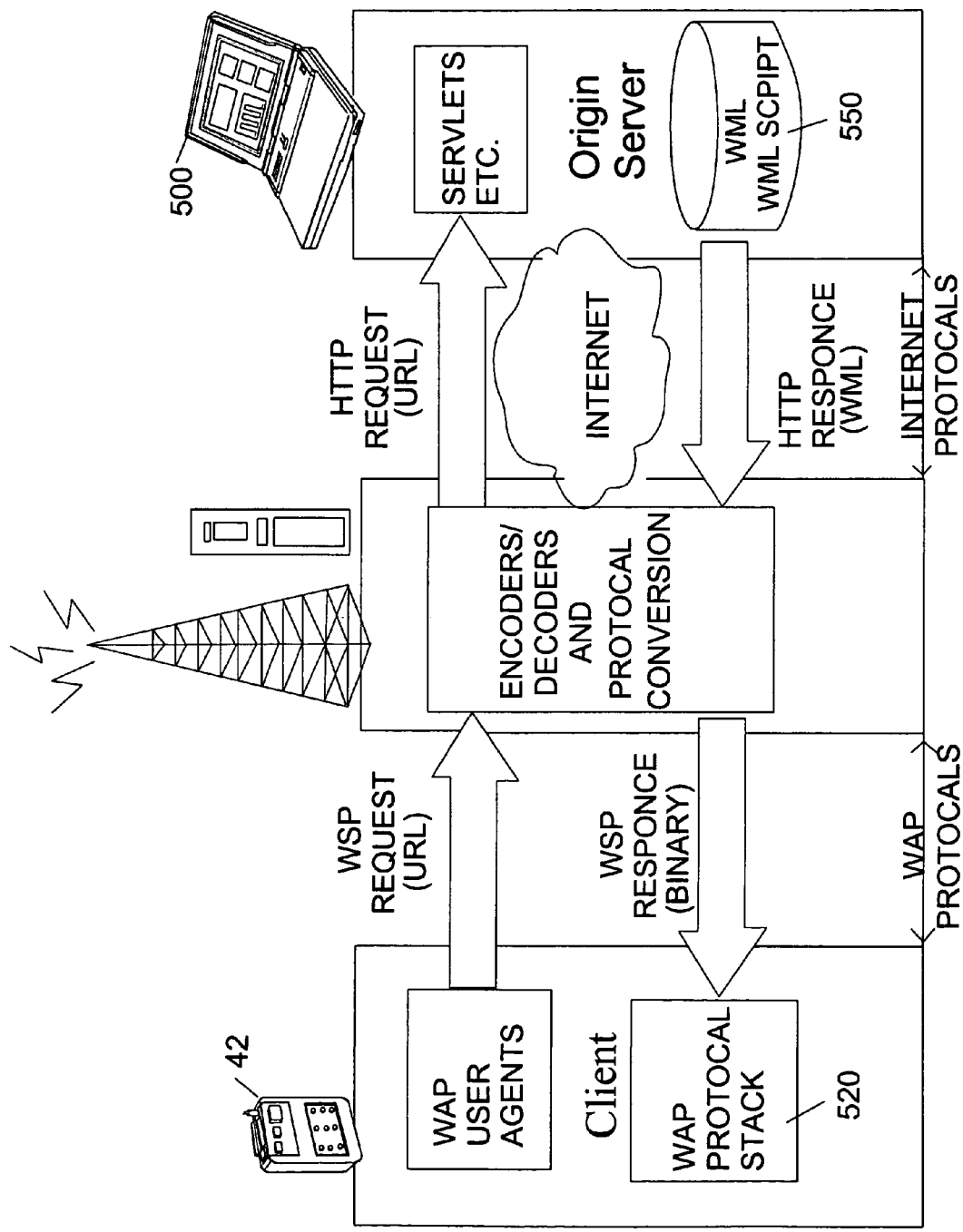
FIG. 58 is a schematic diagram showing application of Wireless Application Protocol (WAP).

The key components of the WAP technology, as shown in FIG. 58, includes 1) Wireless Mark-up Language (WML) 550 which incorporates the concept of cards and decks, where a card is a single unit of interaction with the user. A service constitutes a number of cards collected in a deck. A card can be displayed on a small screen. WML supported Web pages reside on traditional Web servers. 2) WML Script which is a scripting language, enables application modules or applets to be dynamically transmitted to the client device and allows the user interaction with these applets. 3) Microbrowser, which is a lightweight application resident on the wireless terminal that controls the user interface and interprets the WML/MLScript content. 4) A lightweight protocol stack 520 which minimizes bandwidth requirements, guaranteeing that a broad range of wireless networks can run WAP applications. The protocol stack of WAP can comprise a set of protocols for the transport (WTP), session (WSP), and security (WTLS) layers. WSP is binary encoded and able to support header caching, thereby economizing on bandwidth requirements. WSP also compensates for high latency by allowing requests and responses to be handled asynchronously, sending before receiving the response to an earlier request. For lost data segments, perhaps due to fading or lack of coverage, WTP only retransmits lost segments using selective retransmission, thereby compensating for a less stable connection in wireless. The above mentioned features are industry standards adopted for wireless applications and greater details have been publicized, and well known to those skilled in the art.

In this embodiment, two modes of communication are possible. In the first, the server initiates an upload of the actual parameters being applied to the patient, receives these from the stimulator, and stores these in its memory, accessible to the authorized user as a dedicated content driven web page. The physician or authorized user can make alterations to the actual parameters, as available on the server, and then initiate a communication session with the stimulator device to download these parameters.

Figure 59:
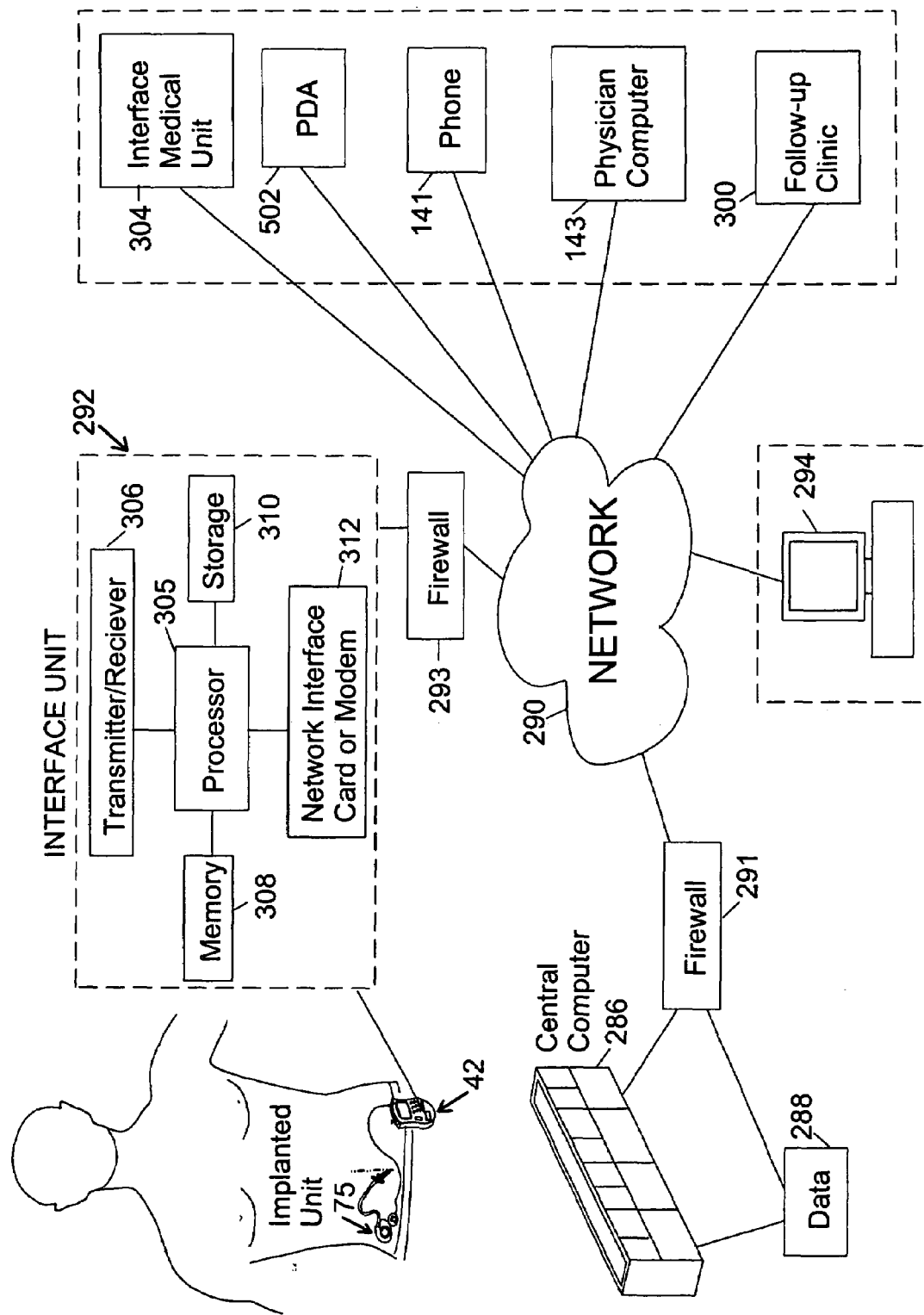
FIG. 59 is a simplified block diagram of the networking interface board.

Shown in conjunction with FIG. 59, in one embodiment, the external stimulator 42 and/or the programmer 85 may also be networked to a central collaboration computer 286 as well as other devices such as a remote computer 294, PDA 502, phone 141, physician computer 143. The interface unit 292 in this embodiment communicates with the central collaborative network 290 via land-lines such as cable modem or wirelessly via the internet. A central computer 286 which has sufficient computing power and storage capability to collect and process large amounts of data, contains information regarding device history and serial number, and is in communication with the network 290. Communication over collaboration network 290 may be effected by way of a TCP/IP connection, particularly one using the internet, as well as a PSTN, DSL, cable modem, LAN, WAN or a direct dial-up connection.

The standard components of interface unit shown in block 292 are processor 305, storage 310, memory 308, transmitter/receiver 306, and a communication device such as network interface card or modem 312. In the preferred embodiment these components are embedded in the external stimulator 42 and can also be embedded in the programmer 85. These can be connected to the network 290 through appropriate security measures (Firewall) 293.

Another type of remote unit that may be accessed via central collaborative network 290 is remote computer 294. This remote computer 294 may be used by an appropriate attending physician to instruct or interact with interface unit 292, for example, instructing interface unit 292 to send instruction downloaded from central computer 286 to remote implanted unit.

Figure 60A:
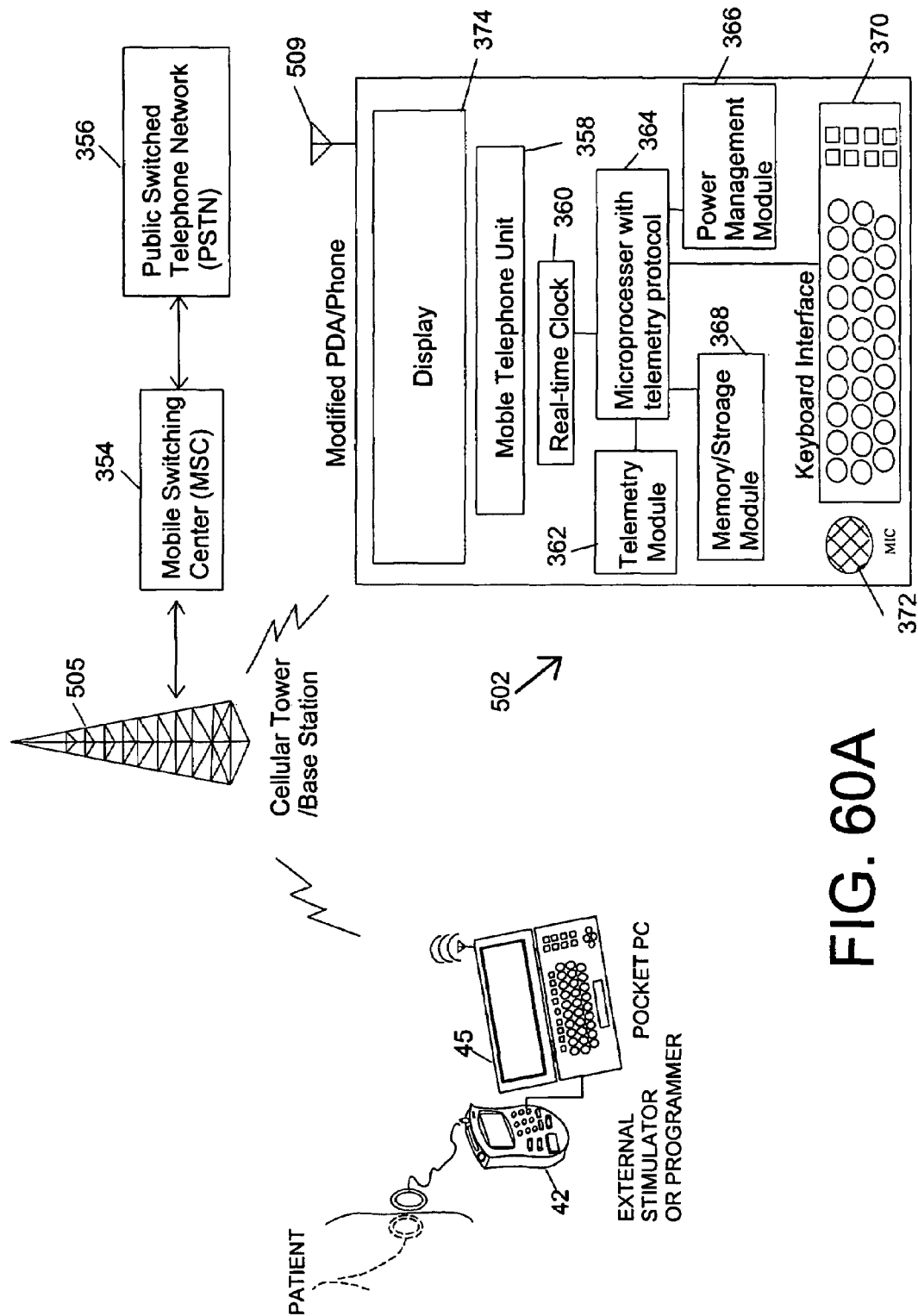
FIGS. 60A and 60B are simplified diagrams showing communication of modified PDA/phone with an external stimulator via a cellular tower/base station.
Figure 60B:
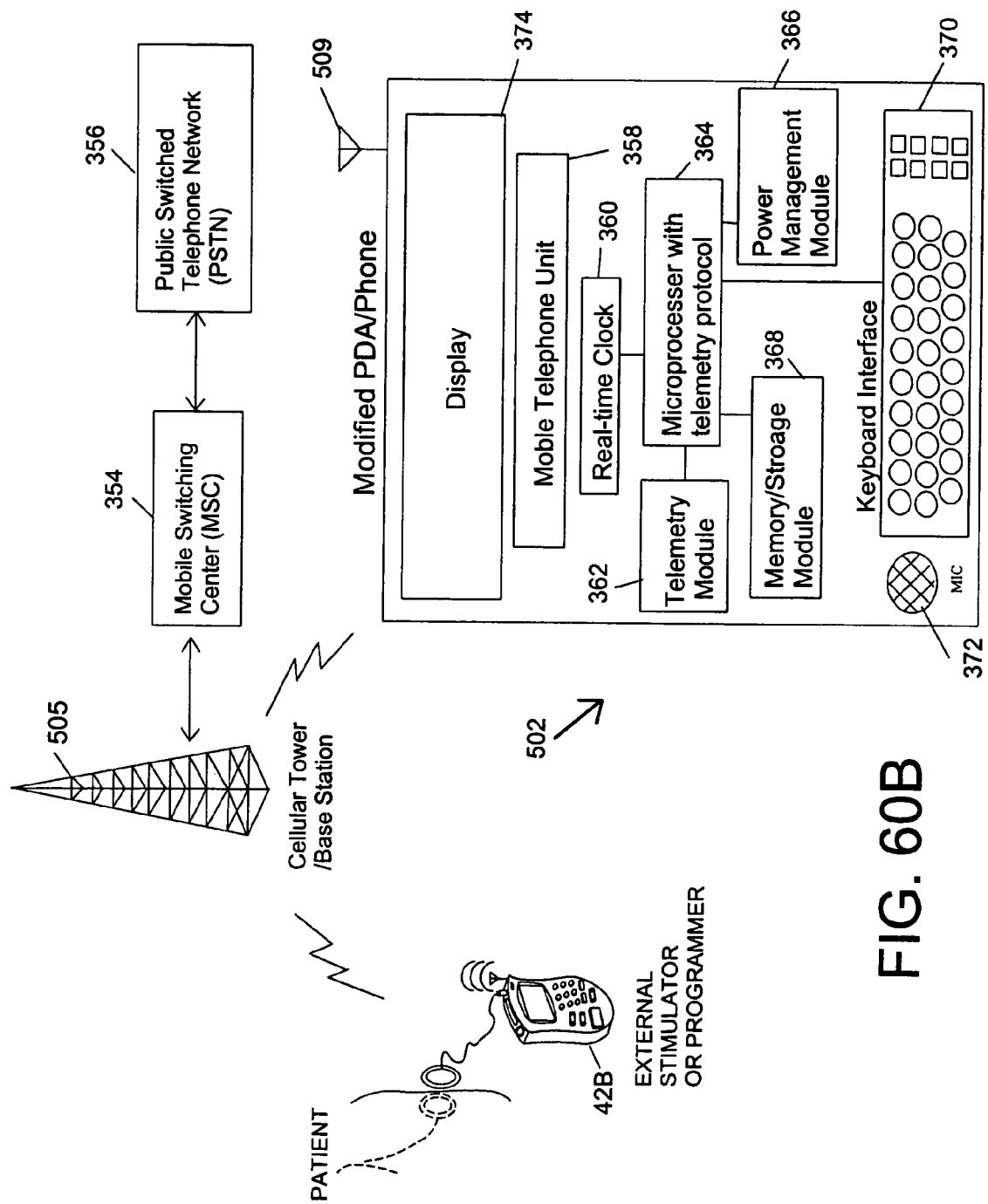

Shown in conjunction with FIGS. 60A and 60B the physician's remote communication's module is a Modified PDA/Phone 502 in this embodiment. The Modified PDA/Phone 502 is a microprocessor based device as shown in a simplified block diagram in FIGS. 65A and 65B. The PDA/Phone 502 is configured to accept PCM/CIA cards specially configured to fulfill the role of communication module 292 of the present invention. The Modified PDA/Phone 502 may operate under any of the useful software including Microsoft Window's based, Linux, Palm OS, Java OS, SYMBIAN, or the like.

The telemetry module 362 comprises an RF telemetry antenna 142 coupled to a telemetry transceiver and antenna driver circuit board which includes a telemetry transmitter and telemetry receiver. The telemetry transmitter and receiver are coupled to control circuitry and registers, operated under the control of microprocessor 364. Similarly, within stimulator a telemetry antenna 142 is coupled to a telemetry transceiver comprising RF telemetry transmitter and receiver circuit. This circuit is coupled to control circuitry and registers operated under the control of microcomputer circuit.

With reference to the telecommunications aspects of the invention, the communication and data exchange between Modified PDA/Phone 502 and external stimulator 42 operates on commercially available frequency bands. The 2.4-to-2.4853 GHz bands or 5.15 and 5.825 GHz, are the two unlicensed areas of the spectrum, and set aside for industrial, scientific, and medical (ISM) uses. Most of the technology today including this invention, use either the 2.4 or 5 GHz radio bands and spread-spectrum technology.

The telecommunications technology, especially the wireless internet technology, which this invention utilizes in one embodiment, is constantly improving and evolving at a rapid pace, due to advances in RF and chip technology as well as software development. Therefore, one of the intents of this invention is to utilize "state of the art" technology available for data communication between Modified PDA/Phone 502 and external stimulator 42. The intent of this invention is to use 3G technology for wireless communication and data exchange, even though in some cases 2.5G is being used currently.

For the system of the current invention, the use of any of the "3G" technologies for communication for the Modified PDA/Phone 502, is considered within the scope of the invention. Further, it will be evident to one of ordinary skill in the art that as future 4G systems, which will include new technologies such as improved modulation and smart antennas, can be easily incorporated into the system and method of current invention, and are also considered within the scope of the invention.

What is claimed is:

1. A method of providing pulsed electrical stimulation to at least one of sacral plexus, inferior hypogastric plexus, and superior hypogastric plexus or their branches or portion thereof, comprising the steps of:
    providing an implantable stimulator to provide electrical pulses, wherein said implantable stimulator comprises a pulse generator module and a stimulus-receiver module that receives external stimulus signals and is capable of applying said electrical pulses independently of said pulse generator module;
    providing an external stimulator adapted to be inductively coupled to said stimulus-receiver module; and
    providing at least one implanted lead in electrical contact with said implanted stimulator, and at least one electrode adapted to be in contact with at least one of sacral plexus, inferior hypogastric plexus, and superior hypogastric plexus or their branches or portion thereof,
    whereby pulsed electrical stimulation is provided to at least one of sacral plexus, inferior hypogastric plexus, and superior hypogastric plexus or their branches or portion thereof.

2. The method of claim 1, wherein said plexuses or their branches or portion thereof in a patient further comprises, at least one of a pudendal nerve or its branches or portion thereof, a cavernous nerve or its branches or portion thereof, a prostatic plexus nerve or its branches or portion thereof, a sacral splanchnic nerve or its branches or portion thereof, or pelvic splanchnic nerve or its branches or portion thereof, or sacral nerves S1, S2, S3, or S4.

3. The method of claim 1, wherein said implantable stimulator further comprises telemetry means, wherein said telemetry means allow said pulse generator to be remotely interrogated.

4. The method of claim 1, wherein said implantable stimulator further comprises telemetry means, wherein said telemetry means allow said electrical pulses to be remotely controlled.

5. The method of claim 1, wherein said pulsed electrical stimulation is provided to said nerves for unidirectional stimulation.

6. The method of claim 1, wherein said pulsed electrical stimulation is provided at any point along the length of said plexuses or their branches or portion thereof.

7. A method for treating or alleviating the symptoms for at least one of erectile/sexual dysfunction, prostatitis, pelvic pain, or pain originating from prostatitis pathology, with neuromodulation therapy, the method comprising:
    providing an implantable stimulator to provide electrical pulses, wherein said implantable stimulator comprises a pulse generator module and a stimulus-receiver module that receives external stimulus signals and is capable of applying said electrical pulses independently of said pulse generator module;
    providing an external stimulator adapted to be inductively coupled to said stimulus-receiver module; and
    providing at least one implanted lead in electrical contact with said implanted stimulator, and at least one electrode adapted to be in contact with at least one of sacral plexus, inferior hypogastric plexus, and superior hypogastric plexus or their branches or portion thereof,
    whereby electrical pulses are provided for treating or alleviating the symptoms for at least one of erectile/sexual dysfunction, prostatitis, pelvic pain, or pain originating from prostatitis pathology.

8. The method of claim 7, wherein said plexuses or their branches or portion thereof in a patient further comprises, at least one of pudendal nerve or its branches or portion thereof, cavernous nerve or its branches or portion thereof, prostatic plexus nerve or its branches or portion thereof, sacral splanchnic nerve or its branches or portion thereof, or pelvic splanchnic nerve or its branches or portion thereof, or sacral nerves S1, S2, S3, or S4.

9. The method of claim 7, wherein said neuromodulation therapy is provided by providing electrical pulses at any point along the length of said plexuses or their branches or portion thereof.

10. A system for providing pulsed electrical stimulation to at least one of sacral plexus, inferior hypogastric plexus, supereior hypogastric plexus or their branches or portion thereof in a patient, comprising:
providing an implantable stimulator to provide electrical pulses, wherein said implantable stimulator comprises a pulse generator module and a stimulus-receiver module that receives external stimulus signals and is capable of applying said electrical pulses independently of said pulse generator module;
providing an external stimulator adapted to be inductively coupled to said stimulus-receiver module; and
providing at least one implanted lead in electrical contact with said implanted stimulator, and at least one electrode adapted to be in contact with at least one of sacral plexus, inferior hypogastric plexus, supereior hypogastric plexus or their branches or portion thereof,
whereby said system can provide pulsed electrical stimulation to at least one of sacral plexus, inferior hypogastric plexus, supereior hypogastric plexus or their branches or portion thereof in a patient for treating or alleviating the symptoms for at least one of erectile/sexual dysfunction, prostatitis, pelvic pain, or pain originating from prostatitis pathology.

11. The system of claim 10, wherein said plexuses or their branches or portion thereof in a patient further comprises, at least one of pudendal nerve or its branches or portion thereof, cavernous nerve or its branches or portion thereof, prostatic plexus or its branches or portion thereof, sacral splanchnic nerve or its branches or portion thereof, or pelvic splanchnic nerve or its branches or portion thereof, or sacral nerves S1, S2, S3, or S4.

12. The system of claim 10, wherein said implantable stimulator comprises a rechargeable battery.

13. The system of claim 10, wherein said implantable stimulator further comprises network telemetry, wherein said network telemetry allows said stimulation and/or interrogation of said implantable stimulator to be remotely controlled.

14. The system of claim 10, wherein said pulsed electrical stimulation is provided for unidirectional stimulation.

15. The system of claim 10, wherein said pulsed electrical stimulation is provided at any point along the length of at least one of said plexuses or their branches or portion thereof.

16. The system of claim 10, wherein said implantable lead comprises a lead body with insulation selected from the group consisting of polyurethane, silicone and silicone with polytetrafluoroethylene.

17. The system of claim 10, wherein said at least one electrode is from a group comprising, spiral electrodes, cuff electrodes, steroid eluting electrodes, wrap-around electrodes, and hydrogel electrodes.

18. The system of claim 17, wherein said electrodes are made from material from one of a group comprising of pure platinum, platinum-iridium alloy, platinum-iridium coated with titanium nitride, or carbon.

* * * * *